United States Patent [19]

Joyce

[11] Patent Number: 5,580,967
[45] Date of Patent: Dec. 3, 1996

[54] OPTIMIZED CATALYTIC DNA-CLEAVING RIBOZYMES

[75] Inventor: Gerald F. Joyce, Encinitas, Calif.

[73] Assignee: The Scripps Research Institute, La Jolla, Calif.

[21] Appl. No.: 242,402

[22] Filed: May 13, 1994

[51] Int. Cl.$^6$ .................... C12N 9/22; C12Q 1/68
[52] U.S. Cl. .......... 536/23.2; 536/23.1; 536/24.5; 435/6; 435/91.31; 435/172.1; 435/172.3
[58] Field of Search .................. 536/24.1, 23.1, 536/23.2, 24.5, 24.1, 25.1, 25.3; 435/6, 91.2, 91.3, 91.31, 172.1, 172.3, 199, 91.53, 195; 514/44

[56] References Cited

FOREIGN PATENT DOCUMENTS

93/23569  11/1993  WIPO.

OTHER PUBLICATIONS

Joyce, Pure & Appl. Chem 65 (1993), pp. 1205–1212.
Mills, et al., "An Extracellular Darwinian Experiment With a Self–Duplicating Nucleic Acid Molecule", *PNAS, USA* 58: 217–224 (1967).
Green, et al., "In Vitro Genetic Analysis of the Tetrahymena Self–Splicing Intron", *Nature* 347: 406–408 (1990).
Chowrira, et al., "Novel Guanosine Requirement for Catalysis for the Hairpin Ribozyme", *Nature* 354: 320–322 (1991).
Joyce, "Amplification, Mutation and Selection of Catalytic RNA", *Gene* 82: 83–87 (1989).
Beaudry and Joyce, "Directed Evolution of an RNA Enzyme", *Science* 257: 635–641 (1992).
Robertson and Joyce, "Selection In Vitro of an RNA Enzyme that Specifically Cleaves Single–Stranded DNA", *Nature* 344: 467–468 (1990).
Tuerk, et al., "Systematic Evolution of Ligands by Exponential Enrichment: RNA Ligands to Bacteriophage T4 DNA Polymerase", *Science* 249: 505–510 (1990).
Ellington, et al., "In Vitro Selection of RNA Molecules that Bind Specific Ligands", *Nature* 346: 818–822 (1990).
Lam, et al., "A New Type of Synthetic Peptide Library for Identifying Ligand–Binding Activity", *Nature* 354: 82–84 (1991).
Scott, et al., "Searching for Peptide Ligands With an Epitope Library", *Science* 249: 386–390 (1990).
Devlin, et al., "Random Peptide Libraries: A Source of Specific Protein Binding Molecules", *Science* 249: 404–406 (1990).
Cwirla, et al., "Peptides on Phage: A Vast Library of Peptides for Identifying Ligands", *PNAS USA* 87: 6378–6382 (1990).
Wang and Cech, "Tertiary Structure Around the Guanosine–Binding Site of the Tetrahymena Ribozyme", *Science* 256: 526–529 (1992).
Zaug and Cech, "The Intervening Sequence RNA of Tetrahymena is an Enzyme", *Science* 231: 470–475 (1986).
Inoue, et al., "New Reactions of the Ribosomal RNA Precursor of Tetrahymena and the Mechanism of Self–Splicing", *J. Mol. Biol.* 189: 143–165 (1986).
Joyce, et al., "Catalytic Activity is Retained in the Tetrahymena Group I Intron Despite Removal of the Large Extension of Element P5", *Nucl. Acids Res.* 17: 7879–7889 (1989).
Cadwell and Joyce, "Randomization of Genes by PCR Mutagenesis", *PCR Methods Appl.* 2: 28–33 (1992).
Lehman & Joyce, "Evolution In Vitro of an RNA Enzyme With Altered Metal Dependence", *Nature* 361: 182–185 (1993).
Joyce and Inoue, "A Novel Technique for the Rapid Preparation of Mutant RNAs", *Nucl. Acids Res.* 17: 711–722 (1989).

*Primary Examiner*—John L. LeGuyader
*Assistant Examiner*—Thomas G. Larson
*Attorney, Agent, or Firm*—April C. Logan

[57] ABSTRACT

The present invention discloses nucleic acid enzymes capable of cleaving nucleic acid molecules, including single-stranded DNA, in a site-specific manner under physiologic conditions, as well as compositions including same. The present invention also discloses methods of making and using the disclosed enzymes and compositions.

8 Claims, 8 Drawing Sheets

GENERATION 36

OPTIMIZED CATALYTIC DNA-CLEAVING RIBOZYMES

DESCRIPTION

This invention was made with government support under NASA Grant No. NAGW-1671 and NIH Grant No. AI30882. The government has certain rights in the invention.

TECHNICAL FIELD

The present invention relates to nucleic acid enzymes or enzymatic RNA molecules for cleaving DNA under physiologic conditions, compositions containing same, and to methods of making and using such enzymes and compositions.

BACKGROUND

The need for catalysts that operate outside of their native context or which catalyze reactions that are not represented in nature has resulted in the development of "enzyme engineering" technology. The usual route taken in enzyme engineering has been a "rational design" approach, relying upon the understanding of natural enzymes to aid in the construction of new enzymes. Unfortunately, the state of proficiency in the areas of protein structure and chemistry is insufficient to make the generation of novel biological catalysts routine.

Recently, a different approach for developing novel catalysts has been applied. This method involves the construction of a heterogeneous pool of macromolecules and the application of an in vitro selection procedure to isolate molecules from the pool that catalyze the desired reaction. Selecting catalysts from a pool of macromolecules is not dependent on a comprehensive understanding of their structural and chemical properties. Accordingly, this process has been dubbed "irrational design" (Brenner and Lerner, *PNAS USA* 89: 5381–5383 (1992)).

The process of Darwinian evolution, by which enzymes arise in nature, does not operate by generating a diverse population of variants and harvesting the most advantageous individuals. In biological systems, diversity is maintained by ongoing mutations, and the population is shaped by selection. Novel mutations augment existing variation, so that the evolutionary search is biased, in an appropriate fashion, by selection events that have already occurred (Eigen, et al., *J. Phys. Chem.* 92: 6881 (1988)). The more advantageous mutants, which are relatively abundant in the population, give rise to larger numbers of novel variants when compared to the less advantageous mutants.

Most efforts to date involving the rational design of enzymatic RNA molecules or ribozymes have not led to molecules with fundamentally new or improved catalytic function. However, the application of irrational design methods via a process we have described as "directed molecular evolution" or "in vitro evolution", which is patterned after Darwinian evolution of organisms in nature, has the potential to lead to the production of RNA molecules that have desirable functional characteristics.

This technique has been applied with varying degrees of success to RNA molecules in solution (see, e.g., Mills, et al., *PNAS USA* 58: 217 (1967); Green, et al., *Nature* 347: 406 (1990); Chowrira, et al., *Nature* 354: 320 (1991); Joyce, *Gene* 82: 83 (1989); Beaudry and Joyce, *Science* 257: 635–641 (1992); Robertson and Joyce, *Nature* 344: 467 (1990)), as well as to RNAs bound to a ligand that is attached to a solid support (Tuerk, et al., *Science* 249: 505 (1990); Ellington, et al., *Nature* 346: 818 (1990)). It has also been applied to peptides attached directly to a solid support (Lam, et al., *Nature* 354: 82 (1991)); and to peptide epitopes express/ed within a viral coat protein (Scott, et al., *Science* 249: 386 (1990); Devlin, et al., *Science* 249: 404 (1990); Cwirla, et al., *PNAS USA* 87: 6378 (1990)).

However, as disclosed herein, we have achieved a remarkable degree of success in engineering new enzymatically active oligonucleotide molecules. Therefore, the discoveries and inventions disclosed herein are particularly significant, in that they highlight the potential of in vitro evolution as a means of designing increasingly more efficient catalytic molecules.

BRIEF SUMMARY OF THE INVENTION

Site-directed mutagenesis has now been improved by in vitro selected amplification techniques for generating large numbers of mutants with subsequent selection of some desirable property. Individual macromolecules are selected, and those selected are then amplified to generate a progeny distribution of favorable mutants. The process is repeated until only those individuals with the most desirable properties remain.

Therefore, in various disclosed embodiments of the present invention, enzymatic nucleic acids, particularly enzymatic RNA molecules, are prepared, selected, and synthesized in useful quantities for various uses. Selection criteria include, without limitation, the ability of the enzymatic RNA molecule to catalyze a sequence-specific reaction, to cleave nucleic acids, to bind substrate DNA and/or RNA, to display an improved turnover rate, and the like.

Therefore, the present invention contemplates enzymatic RNA molecules capable of specifically cleaving a single-stranded nucleic acid molecule under physiologic conditions, wherein the enzymatic RNA molecules include one or more point mutations which improve the enzymatic performance of the enzymatic RNA molecules. In various embodiments, the enzymatic RNA molecule further includes one or more point mutations which affect the substrate specificity of the enzymatic RNA molecule.

In one variation, the enzymatic performance comprises catalytic efficiency. Alternative embodiments contemplate that the enzymatic RNA molecule has a cleavage rate of about 0.7 min$^{-1}$.

It is also contemplated that enzymatic performance may comprise substrate binding affinity. In various embodiments, the substrate may comprise DNA, RNA, or composites thereof. In embodiments in which the substrate comprises DNA, an enzymatic RNA molecule may have a substrate binding affinity of at least 10$^{-9}$M. In other variations, an enzymatic RNA molecule of the present invention binds DNA with a $K_D$ of less than 10 µM. In alternative embodiments, an enzymatic RNA molecule of the present invention binds DNA with a $K_D$ of less than 1 µM; with a $K_D$ of less than 50 nM; or with a $K_D$ of less than 10 nM.

In embodiments in which the substrate comprises RNA, an enzymatic RNA molecule preferably binds RNA with a $K_D$ of less than 1.0 nM, and more preferably, with a $K_D$ of 0.5 nM or less. In other embodiments, an enzymatic RNA molecule has an RNA substrate cleavage rate up to three times greater than that of wild-type ribozymes. Still other embodiments contemplate enzymatic RNA molecules wherein enzymatic performance comprises substrate specificity. In various embodiments, that specificity is changed via altering the recognition sequence. As noted above, substrates may comprise DNA, RNA, or composites thereof.

In embodiments in which the substrate comprises DNA, an enzymatic RNA molecule invention preferably has a DNA substrate cleavage rate $10-10^2$, $10^2-10^3$, $10^3-10^4$, or even $10^4-10^5$ times greater than that of wild-type ribozymes. A cleavage rate exceeding $10^5$ is also contemplated in various embodiments.

The present invention further contemplates enzymatic RNA molecules derived from group I, II, III, or IV introns. Preferably, an enzymatic RNA molecule of the present invention is derived from a group I intron. In one variation, the group I intron is a Tetrahymena group I intron. In another variation, an enzymatic RNA molecule contemplated herein comprises the portions of a Tetrahymena group I intron having catalytic activity. In yet another embodiment, an enzymatic RNA molecule of the present invention is derived from an L-19 or L-21 RNA molecule and includes the portions of the L-19 or L-21 RNA molecule having the catalytic activity.

Various embodiments of the disclosed invention contemplate that an enzymatic RNA molecule of the present invention includes one or more mutations not typically found in wild type enzymatic RNA molecules or ribozymes. In various embodiments, the mutations are selected from the group consisting of: 44:G→A; 51/52:insert AGAA; 87:A→deleted; 94:A→U; 94:A→C; 115:A→U; 116:G→A; 138:C→A; 166:C→A; 167:U→G; 170:C→U; 188:G→A; 190:U→A; 191:G→U; 205:U→C; 215:G→A; 239:U→A; 258:U→C; 312:G→A; 313:G→U; 313:G→C; 314:A→G; 317:U→G; 317:U→C 317:U→A; 333:U→C; 350:C→U; and 364:C→U.

In various alternative embodiments, an enzymatic RNA molecule of the present invention has 1–4 point mutations, 5–8 point mutations, 9–12 point mutations, or 13 or more point mutations. In various exemplary embodiments, the point mutations may comprise a 215:G→A mutation, a 258:U→C mutation, or both. In another embodiment, an enzymatic RNA molecule includes the following mutations: 94:A→Y, 215:C→A, and 313–314:GA→UG. Still another example includes the mutations 94:A→Y, 215:G→A, 313–314:GA→UG, and 317:U→R, while yet another example includes the mutations 94:A→Y, 215:G→A, 313–314:GA→UG, and 333:U→C.

In another embodiment, an enzymatic RNA molecule includes the following mutations: 94:A→Y and 313–314:GA→UG. Still another example includes the following mutations: 215:G→A and 313–314:GA→UG. In yet another embodiment, an enzymatic RNA molecule of the present invention includes the following mutations: 94:A→Y, 115:A→U, 116:G→A, 188:G→A, 90:U→A, 191:G→U, 205:U→C, 215:G→A, and 313–314:GA→UG.

In another variation, the invention contemplates an enzymatic RNA molecule including the following mutations: 44:G→A, 87:A→del, 94:A→U, 115:A→U, 116:G→A, 166:C→A, 170:C→U, 188:G→A, 190:U→A, 191:G→U, 205:U→C, and 215:G→A.

Other examples of combinations of mutations which may be present in enzymatic RNA molecules of the present invention include the following: (a) 98:C→U and 313–314:GA→UG; (b) 98:C→U, 205:U→C, and 317:U→R; (c) 94:A→Y and 215:G→A; (d) 94:A→Y, 205:U→C, and 313–314:GA→UG; (e) 94:A→Y, 98:C→U, and 333:U→C; (f) 44:G→A, 94:A→U, 115:A→U, 116:G→A, 138:C→A, 188:G→A, 190:U→A, 191:G→U, 205:U→C, 215:G→A, 312:G→A, and 317:U→G, (g) 44:G→A, 94:A→U, 115:A→U, 116:G→A, 138:C→A, 167:U→G, 188:G→A, 190:U→A, 191:G→U, 205:U→C, 215:G→A, 239:U→A, and 312:G→A; (h) 44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 239:U→A, 312:G→A, 350:C→U, and 364:C→U; or (i) 44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 313:G→C, and 314:A→G.

In various disclosed embodiments, the mutations are concerted. In one exemplary embodiment, the concerted mutations comprise a tandem 313–314: GA→UG mutation. In another example, the concerted mutations comprise a 215:G→A mutation and a 258:U→C mutation.

In yet another variation, the concerted mutations comprise mutations at nucleotide positions 188, 190, and 191. In still another variation, the concerted mutations comprise mutations at nucleotide positions 115, 116, and 205. Another embodiment includes concerted mutations comprising mutations at nucleotide positions 115, 116, 188, 190, 191, and 205.

The present invention further contemplates an enzymatic RNA molecule capable of specifically cleaving single-stranded DNA under physiologic conditions, wherein the enzymatic RNA molecule includes one or more point mutations which affect the enzymatic performance of the molecule. In various embodiments, an enzymatic RNA molecule of the present invention further includes one or more point mutations which affect the substrate specificity of the molecule.

The present invention also contemplates various methods of making and using enzymatic RNA molecules according to the present invention. For example, a method for specifically cleaving a single-stranded DNA molecule under physiologic conditions, is contemplated herein, which comprises the steps of:

(a) providing an enzymatic RNA molecule having a deoxyribonuclease activity;

(b) contacting the enzymatic RNA molecule with a single-stranded DNA molecule under physiologic conditions; and (c) maintaining the contact for a sufficient time to allow the enzymatic RNA molecule to cause the single-stranded DNA molecule to be cleaved.

In another embodiment, the method further comprises providing the enzymatic RNA molecule in a reaction medium at a concentration sufficient to cause cleavage of about one molecule of DNA per molecule of enzymatic RNA per minute. In yet another embodiment, the method further comprises providing the enzymatic RNA molecule in a reaction medium, wherein the enzymatic RNA molecule is present at a concentration sufficient to cause cleavage of at least 10% of a population of DNA molecules in an hour.

In one variation of the disclosed methods for specifically cleaving a single-stranded DNA molecule under physiologic conditions, an enzymatic RNA molecule comprises a binding site for single-stranded DNA, which binding site is complementary to nucleotides adjacent to a cleavage site on the single-stranded DNA molecule. In another variation of the disclosed methods, an enzymatic RNA molecule of the present invention comprises a binding site for single-stranded DNA, which binding site is complementary to nucleotides adjacent to a cleavage site on the single-stranded DNA molecule.

The invention also contemplates a method of producing an enzymatic RNA molecule having a predetermined catalytic activity, comprising:

(a) subjecting a population of enzymatic RNA molecules to mutagenizing conditions to produce a diverse population of mutant RNA molecules;

(b) selecting an enzymatic RNA molecule having a predetermined activity from the diverse population of mutant enzymatic RNA molecules; and (c) separating the RNA molecule from the diverse population of mutant RNA molecules.

In one alternative method, the mutagenizing conditions comprise conditions that introduce defined or random nucleotide substitutions within an enzymatic RNA molecule. In another variation, the mutagenizing conditions comprise chemical modification, incorporation of randomized mutagenic oligodeoxynucleotides, or inaccurate copying by a polymerase. In yet another variation, the mutagenizing conditions comprise use of site-directed mutagenesis, polymerase chain reaction, or self-sustained sequence replication.

In various embodiments, the predetermined activity comprises the ability to cleave DNA under physiologic conditions.

Another variation of the foregoing methods further comprises the step of amplifying the enzymatic RNA molecules selected from the diverse population. In one embodiment, the amplifying is performed using a polymerase chain reaction. In another embodiment, the amplifying is performed using self-sustained sequence replication.

BRIEF DESCRIPTION OF THE DRAWINGS

FIG. 2 (A and B) illustrates the general procedure for selective amplification of catalytic RNA.

FIG. 8 (A–C) illustrates sites at which mutations occurred over the course of evolution, superimposed on the secondary structure of the Tetrahymena ribozyme. Box height corresponds to the frequency of mutations (%) at each nucleotide position, based on 50 subclones sequenced at generations 9 (G9.

FIG. 9A represents a typical binding curve showing data obtained for the G27 population of ribozymes. J and B indicate data from two different gel-shift experiments. Data was fit by a least squares method to a theoretical binding curve (indicated by solid line), given by the equation: y=[E]/([E]+K$_D$), where y is the fraction of product (P) bound to ribozyme (E). In this case, K$_D$=51 (±2) nM. FIG. 9B shows the K$_D$ for the population of ribozymes at every third generation. Standard errors averaged 11%.

DETAILED DESCRIPTION OF THE INVENTION

A. Definitions

Figure 1:
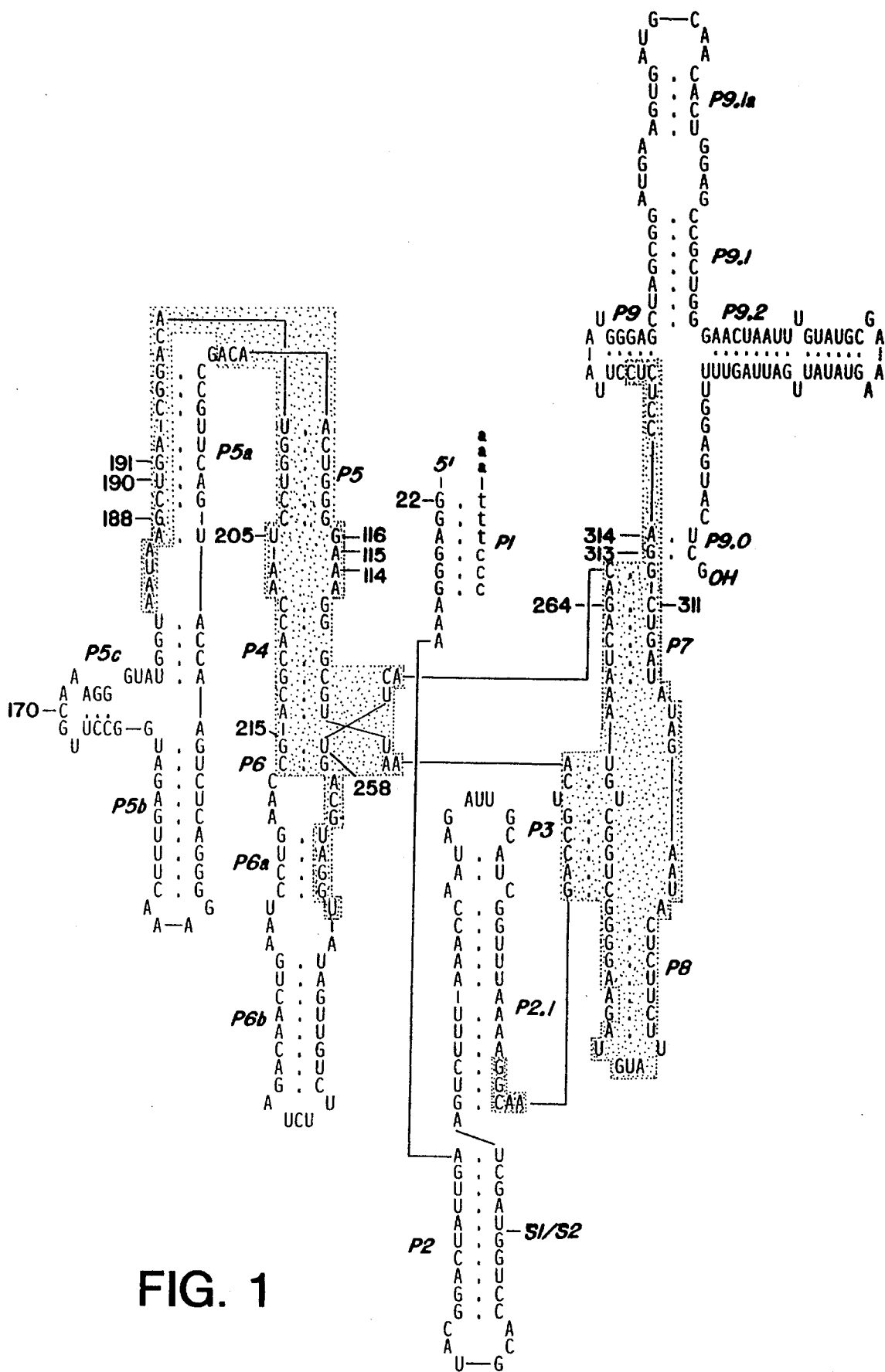
FIG. 1 illustrates the secondary structure of the wild-type Tetrahymena ribozyme (L-21 form) (SEQ ID NO 26). Paired structural elements are designated by Pi. Joining regions between paired elements i and j, referred to as J i/j, are not labeled. Nucleotide positions that were partially randomized in the initial population are indicated by shaded regions. The internal guide sequence (IGS) is shown in bold, and the DNA substrate is shown in lowercase letters. Nucleotide positions discussed in the text (see esp. Example 2) are labeled.

As used herein, the term "ribozyme" is used to describe an RNA-containing nucleic acid that is capable of functioning as an enzyme. In the present disclosure, the term "ribozyme" includes endoribonucleases and endodeoxyribonucleases of the present invention. Another term used interchangeably with ribozyme herein is "enzymatic RNA molecule", which should be understood to include ribozymes and enzymatically active portions thereof, whether derived from Tetrahymena or from other organisms or sources.

The term "enzymatic RNA molecules" includes RNA molecules which have complementarity in a substrate-binding region to a specified oligonucleotide target or substrate; it also has an enzymatic activity which is active to specifically cleave the oligonucleotide substrate. Stated in another fashion, the enzymatic RNA molecule is capable of cleaving the oligonucleotide substrate intermolecularly. This complementarity functions to allow sufficient hybridization of the enzymatic RNA molecule to the substrate oligonucleotide to allow the intermolecular cleavage of the substrate to occur. While one-hundred percent (100%) complementarity is preferred, complementarity in the range of 75–100%, or 50–100%, is also useful and contemplated by the present invention.

The term "enzymatic nucleic acid" as used herein encompasses enzymatic RNA or DNA molecules, enzymatic RNA-DNA polymers, and enzymatically active portions or derivatives thereof, although enzymatic RNA molecules are a particularly preferred class of enzymatically active molecules according to the present invention.

The term "endodeoxyribonuclease", as used herein, is an enzyme capable of cleaving a substrate comprised predominantly of DNA. The term "endoribonuclease", as used herein, is an enzyme capable of cleaving a substrate comprised predominantly of RNA.

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G may occasionally participate in base pairings. Nucleotides that normally pair up when DNA or RNA adopts a double stranded configuration may also be referred to herein as "complementary bases".

"Complementary nucleotide sequence" generally refers to a sequence of nucleotides in a single-stranded molecule of DNA or RNA that is sufficiently complementary to that on another single strand to specifically hybridize to it with consequent hydrogen bonding.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a "nucleoside". When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

"Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different sugars, or a combination of the two. A listing of exemplary analogs wherein the base has been altered is provided in Example 1; in Example 2, a nucleotide analog including an arabinose sugar is described.

"Oligonucleotide or polynucleotide" generally refers to a polymer of single- or double-stranded nucleotides. As used herein, "oligonucleotide" and its grammatical equivalents will include the full range of nucleic acids. An oligonucleotide will typically refer to a nucleic acid molecule comprised of a linear strand of ribonucleotides. The exact size will depend on many factors, which in turn depends on the ultimate conditions of use, as is well known in the art.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35°–40° C., with 37° C. being particularly preferred, as well as a pH of about 7.0–8.0, with 7.5 being particularly preferred, and further comprise the availability of cations, preferably divalent or monovalent cations, in a concentration of about 5–15 mM, with a concentration of about 10 mM being particularly preferred. "Physiologic conditions", as used herein, may optionally include the presence of polyamine or free $G_{OH}$. As noted previously, preferred conditions are described in greater detail below.

B. Enzymatic Nucleic Acid Molecules

Some genes have their coding sequences interrupted by stretches of non-coding DNA. These non-coding sequences are generally termed introns. To produce a mature transcript from these genes, the primary RNA transcript (precursor RNA) must undergo a cleavage-ligation reaction termed RNA splicing. This RNA splicing produces the mature transcript of the polypeptide coding messenger RNA (mRNA), ribosomal RNA, or transfer RNA (tRNA). Introns are grouped into four categories (groups I, II, III, and IV) based on their structure and the type of splicing reaction they undergo.

RNA molecules capable of cleaving other RNA molecules have recently been described. Such RNA-cleaving RNA molecules, which may also be referred to as ribozymes or enzymatic RNA molecules, may be chosen from group I, II, III, or IV introns, with group I and II introns being of greatest interest. Other enzymatic RNA molecules of interest herein are those formed in ribozyme motifs known in the art as "hammerhead" and "hairpin". Enzymatic RNA molecules of interest herein also include hepatitis delta virus ribozymes and RNaseP or RNaseP-like RNA.

Of particular interest to the present invention are the group I introns. Group I introns undergo an intra-molecular RNA splicing reaction leading to cyclization that does not require protein cofactors, Cech, *Science* 236: 1532–1539 (1987). (The disclosures of all references cited within this application are incorporated by reference herein, where appropriate.)

The group I introns, including the intron isolated from the large ribosomal RNA precursor of *Tetrahymena thermophila*, catalyze a sequence-specific phosphoester transfer reaction involving RNA substrates. Zaug and Cech, *Science* 229: 1060–1064 (1985); and Kay and Inoue, *Nature* 327: 343–346 (1987). This sequence-specific phosphoester transfer reaction leads to the removal of the group I intron from the precursor RNA and to ligation of two exons in a process known as RNA splicing. The splicing reaction catalyzed by group I introns proceeds via a two-step transesterification mechanism. The details of this reaction have been reviewed by Cech, *Science* 236: 1532–1539 (1987).

The splicing reaction of group I introns is initiated by the binding of guanosine or a guanosine nucleotide to a site within the group I intron structure. Attack at the 5' splice site by the 3'-hydroxyl group of guanosine results in the covalent linkage of guanosine to the 5' end of the intervening intron sequence. This reaction generates a new 3'-hydroxyl group on the uridine at the 3' terminus of the 5' exon. The 5' exon subsequently attacks the 3' splice site, yielding spliced exons and the full-length linear form of the group I intron.

The linear group I intron usually cyclizes following splicing. Cyclization occurs via a third transesterification reaction, involving attack of the 3'-terminal guanosine at an interval site near the 5' end of the intron. The group I introns also undergo a sequence-specific hydrolysis reaction at the splice site sequences as described by Inoue et al., *J. Mol. Biol.* 189: 143–165 (1986). This activity has been used to cleave RNA substrates in a sequence-specific manner by Zaug et al., *Nature* 324: 429–433 (1986).

The structure of group I introns has been reviewed by J. Burke, *Gene* 73: 273–294 (1988). The structure is characterized by nine base paired regions, termed P1–P9. (See, e.g., Burke et al., *Nucleic Acids Res.* 15: 7217–7221 (1987).) The folded structure of the intron is clearly important for the catalytic activity of the group I introns, as evidenced by the loss of catalytic activity under conditions where the intron is denatured. In addition, mutations that disrupt essential base-paired regions of the group I introns result in a loss of catalytic activity. Burke, *Gene* 73: 273–294 (1988). Compensatory mutations or second-site mutations that restore base-pairing in these regions also restore catalytic activity. Williamson et al., *J. Biol. Chem.* 262: 14672–14682 (1987); and Burke, *Gene* 73: 273–294 (1988).

Several different deletions that remove a large nucleotide segment from the group I introns (FIG. 1) without destroying its ability to cleave RNA have been reported. Burke, *Gene* 73: 273–294 (1988). However, attempts to combine large deletions have resulted in both active and inactive introns. Joyce et al., *Nucleic Acid Res.* 17: 7879 (1989).

FIG. 1 illustrates the secondary structure of the *Tetrahymena thermophila* pre-rRNA intron, with the recognition sequence and the core structure that is the most conserved region among group I introns shown in bold. The nomenclature used to denote various structural features is the standard nomenclature (see, e.g., Burke et al., *Nucleic Acids Pes.* 15:7217–7221 (1987). The nine conserved pairing regions, P1–P9, and the various loops are shown. The nucleotide sequence is numbered beginning at the 5' terminus of the molecule.

As illustrated in FIG. 1, the recognition site is located at nucleotide 19 to 27, the first spacer region is located at nucleotides 27 to 28 and 94 to 95, the P3[5'] region is located at nucleotides 96 to 103, the second spacer region is located at nucleotides 104 to 106, the first stem loop is located at nucleotides 107 to 214, the second stem loop is located at nucleotides 215 to 258, the third spacer region is located at nucleotides 259 to 261 and the third stem loop is located at nucleotides 262 to 314.

To date, group I introns have been shown to cleave substrates comprising either RNA, or an RNA-DNA polymer, with cleavage in the latter occurring at the RNA-DNA "junction". Zaug et al., *Science* 231: 470–475 (1986); Sugimoto et al., *Nucleic Acids Res.* 17: 355–371 (1989); and Cech, *Science* 236: 1532–1539 (1987). A DNA segment containing 5 deoxycytosines was shown not to be a cleavage substrate for the Tetrahymena IVS, a group I intron, in Zaug et al., *Science* 231: 470–475 (1986). Therefore, the identification, enhancement and modification of enzymatic RNA molecules capable of cleaving DNA—particularly under physiologic conditions, as described herein—is a remarkable and useful development.

The term "enzymatic nucleic acid", as used herein, is used to describe an RNA- and/or DNA-containing nucleic acid that is capable of functioning as an enzyme.

The term ribozyme is used to describe an RNA-containing nucleic acid that is capable of functioning as an enzyme. As used herein, the term "ribozyme" may be used interchangeably with "enzymatic RNA molecules". Both terms encompass endoribonucleases and endodeoxyribonucleases of the present invention.

An enzymatic RNA molecule of the present invention may be engineered or "evolved" from a wild-type, RNA-cleaving ribozyme via methods which tend to generate either "random" or "non-random" mutations. Examples of methods useful in generating enzymatic RNA molecules that include mutations not normally found in wild-type ribozymes include PCR (polymerase chain reaction), 3SR (self-sustained sequence replication), and site-directed mutagenesis.

Preferably, enzymatic RNA molecules produced as disclosed herein are capable of cleaving a DNA substrate. In one preferred embodiment, the DNA substrate is single-stranded, although enzymatic RNA molecules capable of cleaving "loop" RNA and DNA (i.e., nucleic acids found in stem loops and the like) and double-stranded DNA are also contemplated. In another preferred variation, an enzymatic RNA molecule of the present invention is able to cleave DNA under physiologic conditions. Many enzymatic RNA molecules of the present invention are also capable of cleaving a single-stranded RNA substrate or a modified DNA substrate containing a uracil at the cleavage site rather than a thymine, whereas various enzymatic RNA molecules show a marked preference for DNA as the substrate of choice.

An enzymatic RNA molecule of the present invention may comprise RNA, modified RNA, RNA-DNA polymer, a modified RNA-DNA polymer, a modified DNA-RNA polymer or a modified RNA-modified DNA polymer. RNA contains nucleotides comprising a ribose sugar and adenine, guanine, uracil or cytosine as the base at the 1' position. Modified RNA contains nucleotides comprising a ribose sugar and adenine, thymine, guanine or cytosine and optionally uracil as the base. An RNA-DNA polymer contains nucleotides containing a ribose sugar and nucleotides containing deoxyribose sugar and adenine, thymine and/or uracil, guanine or cytosine as the base attached to the 1' carbon of the sugar. A modified RNA-DNA polymer is comprised of modified RNA, DNA and optionally RNA (as distinguished from modified RNA). Modified DNA contains nucleotides containing a deoxyribose sugar and nucleotides containing adenine, uracil, guanine, cytosine and possibly thymine as the base. A modified DNA-RNA polymer contains modified DNA, RNA and optionally DNA. A modified RNA-modified DNA polymer contains modified RNA-modified DNA, and optionally RNA and DNA.

An enzymatic RNA molecule of the present invention is capable of cleaving DNA 3' of a predetermined base sequence. An enzymatic RNA molecule of this invention may also be characterized by a nucleotide sequence defining a recognition site that is contiguous or adjacent to the 5' terminus of the nucleotide sequence, a first spacer region located 3'-terminal to the recognition site, a P3[5'] region located 3'-terminal to the first spacer region, a second spacer region located 3'-terminal to the P3[5'] region, a first stem loop located 3'-terminal to the second spacer region, a second stem loop located 3'-terminal to the first stem loop, a third spacer region located 3-'terminal to the second stem loop, and a third stem loop located 3'-terminal to the third spacer region, the third stem loop comprising a 5' stem portion defining a P3[3'] region capable of hybridizing to the P3[5'] region.

It is also to be understood that an enzymatic RNA molecule of the present invention may comprise enzymatically active portions of a ribozyme or may comprise a ribozyme with one or more mutations, e.g., with one or more loops or spacers absent or modified, as long as such deletions, additions or modifications do not adversely impact the molecule's ability to perform as an enzyme.

The recognition site of an enzymatic RNA molecule of the present invention typically contains a sequence of at least 2 to about 8 bases, preferably about 4 to about 7 bases, which are capable of hybridizing to a complementary sequence of bases within the substrate nucleic acid giving the enzymatic RNA molecule its high sequence specificity. For example, an enzymatic RNA molecule of the present invention constructed with a recognition site base sequence of 3'-GG-GAGG-5' was able to recognize the base sequence 5'-CCCTCT-3' present within a single-stranded DNA substrate and to cleave same (see, e.g., Example 1). Similarly, an enzymatic RNA molecule with a recognition sequence of 3'-UCGCCG-5' was used to cleave the target sequence 5'-AGCGGT-3'.

This same recognition site also allows the enzymatic RNA molecule to cleave modified DNA substrates with high sequence specificity. Modification or mutation of the recognition site via well-known methods allows one to alter the sequence specificity of an enzymatic nucleic acid molecule.

For example, the method described by Joyce et al., *Nucleic Acids Research*, 17:711–712 (1989), involves excision of template (coding) strand of double-stranded DNA, reconstruction of the template strand with inclusion of mutagenic oligonucleotides, and subsequent transcription of the partially-mismatched template. This allows the introduction of defined or random mutations at any position in the molecule by including polynucleotides containing known or random nucleotide sequences at selected positions. In another example, mutations may be introduced into the endodeoxyribonuclease by substituting 5-Br dUTP for TTP in the reverse transcription reaction. 5-Br dU can pair with dG in the "wobble" position as well as dA in the standard Watson-Crick position, leading to A to G and G to A transitions. Similarly, substituting 5-Br UTP for UTP in the forward transcription reaction would lead to C to U and U to C transitions in the subsequent round of RNA synthesis.

Enzymatic nucleic acid molecules of the present invention include those with altered recognition sites. In various embodiments, these altered recognition sites confer unique sequence specificities on the enzymatic nucleic acid molecule including such recognition sites.

The exact bases present in the recognition site determine the base sequence at which cleavage will take place. Cleavage of the substrate nucleic acid occurs immediately 3' of the substrate cleavage sequence, the substrate nucleotide sequence that hybridizes to the recognition site. This cleavage leaves a 3' hydroxyl group on the substrate cleavage sequence and a 5' phosphate on the nucleotide that was originally immediately 3' of the substrate cleavage sequence in the original substrate. Cleavage can be redirected to a site of choice by changing the bases present in the recognition sequence (internal guide sequence). See Murphy et al., *Proc. Natl. Acad. Sci. USA* 86: 9218–9222 (1989).

Moreover, any combination of bases may be present in the recognition site if a polyamine is present. See, for example, Doudna et al., *Nature* 339: 519–522 (1989). Examples of useful polyamines include spermidine, putrescine or spermine. A spermidine concentration of about 5 mM was shown to be effective in particular embodiments, as further described hereinbelow, although concentrations ranging from about 0.1 mM to about 10 mM may also be useful.

The recognition site may also be provided as a separate nucleic acid, an external recognition site not covalently coupled to the rest of the endodeoxynuclease. External recognition sites may direct endoribonuclease cleavage at a specific base sequence (see, e.g., Doudna et al., *Nature* 339: 519–522 (1989)). If an external recognition site is used, the enzymatic RNA molecule used with it would probably not contain a recognition site but would tend to comprise a P3[5'] region, a second spacer region, a first stem loop, a second stem loop, a third spacer region and a third stem loop where the third stem loop comprises a 5' stem portion defining a P3[3'] region capable of hybridizing to said P3[5'] region.

Use of an enzymatic RNA molecule of the present invention with an external recognition site allows the target sequence to be altered by merely changing the external recognition site sequence. Use of a plurality of different external recognition sequences with an enzymatic RNA molecule of the present invention allows the substrate nucleic acid to be cleaved at each of the different base sequences encoded by the external recognition sequences.

First spacer regions typically contain a sequence of nucleotides of about 3 to 7, preferably about 5, bases in length. In one variation, the nucleotides making up the first spacer have the sequence 5'-NNNNA-3' (SEQ ID NO 1), where N represents the presence of any nucleotide at that position. In another variation, the first spacer region is defined by the sequence 5'-AACAA-3' (SEQ ID NO 2).

In other embodiments, the first spacer region is comprised of a nucleotide sequence defining two spacer stem loops. In one variation, the first spacer stem loop is 25 nucleotides in length, and the second spacer stem loop is 36 bases in length. In another variation, the first spacer stem loop has the base sequence 5'-AGUUACCAGGCAUGCACCUG-GUAGUCA-3, (SEQ ID NO 3), and the second spacer stem loop has the base sequence 5'-GUCUUUAAACCAAUA-GAUUGGAUCGGUUU-AAAAGGC-3, (SEQ ID NO 4).

As noted previously, the foregoing descriptions of loop and spacer regions is exemplary and is not to be construed as limiting the disclosed invention(s).

A stem loop is a secondary structure formed by a nucleotide sequence that has "folded over on itself". A stem loop comprises a 5' nucleotide sequence portion, designated a 5' paring segment (P[5']) that is capable of hybridizing to a nucleotide sequence located 3' of the P[5'] and is designated the 3' pairing segment (P[3']). In a stem loop, the P[5'] and P[3'] are connected by a nucleotide sequence called a loop. The P[5'] and P[3'] hybridize and form a nucleic acid duplex. The nucleic acid duplex formed by the P[5'] and P[3'] does not have to be a perfect duplex and may contain stretches of nucleotides that are either unpaired or paired to a sequence outside the stem loop.

In various alternative embodiments, an enzymatic RNA molecule of the present invention has an enhanced or optimized ability to cleave nucleic acid substrates, preferably DNA substrates.

As those of skill in the art will appreciate, the rate of an enzyme-catalyzed reaction varies depending upon the substrate and enzyme concentrations and, in general, levels off at high substrate or enzyme concentrations. Taking such effects into account, the kinetics of an enzyme-catalyzed reaction may be described in the following terms, which define the reaction.

The enhanced or optimized ability of an enzymatic RNA molecule of the present invention to cleave a DNA substrate may be determined in a cleavage reaction with varying amounts of labeled DNA substrate in the presence of enzymatic RNA molecule as described in Examples 1 and 2. The ability to cleave the substrate is generally defined by the catalytic rate ($k_{cat}$) divided by the Michaelis constant ($K_M$). The symbol $k_{cat}$ represents the maximal velocity of an enzyme reaction when the substrate approaches a saturation value. $K_M$ represents the substrate concentration at which the reaction rate is one-half maximal. Values for $K_M$ and $k_{cat}$ are determined in this invention by experiments in which the substrate concentration [S] is in excess over enzymatic RNA molecule concentration [E]. Initial rates of reaction ($v_o$) over a range of substrate concentrations were estimated from the initial linear phase, generally the first 5% or less of the reaction. Typically eight data points were fit by a least squares method to a theoretical line given by the equation: $v=-K_M(v_o/[S])+V_{max}$. Thus, $k_{cat}$ and $K_M$ were determined by the initial rate of reaction, $v_o$, and the DNA substrate concentration [S].

In various alternative embodiments, an enzymatic RNA molecule of the present invention has an enhanced or optimized ability to cleave nucleic acid substrates, preferably DNA substrates. In preferred embodiments, the enhanced or optimized ability of an enzymatic RNA molecule to cleave DNA substrates shows about a 10- to $10^9$-fold improvement. In more preferred embodiments, an enzymatic RNA molecule of the present invention is able to cleave DNA substrates at a rate that is about $10^3$- to $10^7$-fold better than wild type enzymes. In even more preferred embodiments, the enhanced or optimized ability to cleave DNA substrates is expressed as a $10^4$- to $10^6$-fold improvement over the wild type. One skilled in the art will appreciate that the enhanced or optimized ability of an enzymatic RNA molecule to cleave nucleic acid substrates may vary depending upon the selection constraints applied during the in vitro evolution procedure of the invention.

Enzymatic RNA molecules of the present invention may also be characterized as displaying a $K_M$ value that is improved at least two-fold over the wild type. As noted above, $K_M$ represents the substrate concentration at which the reaction rate is one-half maximal; thus, an improved $K_M$ indicates an improvement in substrate processing. In various embodiments, enzymatic RNA molecules of the present invention have a $K_M$ that is 10- to 20-fold better than that of the wild type. In still other embodiments, enzymatic RNA molecules of the present invention have a $K_M$ that is 30- to 40-fold improved over the wild type. In various other embodiments, enzymatic RNA molecules of the present invention have a $K_M$ that is 40- to 50-fold improved over the wild type.

One skilled in the art will understand that the enhanced or optimized ability of an enzymatic RNA molecule to process nucleic acid (e.g. DNA) substrates may vary depending upon the selection constraints applied during the in vitro evolution procedure of the invention and may include a reduction of the DNA concentration to favor enzymatic RNA molecules with improved substrate processing ability.

In other embodiments, an enzymatic RNA molecule of the present invention has an enhanced or optimized ability to bind a nucleic acid substrate. The ability of an enzymatic RNA molecule to bind a DNA substrate is defined by the dissociation constant ($K_D$). The $K_D$ is an equilibrium constant describing the dissociation of the enzymatic RNA molecule:substrate complex into its individual components. The $K_D$ constant as understood in the context of this invention is determined by a gel shift analysis to determine the percent enzymatic RNA molecule bound to the DNA product, as described in Example 2. A binding curve is generated by plotting the percent of product bound to enzymatic RNA molecule over a range of enzymatic RNA molecule concentration. The $K_D$ is determined by fitting the data to a theoretical binding curve using the least squares method. Typically, the enzymatic RNA molecule concentration [E] vastly exceeds the product; therefore, the theoretical binding curve can be represented by the equation: % bound= $[E]/([E]+K_D)$, where $K_D=[E]$ when half of the total product is bound to the enzymatic RNA molecule.

An enzymatic RNA molecule of the present invention preferably binds nucleic acid substrate with a $K_D$ which is an improvement over wild type ribozymes. For example, an enzymatic RNA molecule of the present invention preferably binds DNA with a $K_D$ having a value less than 30 µM. In preferred embodiments, enzymatic RNA molecules bind DNA with a $K_D$ having a value less than about 10 µM. In more preferred embodiments, the $K_D$ of a DNA-binding enzymatic RNA molecule is less than about 1 µM. In an even more preferred embodiment, the $K_D$ of a DNA-binding enzymatic RNA molecule is less than about 50 nM, more preferably less than about 25 nM, and even more preferably less than about 10 nM. Especially preferred enzymatic RNA molecules bind DNA substrate with a $K_D$ of 5 nM or less, e.g., with a $K_D$ of about 0.1–5 nM.

Alternatively, the enhanced or optimized ability of an enzymatic RNA molecule to bind DNA substrates may be expressed as a five-fold or greater improvement over the wild type. In various embodiments, the enhanced or optimized ability of an enzymatic RNA molecule to bind DNA substrates comprises a 10- to $10^2$-fold improvement. In other embodiments, the enhanced or optimized ability of an enzymatic RNA molecule to bind DNA substrates may be expressed as a $10^2$- to $10^3$-fold improvement over the wild type. In still other embodiments, binding (i.e. $K_D$) of enzymatic RNA molecules of the present invention is $10^4$-fold improved over the wild type, or better. One skilled in the art will understand that the enhanced or optimized ability of an enzymatic RNA molecule to bind DNA substrates may vary depending upon the selection constraints applied during the in vitro evolution procedure of the invention and may include a reduction of the DNA concentration to favor enzymatic RNA molecules with improved substrate binding affinity.

In other preferred embodiments, enzymatic RNA molecules of the present invention preferably bind RNA substrate with a $K_D$ which is an improvement over wild type ribozymes. For example, an enzymatic RNA molecule of the present invention preferably binds RNA with a $K_D$ having a value less than 1.5 nM. In preferred embodiments, enzymatic RNA molecules bind RNA with a $K_D$ having a value less than about 1.0 nM. In even more preferred embodiments, enzymatic RNA molecules of the present invention bind RNA with a $K_D$ of about 0.5 nM or less.

In another variation, an enzymatic RNA molecule of the present invention has an enhanced or optimized substrate turnover rate. The enhanced or optimized substrate turnover rate may be determined in single-turnover kinetic experiments with the enzymatic RNA molecule in excess of the substrate as described in Example 2. Initial rates ($k_{obs}$) were obtained using no more than the first 5% of the reaction. Given that $k_{cat}/K_M=k_{obs}/[E]$, each $k_{obs}$ value, obtained at different enzymatic RNA molecule concentrations, provided an estimate of $k_{cat}/K_M$. Generally, eight or more measurements of $k_{cat}/K_M$ were obtained. The value of $k_{cat}$ in the presence of limited substrate indicates the substrate turnover number rate and is expressed in the number of catalytic cycles that are completed by the enzyme per unit of time under the assay conditions.

Alternatively, the enhanced or optimized substrate turnover rate of an enzymatic RNA molecule may be described as being improved about 2-fold over the wild type. In other embodiments, the enhanced or optimized substrate turnover rate of an enzymatic RNA molecule shows at least a 5- to 25-fold improvement over the wild type. In still other embodiments, the enhanced or optimized substrate turnover rate of an enzymatic RNA molecule of the present invention is about 30–40 times greater than that of the wild type. In preferred embodiments, the substrate turnover rate is at least about 50 times greater than in the wild type. One skilled in the art will understand that the enhanced or optimized substrate turnover rate of an enzymatic RNA molecule of the present invention may vary depending upon the selection constraints applied during the in vitro evolution procedure of the invention and may include a reduction of the reaction time to favor enzymatic RNA molecules with improved substrate turnover rates.

In other embodiments, an enzymatic RNA molecule of the present invention is capable of functioning efficiently over a wide range of temperatures. In yet another variation, an enzymatic RNA molecule of the present invention is capable of functioning efficiently over a wide range of pH.

In various alternative embodiments, an enzymatic RNA molecule of the present invention is capable of functioning efficiently with or without added polyamine. In another variation, an enzymatic RNA molecule of the present invention is capable of functioning efficiently in the presence or absence of $Mg^{2+}$.

Alternatively, an enzymatic RNA molecule of the present invention is capable of functioning efficiently in the presence or absence of divalent cations other than $Mg^{2+}$. Other suitable divalent cations may be selected from the group comprised of $Mn^{2+}$, $Zn^{2+}$, or $Ca^{2+}$. It is anticipated that cation concentrations similar to those described above for $Mg^{2+}$ will be useful as disclosed herein.

Optionally, monovalent cations may also be present as "alternatives" for the use of divalent cations. For example, monovalent cations such as sodium ($Na^+$) or potassium ($K^+$) may be present, either as dissociated ions or in the form of dissociable compounds such as NaCl or KCl. In one embodiment, a monovalent cation is present in a concentration ranging from about 0–200 mM. In other embodiments, monovalent cations are present in a concentration ranging from about 2–100 mM. Alternatively, the concentration of monovalent cations ranges from about 2 mM–50 mM. In other embodiments, the concentration ranges from about 2 mM–25 mM, with a concentration of about 2 mM–15 mM being preferred.

In various embodiments, an enzymatic RNA molecule of the present invention optionally includes a 3' hydroxyl of G (i.e. guanosine, or one of its 5'-phosphorylated forms), which functions as a nucleophile—i.e., it "attacks" substrate molecules, usually at a phosphodiester bond. For example, in the L-21 ribozyme derived from the group I intron of *Tetrahymena thermophila*, the G264-C311 base pair—which is known as the "G-site"—binds the G substrate. (See, e.g., Wang and Cech, *Science* 256: 526–529 (1992).)

Alternatively, in other embodiments, wherein an enzymatic RNA molecule of the present invention lacks a 3' terminal $G_{OH}$, the $G_{OH}$ may be supplied as a free (i.e., unattached) attacking group. In such embodiments, an enzymatic RNA molecule is able to "attack" multiple substrates in sequential fashion. In either case, the term "enzymatic RNA molecules" as used in the present disclosure includes enzymatic RNA molecule including, as well as those lacking, a 3' $G_{OH}$.

In various embodiments, an enzymatic RNA molecule of the present invention may combine one or more modifications or mutations including additions, deletions, and substitutions. In alternative embodiments, such mutations or modifications may be generated using methods which produce random or specific mutations or modifications. These mutations may change the length of, or alter the nucleotide sequence of, a stem loop, the P3[5'], the P3[3']region, a spacer region or the recognition sequence. One or more mutations within one catalytically active enzymatic RNA molecule may be combined with the mutation(s) within a second catalytically active enzymatic RNA molecule to produce a new enzymatic RNA molecule containing the mutations of both molecules.

In other preferred embodiments, an enzymatic RNA molecule of the present invention may have random or defined mutations introduced into it using a variety of methods well known to those skilled in the art. For example, the method described by Joyce et al., *Nucleic Acids Res.* 17: 711–712 (1989), involves excision of a template (coding) strand of a double-stranded DNA, reconstruction of the template strand with inclusion of mutagenic oligonucleotides, and subsequent transcription of the partially-mismatched template. This allows the introduction of defined or random mutations at any position in the molecule by including polynucleotides containing known or random nucleotide sequences at selected positions.

Alternatively, mutations may be introduced into an enzymatic RNA molecule by substituting 5-Br dUTP for TTP in the reverse transcription reaction. 5-Br dU can pair with dG in the "wobble" position as well as dA in the standard Watson-Crick position, leading to A → G and G → A transitions. Similarly, substituting 5-Br UTP for UTP in the forward transcription reaction would lead to C → U and U → C transitions in the subsequent round of RNA synthesis, as described above.

Enzymatic RNA molecules of the present invention may be of varying lengths and folding patterns, as appropriate, depending on the type and function of the molecule. For example, enzymatic RNA molecules derived from group I introns (e.g., Tetrahymena-derived ribozymes) may be about 413 or more nucleotides in length, although a length not exceeding 413 nucleotides is preferred, to avoid limiting the therapeutic usefulness of molecules by making them too large or unwieldy. In various therapeutic applications, enzymatic RNA molecules of the present invention comprise the enzymatically active portions of ribozymes. In various embodiments, enzymatic RNA molecules of the present invention comprise fewer than 400 nucleotides, fewer than 300 nucleotides, fewer than 200 nucleotides, or fewer than 100 nucleotides.

In other therapeutic applications, enzymatic RNA molecules such as "hammerhead" ribozymes are preferably no more than about 50 nucleotides in length, with a length of 30–40 nucleotides being particularly preferred. Even more preferred are hammerhead ribozymes of about 31–36 nucleotides in length.

Moreover, if one intends to synthesize molecules for use as disclosed herein, the larger the enzymatic nucleic acid molecule is, the more difficult it is to synthesize. Those of skill in the art will certainly appreciate these design constraints.

Various preferred methods of modifying ribozymes and other enzymatic RNA molecules, ribonucleases, and deoxyribonucleases of the present invention are further described in Examples 1–4 hereinbelow.

C. Methods of Cleaving Nucleic Acid Molecules

The present invention also describes useful methods for cleaving any single-stranded, looped, partially or fully double-stranded nucleic acid; the majority of these methods employ the novel enzymatically active nucleic acid molecules of the present invention. In various embodiments, the single-stranded nucleic acid substrate comprises single-stranded DNA, modified DNA, RNA and modified RNA. The nucleic acid substrate must only be single-stranded at or near the substrate cleavage sequence so that an enzymatic nucleic acid molecule of the present invention can hybridize to the substrate cleavage sequence by virtue of the enzyme's recognition sequence.

A nucleic acid substrate that can be cleaved by a method of this invention may be chemically synthesized or enzymatically produced, or it may be isolated from various sources such as phages, viruses, prokaryotic cells, or eukaryotic cells, including animal cells, plant cells, eukaryotic cells, yeast cells and bacterial cells. Chemically synthesized single-stranded nucleic acids are commercially available from many sources including, without limitation, Research Genetics (Huntsville, Ala.).

DNA substrates may also be synthesized using an Applied Biosystems (Foster City, Calif.) oligonucleotide synthesizer according to the manufacture's instructions. Single-stranded phages such as the M13 cloning vectors described by Messing et al., *PNAS USA* 74: 3642–3646 (1977), and Yanisch-Perron et al., *Gene* 33: 103–119 (1985) are also sources of DNA substrates. Bacterial cells containing single-stranded phages would also be a ready source of suitable single-stranded DNA. Viruses that are either single-stranded DNA viruses such as the parvoviruses or are partially single-stranded DNA viruses such as the hepatitis virus would provide single-stranded DNA that could be cleaved by a method of the present invention.

Single-stranded RNA cleavable by a method of the present invention could be provided by any of the RNA viruses such as the picornaviruses, togaviruses, orthomyxoviruses, paramyxoviruses, rhabdoviruses, coronaviruses, arenaviruses or retroviruses. As noted previously, a wide variety of prokaryotic and eukaryotic cells may also be excellent sources of suitable nucleic acid substrates.

The methods of this invention may be used on single-stranded nucleic acids or single-stranded portions of double-stranded DNA (dsDNA) that are present inside a cell, including eucaryotic, procaryotic, plant, animal, yeast or bacterial cells. Under these conditions an enzymatic nucleic acid molecule (e.g., an enzymatic RNA molecule or ribozyme) of the present invention could act as an anti-viral agent or a regulator of gene expression. Examples of such uses of enzymatic RNA molecules of the present invention are described in subsection F hereinbelow.

In the majority of methods of the present invention, cleavage of single-stranded DNA occurs at the 3'-terminus of a predetermined base sequence. This predetermined base sequence or substrate cleavage sequence typically contains from about 2 to about 10 nucleotides. In a preferred variation, the predetermined base or substrate cleavage sequence comprises about 2 to about 6 nucleotides. In other preferred embodiments, an enzymatic RNA molecule of the present invention is able to recognize nucleotides either upstream, or upstream and downstream of the cleavage site. In various embodiments, an enzymatic RNA molecule is able to recognize about 2–10 nucleotides upstream of the cleavage site; in other embodiments, an enzymatic RNA molecule is able to recognize about 2–10 nucleotides upstream and about 2–10 nucleotides downstream of the cleavage site. Other preferred embodiments contemplate an enzymatic RNA molecule that is capable of recognizing a nucleotide sequence up to about 30 nucleotides in length, with a length up to about 20 nucleotides being preferred.

The within-disclosed methods allow cleavage at any nucleotide sequence by altering the nucleotide sequence of the recognition site of the enzymatic RNA molecule. This allows cleavage of single-stranded DNA in the absence of a restriction endonuclease site at that position.

Cleavage at the 3'-terminus of a predetermined base sequence produces a single-stranded DNA containing the substrate cleavage sequence, with a 3'-terminal hydroxyl group. In addition, the cleavage joins the remainder of the original single-stranded DNA substrate with the enzymatic RNA molecule. This cleavage reaction and products produced from this cleavage reaction are analogous to the cleavage reaction and cleavage products produced by the Tetrahymena ribozyme described by Zaug and Cech, *Science* 231: 470–475 (1986).

An enzymatic RNA molecule of the present invention may be separated from the remainder of the single-stranded DNA substrate by site-specific hydrolysis at the phosphodiester bond following the 3'-terminal guanosine of the enzymatic RNA molecule, similar to the site-specific cleavage at this position described for the ribozyme acting on RNA by Inoue et al., *J. Mol. Biol.* 189: 143–165 (1986). Separation of the enzymatic RNA molecule from the substrate allows the enzymatic RNA molecule to carry out another cleavage reaction.

Generally, the nucleic acid substrate is treated under appropriate nucleic acid cleaving conditions—preferably, physiologic conditions—with an effective amount of an enzymatic RNA molecule of the present invention. If the nucleic acid substrate comprises DNA, preferably, cleaving conditions include the presence of $MgCl_2$ at a concentration of about 2–100 mM. Typically, the DNA cleaving conditions include $MgCl_2$ at a concentration of about 2 mM to about 50 mM. Preferably, $MgCl_2$ is present at a concentration of about 5 mM to about 25 mM. More preferably, $MgCl_2$ is present at a concentration of about 5 mM to about 15 mM, with a concentration of magnesium ion of about 10 mM being particularly preferred.

An effective amount of an enzymatic RNA molecule is the amount required to cleave a predetermined base sequence present within the single-stranded DNA. Preferably, the enzymatic RNA molecule is present at a molar ratio of RNA molecule to substrate cleavage sites of 1 to 20. This ratio may vary depending on the length of treating and efficiency of the particular enzymatic RNA molecule under the particular DNA cleavage conditions employed.

Treating typically involves admixing, in aqueous solution, the DNA-containing substrate, the enzyme and the $MgCl_2$ to form a DNA cleavage admixture, and then maintaining the admixture thus formed under DNA cleaving conditions for a time period sufficient for the enzymatic RNA molecule to cleave the DNA substrate at any of the predetermined nucleotide sequences present in the DNA.

In one embodiment of the present invention, the amount of time necessary for the enzymatic RNA molecule to cleave the single-stranded DNA has been predetermined. The amount of time is from about 5 minutes to about 24 hours and will vary depending upon the concentration of the reactants, and the temperature of the reaction. Usually, this time period is from about 30 minutes to about 4 hours such that the enzymatic RNA molecule cleaves the single-stranded DNA at any of the predetermined nucleotide sequences present.

The invention further contemplates that the DNA cleaving conditions include the presence of $MgCl_2$ at a concentration of about 2–100 mM. Typically, the DNA cleaving conditions include $MgCl_2$ at a concentration of about 2 mM to about 50 mM. Preferably, $MgCl_2$ is present at a concentration of about 5 mM to about 25 mM. More preferably, $MgCl_2$ is present at a concentration of about 5 mM to about 15 mM, with a concentration of about 10 mM being particularly preferred.

The optimal $MgCl_2$ concentration to include in the DNA cleaving conditions can be easily determined by determining the amount of single-stranded DNA cleaved at a given $MgCl_2$ concentration. One skilled in the art will understand that the optimal $MgCl_2$ concentration may vary depending on the particular enzymatic RNA molecule employed.

The present invention further contemplates that the DNA cleaving conditions are at from about pH 6.0 to about pH 9.0. In one preferred embodiment, the pH ranges from about pH 6.5 to pH 8.0. In another preferred embodiment, the pH emulates physiological conditions, i.e., the pH is about 7.0–7.8, with a pH of about 7.5 being particularly preferred.

One skilled in the art will appreciate that the methods of the present invention will work over a wide pH range so long as the pH used for DNA cleaving is such that the enzymatic RNA molecule is able to remain in an active conformation. An enzymatic RNA molecule in an active conformation is easily detected by its ability to cleave single-stranded DNA at a predetermined nucleotide sequence.

In various embodiments, the DNA cleaving conditions also include a variety of temperature ranges; as noted previously, temperature ranges consistent with physiological conditions are especially preferred. In one embodiment, the temperature ranges from about 15° C. to about 60° C. In another variation, the DNA cleaving conditions are from about 30° C. to about 56° C. The temperature of the DNA cleaving conditions are constrained only by the desired cleavage rate and the stability of that particular enzymatic RNA molecule at that particular temperature. In yet another variation, DNA cleavage conditions include a temperature from about 35° C. to about 50° C. In a preferred embodiment, DNA cleavage conditions comprise a temperature range of about 37° C. to about 42° C.

In various other methods, the present invention contemplates DNA cleaving conditions including the presence of a polyamine. Polyamines useful for practicing the present invention include spermidine, putrescine, spermine and the like. In one preferred variation, the polyamine is spermidine and it is present at a concentration of about 0.01 mM to about 15 mM. In another variation, the polyamine is present at a concentration of about 1 mM to about 10 mM. DNA cleavage conditions may also include the presence of polyamine at a concentration of about 2 mM to about 5 mM. In various preferred embodiments, the polyamine is spermidine.

D. Methods of Mutagenizing Enzymatic RNA Molecules

The present invention also contemplates methods of producing nucleic acid molecules having a predetermined activity. In one preferred embodiment, the nucleic acid molecule is an enzymatic RNA molecule. In another variation, the desired activity is a catalytic activity.

In one embodiment, the present invention contemplates methods of synthesizing enzymatic RNA molecules which may then be "engineered" to catalyze a specific or predetermined reaction. Methods of preparing enzymatic RNA molecules are described herein; see, e.g., Examples 1, 2 and 4 hereinbelow. In other embodiments, an enzymatic RNA molecule of the present invention may be engineered to bind small molecules or ligands, such as adenosine triphosphate (ATP). (See, e.g., Sassanfar, et al., *Nature* 364: 550–553 (1993).)

In another embodiment, the present invention contemplates that a population of enzymatic RNA molecules may be subjected to mutagenizing conditions to produce a diverse population of mutant enzymatic RNA molecules or ribozymes. Thereafter, enzymatic RNA molecules having desired characteristics are selected and/or separated from the population.

Alternatively, mutations may be introduced in the enzymatic RNA molecule by altering the length of the recognition site (internal guide sequence) of the enzymatic RNA molecule. The recognition site of the enzymatic RNA molecule hybridizes with a complementary sequence of bases within the substrate nucleic acid sequence. Methods of altering the length of the recognition site are known in the art and include PCR, for example; useful techniques are described further in the Examples.

Alteration of the length of the recognition site of the enzymatic RNA molecule which retains the ability to hybridize with the complementary sequence of bases within the substrate nucleic acid sequence may have a desirable effect on the binding specificity of the enzymatic RNA molecule. For example, an increase in the length of the recognition site may increase binding specificity between the enzymatic RNA molecule and the complementary base sequences of the nucleic acid. In addition, an increase in the length of the recognition site may also increase the affinity with which it binds to the nucleic acid substrate. In various embodiments, these altered recognition sites in the enzymatic RNA molecule confer increased binding specificity and affinity between the enzymatic RNA molecule and its nucleic acid substrate.

One of skill in the art would realize that the enzymatic RNA molecules of this invention can be altered at any nucleotide sequence, such as the recognition site, by various methods disclosed herein, including PCR and 3SR. Additional nucleotides can be added to the 5' end of the enzymatic RNA molecule by including the additional nucleotides in the primer used to introduce the T7 promoter binding site.

The additional nucleotides would be included in the primer between the T7 promoter sequence and the nucleotide sequences which hybridize to the enzymatic RNA molecule at the 5' end.

Enzymatic RNA molecules of the present invention may also be prepared or engineered in a more non-random fashion via use of methods such as site-directed mutagenesis. For example, site-directed mutagenesis may be carried out essentially as described in Morinaga, et al., *Biotechnology* 2: 636 (1984), which is incorporated herein by reference. Site-directed mutagenesis techniques are described in greater detail hereinbelow; see, e.g., Example 1.

In various embodiments, the population of group I nucleic acids is made up of at least 2 group I nucleic acids. In one variation, group I nucleic acids are nucleic acid molecules having a nucleic acid sequence defining a recognition site that is contiguous or adjacent to the 5'-terminus of the nucleotide sequence, a first spacer region located 3'-terminal to the recognition site, a P3[5'] region located 3'-terminal to the first spacer region, a second spacer region located 3'-terminal to the P3[5'] region, a first stem loop located 3'-terminal to the second spacer region, a second stem loop located 3'-terminal to the first stem loop, a third spacer region located 3'-terminal to the second stem loop, and a third stem loop located 3'-terminal to the third spacer region, the third stem loop comprising a 5' stem portion defining a P3[3'] region capable of hybridizing to the P3[5'] region. Other characteristics of enzymatic RNA molecules produced according to the presently-disclosed methods are described in Section B above and in the Examples that follow.

In other embodiments, mutagenizing conditions include conditions that introduce either defined or random nucleotide substitutions within an enzymatic RNA molecule. Examples of typical mutagenizing conditions include conditions disclosed in other parts of this specification and the methods described by Joyce et al., *Nucl. Acids Res.* 17: 711–722 (1989); Joyce, *Gene* 82: 83–87 (1989); and Beaudry and Joyce, *Science* 257: 635–41 (1992).

In still other embodiments, a diverse population of mutant enzymatic nucleic acid molecules of the present invention is one that contains at least 2 nucleic acid molecules that do not have the exact same nucleotide sequence. In other variations, from such a diverse population, an enzymatic RNA molecule or other enzymatic nucleic acid having a predetermined activity is then selected on the basis of its ability to perform the predetermined activity. In various embodiments, the predetermined activity comprises, without limitation, enhance catalytic activity, decreased $K_M$, enhanced substrate binding ability, altered substrate specificity, and the like.

Parameters which may be considered aspects of enzyme performance include catalytic activity or capacity, substrate binding ability, enzyme turnover rate, enzyme sensitivity to feedback mechanisms, and the like. In certain aspects, substrate specificity may be considered an aspect of enzyme performance, particularly in situations in which an enzyme is able to recognize and bind two or more competing substrates, each of which affects the enzymes' performance with respect to the other substrate(s).

Substrate specificity, as used herein, may refer to the specificity of an enzymatic nucleic acid molecule as described herein for a particular substrate, such as one comprising RNA only, DNA only, or a composite of both. Substrate specificity also refers to whether an enzymatic nucleic acid molecule of the present invention preferentially binds a single-stranded nucleic acid substrate, a double-stranded nucleic substrate, or a nucleic acid molecule having both single-stranded and double-stranded regions (such as nucleic acid molecules with "loops"). In the case of the latter type of substrate, an enzymatic nucleic acid molecule of the present invention may preferentially bind to a particular region of such a composite substrate.

Substrate specificity may also include sequence specificity; i.e., an enzymatic nucleic acid molecule of the present invention may "recognize" and bind to a nucleic acid substrate having a particular nucleic acid sequence. For example, if the substrate recognition site of an enzymatic nucleic acid molecule of the present invention will only bind to nucleic acid substrate molecules having a series of six adenine residues in a row, then the enzymatic nucleic acid molecule will tend not to recognize or bind nucleic acid substrate molecules lacking such a sequence. In various embodiments, selecting includes any means of physically separating the mutant enzymatic nucleic acids having a predetermined activity from the diverse population of mutant enzymatic nucleic acids. Often, selecting comprises separation by size, by the presence of a catalytic activity, or by hybridizing the mutant nucleic acid to another nucleic acid that is either in solution or attached to a solid matrix.

In various embodiments, the predetermined activity is such that the mutant enzymatic nucleic acid having the predetermined activity becomes labelled in some fashion by virtue of the activity. For example, the predetermined activity may be an enzymatic RNA molecule activity whereby the activity of the mutant enzymatic nucleic acid upon its substrate causes the mutant enzymatic nucleic acid to become covalently linked to it. The mutant enzymatic nucleic acid is then selected by virtue of the covalent linkage.

In other embodiments, selecting a mutant enzymatic nucleic acid having a predetermined activity includes amplification of the mutant enzymatic nucleic acid (see, e.g., Joyce, *Gene* 82: 83–87 (1989); Beaudry and Joyce, *Science* 257: 635–41 (1992)).

E. Compositions

The invention also contemplates compositions containing one or more types or populations of enzymatic RNA molecules of the present invention; e.g., different types or populations may recognize and cleave different nucleotide sequences. Compositions may further include a DNA-containing substrate. Compositions according to the present invention may further comprise magnesium ion or other divalent or monovalent cations, as discussed in section B above.

Preferably, the enzymatic RNA molecule is present at a concentration of about 0.05 µM to about 2 µM. Typically, the enzymatic RNA molecule is present at a concentration ratio of enzymatic RNA molecule to single-stranded DNA substrate of from about 1:5 to about 1:50. More preferably, the enzymatic RNA molecule is present in the composition at a concentration of about 0.1 µM to about 1 µM. Even more preferably, compositions contain the enzymatic RNA molecule at a concentration of about 0.1 µM to about 0.5 µM. Preferably, single-stranded DNA substrate is present in the composition at a concentration of about 0.5 µM to about 1000 µM. One skilled in the art will understand that there are many sources of single-stranded DNA including synthetic DNA, phage DNA, "loop" DNA, denatured double-stranded DNA, viral DNA and cellular.

Magnesium ion may also be present in the composition, at a concentration of about 2–100 mM. More preferably, the magnesium ion is present in the composition at a concentration of about 2 mM to about 50 mM. Preferably, magnesium ion is present at a concentration of about 5 mM to about 15 mM, with a concentration of about 10 mM being particularly preferred. One skilled in the art will understand that the magnesium ion concentration is only constrained by the limits of solubility of magnesium in aqueous solution and a desire to have the enzymatic RNA molecule present in the same composition in an active conformation.

The invention also contemplates compositions containing an enzymatic RNA molecule of the present invention, single-stranded DNA, magnesium ion in concentrations as described hereinabove, and a polyamine. Preferably, the polyamine is spermidine, putrescine, or spermine. More preferably, the polyamine is spermidine and is present at a concentration of about 2 mM to about 10 mM. The invention further contemplates compositions containing an enzymatic RNA molecule of the present invention, single-stranded DNA, magnesium ion at a concentration of greater than 20 millimolar, a second single-stranded DNA molecule ending in a 3'-terminal hydroxyl, and a third single-stranded DNA molecule having a guanine nucleotide at its 5'-terminal end.

Also contemplated by the present invention are compositions containing an enzymatic RNA molecule of the present invention, singled-stranded DNA and magnesium ion at a concentration of greater than about 2 millimolar, wherein said single-stranded DNA is greater in length than the recognition site present on the enzymatic RNA molecule.

F. Methods of Using Enzymatic RNA Molecules

The methods of this invention may be used to cleave single-stranded nucleic acids or single-stranded portions of double-stranded nucleic acids, whether those nucleic acids are present in an in vitro or ex vivo system, or whether they are present inside a cell, whether those cells are eucaryotic, procaryotic, plant, animal, yeast or bacterial cells.

For example, if the double-stranded nucleic acid is dsDNA, methods of using the enzymatic RNA molecules described herein may be used to cleave single-stranded portions of dsDNA, e.g., "looped" DNA or single-stranded segments of DNA that are accessible during transcription or translation.

It is also contemplated that enzymatic RNA molecules of the present invention, and the within-disclosed methods of using same, may be used to cleave dsDNA. In one embodiment, cleavage of dsDNA may be accomplished using coupled or paired enzymatic RNA molecules, wherein one member of the pair recognizes and cleaves one target nucleotide sequence, while its "partner" recognizes and cleaves the complementary target nucleotide sequence. In preferred embodiments, however, the enzymatic RNA molecules and methods of this invention are used to cleave single-stranded nucleic acids or single-stranded portions of double-stranded nucleic acids, in vivo, in vitro or ex vivo. Therefore, in one embodiment, an enzymatic RNA molecule (ribozyme) of the present invention may be useful as an anti-viral agent or a regulator of gene expression.

For example, an enzymatic RNA molecule of the present invention may be used to treat a virally-caused disease by administering to a patient in need of treatment an enzymatic RNA molecule which cleaves viral nucleic acid or virus-encoded nucleic acid. Viruses whose nucleic acids or encoded nucleic acids may be susceptible to cleavage by an enzymatic RNA molecule of the present invention include, for example, papillomavirus, EBV, HSV, HBV, HIV (e.g., HIV-1, HIV-2), T-cell leukemia virus (e.g., HTLV-1, HTLV-2), HCV, CMV, influenza virus, and picornavirus.

In a related aspect of the invention, an enzymatic RNA of the present invention may be used to treat virally-cause diseases in animals, such as feline immunodeficiency virus (FIV), feline leukemia virus (FLV), simian immunodeficiency virus (SIV), bovine leukemia virus (BLV), and simian leukemia virus (e.g., STLV). Useful enzymatic RNA molecules of the present invention may be selected on the basis of their ability to target a selected region (or regions) of a viral genome. In various embodiments, such enzymatic RNA molecules are able to cleave the target nucleic acid sequence or segment in a manner which inhibits transcription, translation, or expression of the nucleic acid sequence. Target nucleic acid segments are selected so that inhibition of transcription, translation or expression will have maximal effect. For example, targeting the enzymatic RNA molecules of the present invention to nucleic acid sequences involved in protein synthesis, genomic replication, or packaging into virions is expected to inhibit viral replication.

Once an appropriate target is selected, enzymatic RNA molecules capable of cleaving the target nucleotide sequence may be identified from a pool of enzymatic RNA molecules via the use of oligonucleotide probes. Alternatively, the recognition sequence of an enzymatic RNA molecule of the present invention may be mutated or modified so that it selectively targets the desired viral sequence. Methods of identifying suitable target sequences are available in the art; see, e.g., published PCT application nos. WO 93/23569, WO 91/04319, WO 91/04324, and WO 91/03162; and published European patent application no. EPO 585, 549, the disclosures of which are incorporated by reference herein.

Enzymatic RNA molecules of the present invention are preferably targeted to a highly-conserved region of a viral nucleic acid sequence so that all strains and types of such viruses may be treated with a single enzymatic RNA molecule or enzymatic RNA molecule species. Enzymatic RNA molecules of the present invention may be designed to target RNA or DNA sequences as appropriate; they may also be designed to target transcripts of viral nucleic acid sequences, whether those transcripts are comprised of RNA or DNA. Enzymatic RNA molecules according to the present invention may also be designed to target antisense nucleic acid sequences.

Enzymatic RNA molecules of the present invention may further be used to treat transformed eukaryotic cells—e.g., keratinocytes, hepatocytes or epithelial cells—in such a manner that they inhibit the expression of viral genes known or believed to cause cell immortalization or transformation. In another embodiment, enzymatic RNA molecules may be used to treat latent viral infections, by inhibiting gene expression required for the maintenance of the viral episomal genome.

If desired, a vector such as those described hereinbelow may be used in a therapeutic protocol via use of the methods and systems described in published international application no. WO 92/13070, the disclosures of which are incorporated by reference herein. Via one of the disclosed methods, expression of a therapeutic enzymatic RNA molecule of the present invention may be temporally regulated. Thus, a vector comprising sequences encoding therapeutic enzymatic RNA molecules of the present invention preferably includes a promoter which expresses enzymatic RNA molecules only in the presence of a nucleic acid molecule which is manifested when an "invading" organism or disease state is present. Such a "timed release" enzymatic RNA molecule then functions to impair or destroy the cell in which the unwanted organism or condition is found, to bring about reduced expression of a protein product related to the disease state, or to stimulate production of a "defensive" protein of the compromised cell.

Enzymatic RNA molecules of the present invention may also be used in vivo or in vitro to make defective viral particles which nonetheless retain their immunogenic properties. In this way, an organism's own immune system may be stimulated to combat infection by intact (i.e., non-defective) viral particles.

In a related aspect, vaccines or other preparations used for immunization may be formed from defective viruses (or portions thereof) created by a method of this invention. Methods for immunizing or vaccinating organisms using defective viral particles (e.g., with DNA or vectors encoding an enzymatic RNA molecule of this invention under the control of an appropriate promoter) are also contemplated herein.

Enzymatic RNA molecules of the present invention may also be conjugated or otherwise linked to viral particles or viruses, where the latter are used as vectors which may transport enzymatic RNA molecules to cells infected with another virus. Useful vectors of this type may be formed via standard technology; for example, adenovirus vectors and related methodologies may be effective in this regard.

Diagnostic uses of enzymatic RNA molecules of the present invention are also contemplated. For example, because of the relationship between enzymatic RNA molecule activity and target nucleic acid structure, mutations in any region of the target molecule may be detected, particularly where such mutations alter the base-pairing and three-dimensional structure of the target nucleotide sequence, whether RNA or DNA.

Further, by using multiple enzymatic RNA molecules as described in this invention, one may map nucleotide changes important to DNA or RNA structure and function in vitro, as well as in cells and tissues. Cleavage of target DNAs or RNAs with enzymatic RNA molecules of the present invention may be used to inhibit gene expression and to assist in defining the role of specified gene products in the progression of disease. In this application, other genetic targets may be identified as important mediators of the disease under investigation. Such experiments may lead to better treatment or modification of disease progression by providing the possibility of combinational therapies. Examples of the latter include application of multiple enzymatic RNA molecules targeted to different genes or nucleotide sequences; enzymatic RNA molecules coupled with known small molecule inhibitors; intermittent treatment with combinations of enzymatic RNA molecules and/or other chemical or biological molecules; and enzymatic RNA molecules administered in conjunction with therapeutic antisense sequences.

The present invention contemplates that enzymatic RNA molecules as described herein may be used as sequence-specific endoribonucleases. In various preferred embodiments, enzymatic RNA molecules cleave RNA substrates with high catalytic efficiency (e.g., $k_{cat}/K_m = 10^8 M^{-1} min^{-1}$).

It is also contemplated herein that the enzymatic RNA molecules of the present invention can act as sequence-specific endodeoxyribonucleases. In various preferred embodiments, enzymatic RNA molecules of the present invention cleave DNA with high catalytic efficiency. For example, in one embodiment, an enzymatic RNA molecule of the present invention has the following efficiency: $K_m = 1.9$ µM and $k_{cat} = 0.005$ min$^{-1}$ ($k_{cat}/K_m = 2700$ M$^{-1}$ min$^{-1}$). In another embodiment, an enzymatic RNA molecule has the following efficiency: $K_m = 2.0$ µM and $k_{cat} = 0.007$ min$^{-1}$ ($k_{cat}/K_m = 3600$ M$^{-1}$ min$^{-1}$). In various embodiments encompassed by the present invention, catalytic efficiencies are greatest under physiologic conditions—for example, when the temperature is about 37° C. and divalent cations are available at a concentration of about 10 mM (e.g., 10 mM MgCl$_2$). Thus, the catalytic efficiencies of the enzymatic RNA molecules of the present invention are preferably 10 or more times greater than that of the wild type, and the molecules also display improvement in both $K_m$ and $k_{cat}$.

In a related aspect, the enzymatic RNA molecules of this invention may be used to identify the nucleic acid sequence to which a proteinaceous or nonproteinaceous adjunct binds. The proteinaceous or nonproteinaceous adjunct contemplated may bind to specific nucleotide sequences. The term "adjunct" as used herein is meant to include proteinaceous or nonproteinaceous substances which are joined or added to the nucleic acid sequence but are not essentially a part of said sequence. The adjunct may be a protein, metal, inorganic molecule, lipid, or other substance.

For example, multiple enzymatic RNA molecules with known recognition sequences may be used to identify the nucleic acid sequence to which an adjunct is specifically bound. The identification of these nucleic acid sequences may be useful in identifying specific nucleic acid target sequences involved in gene expression.

In a related aspect, the enzymatic RNA molecules of this invention may be used to confirm the presence or absence of proteins or other adjuncts (proteinaceous or nonproteinaceous) which bind a nucleic acid substrate at a specific recognition site. For example, if a protein or other adjunct specifically binds to a known nucleic acid sequence, an enzymatic RNA molecule which is specific for the same nucleic acid sequences could be used to detect the presence or absence of such a protein or adjunct. The detection of such proteins or adjuncts may be useful for in vivo or in vitro diagnostic assays.

Enzymatic RNA molecules as described herein may also be used to regulate a variety of reaction systems, whether those reactions are occurring in vitro or in vivo. For example, it is contemplated that one may take advantage of the endonuclease activities of the molecules of the present invention by using them to regulate or terminate reactions in which transcription and/or translation are taking place. For example, enzymatic RNA molecules which recognize a specific nucleic acid residue sequence found in one or more of the PCR primers being used in a particular reaction may be added to such PCR reaction system to modulate or terminate processes dependent upon the primer targeted by the enzymatic RNA molecule. In this way, the entire PCR reaction would not be stopped; rather, only those products dependent upon the targeted primer(s) would be limited or eliminated.

Enzymatic RNA molecules of the present invention may also be used during the transcription of DNA sequences or oligomers to generate truncated transcripts in the same reaction vessel in which longer transcripts are generated. For example, if one wishes to generate a population of proteins with a membrane-spanning domain attached and a population of proteins with the membrane-spanning domain removed, the transcription/translation reactions may be allowed to run for a predetermined period of time until a predetermined amount of "intact" (i.e., non-truncated) product is generated. Subsequently, enzymatic RNA molecules of the present invention which have been engineered to cleave the transcripts at a site-specific location (i.e., a locus adjacent to the sequence for the membrane-spanning domain) may be added to the reaction mixture, which will result in the generation of truncated transcripts (and truncated protein products translated therefrom).

Alternatively, the enzymatic RNA molecules may be engineered to cleave the gene from which the messenger RNAs are being transcribed, which will produce a similar result with regard to the protein generated thereby. One of sufficient skill in the art will appreciate, based on the present disclosure, that enzymatic RNA molecules of the present invention may be adapted for a variety of uses; the uses disclosed herein should thus be understood to be exemplary and not limiting.

Use of enzymatic RNA molecules of the present invention in a coupled isothermal polynucleotide amplification and translation system could also modulate or "shut down" amplification processes at a predetermined time without simultaneously terminating the linked translation system. Similarly, the enzymatic RNA molecules of the present invention may be used to modulate or terminate therapeutic or diagnostic applications involving the use of "antisense" nucleotide sequences, e.g., by cleaving said antisense sequences.

Enzymatic RNA molecules of the present invention may also be used in oligonucleotide (e.g. DNA) footprinting or footprint analysis of protein-nucleotide binding. For example, enzymatic RNA molecules of the present invention may be prepared as disclosed herein, with a variety of different recognition sequences, and then admixed with a DNA sample to which a particular protein has bound. Labeled DNA fragments resulting from cleavage of the DNA sample by enzymatic RNA molecules of the present invention may then be analyzed according to standard protocols to enable one to identify specific protein binding sites on the DNA sample. Additionally, the same types of enzymatic RNA molecules of the present invention may be admixed with a sample of DNA to which the particular protein has not been added. Labeled DNA fragments resulting from cleavage of this second DNA sample may then be analyzed and the results compared with those generated when the protein-bound DNA sample was analyzed.

A variety of protocols are available for footprinting and similar analyses which are easily adapted for use with the enzymatic RNA molecules of the present invention, wherein the enzymatic RNA molecules disclosed herein are substituted in place of other nuclease enzymes. For example, see Ausubel, et al. (eds.), *Current Protocols in Molecular Biology*, John Wiley & Sons, Inc. (1994), for descriptions of a variety of protocols useful in conjunction with the enzymatic RNA molecules of the present invention.

It is anticipated that enzymatic RNA molecules of the present invention may also be engineered and used as highly-specific endonucleases, which makes them uniquely useful in vector construction, particularly when cleavage of single-stranded sequences is desired. For example, as disclosed above, an enzymatic RNA molecule of the present invention may be specifically targeted to a specific nucleotide sequence of from about 2 to 30 nucleotides in length; thus, such a molecule may be used in the design of vectors and cassettes for the delivery and expression of nucleotide sequences, i.e., by facilitating the insertion of predetermined nucleotide sequences into a compatible vector.

Other uses of the within-disclosed enzymatic RNA molecules will be apparent based on the present disclosure and are thus within the scope of the present invention.

G. Vectors

The present invention also features expression vectors including a nucleic acid segment encoding an enzymatic RNA molecule of the present invention situated within the vector, preferably in a manner which allows expression of that enzymatic RNA molecule within a target cell (e.g., a plant or animal cell).

Thus, in general, a vector according to the present invention includes a bacterial, viral or eukaryotic promoter within a plasmid, cosmid, phagemid, virus, viroid, or phage vector. Other suitable vectors include double-stranded DNA (dsDNA), partially double-stranded DNA, dsRNA, partially dsRNA, or single-stranded RNA (ssRNA) or DNA (ssDNA). It should also be appreciated that useful vectors according to the present invention need not be circular.

In one aspect of the present invention, a first enzymatic RNA molecule-encoding nucleotide sequence is transcriptionally linked to a promoter sequence. In another variation, one or more additional enzymatic RNA molecule-encoding nucleotide sequences are also included in the vector; said additional enzymatic RNA molecule-encoding sequences may be located on either side, or both sides, of a nucleotide sequence encoding the first enzymatic RNA molecule. Preferably, there are intervening nucleotides or nucleotide sequences between successive enzymatic RNA molecule-encoding sequences.

In another variation, nucleotide sequences flanking each of the additional enzymatic RNA molecule-encoding sequences are preferably provided, which sequences may be recognized by the first enzymatic RNA molecule. The intervening or flanking sequences preferably comprise at least 1 nucleotide; more preferably, intervening or flanking sequences are about 2–20 nucleotides in length, with sequences of about 5–10 nucleotides in length being particularly preferred.

The addition of polyadenine (poly(A)) tails may also be useful to protect the 3' end of an enzymatic RNA molecule according to the present invention. These may be provided by including a poly(A) signal site in the expression vector, which would signal a cell to add the poly(A) tail in vivo. Preferably, the signal is aligned in such a fashion that it prevents unwanted secondary structure formation with other parts of the enzymatic RNA molecule.

Alternatively, a poly(A) tail may be provided by introducing a poly(A) sequence directly into the expression vector. Since the poly(A) sequence may decrease in size over time when expressed in vivo, the vector may need to be monitored over time. Care must be taken, however, in the addition of a poly(A) tail which binds poly(A) binding proteins, which may prevent the enzymatic RNA molecule from acting upon its target nucleotide sequence. Other vectors and methods of generating same are described in the art; see, e.g., published international application no. WO 93/23569.

Thus, in one example, a vector may comprise a promoter operatively linked for expression to a nucleotide sequence encoding a first enzymatic RNA molecule followed, in a 3'→5' direction, by: (1) a "flanking" nucleotide sequence capable of being recognized and cleaved by said first enzymatic RNA molecule; (2) a nucleotide sequence encoding a second enzymatic RNA molecule; (3) another flanking nucleotide sequence capable of being recognized and cleaved by said first enzymatic RNA molecule; (4) a nucleotide sequence encoding a third enzymatic RNA molecule; (4) yet another flanking nucleotide sequence capable of being recognized and cleaved by said first enzymatic RNA molecule; and so forth.

Preferably, a vector according to the present invention includes a plurality of nucleic acid sequences encoding the second enzymatic RNA molecule, each flanked by nucleic acid sequences recognized by the first enzymatic RNA molecule. More preferably, such a plurality includes at least 5, preferably 7, more preferably 9 or more, nucleic acid sequences. In other embodiments, a vector as disclosed herein includes a promoter which regulates expression of the nucleic acid encoding the enzymatic RNA molecules from the vector.

The invention also contemplates that a promoter sequence is linked to a first or "releasing" enzymatic RNA molecule having an appropriate restriction endonuclease site. A single-stranded oligonucleotide is then provided which encodes the two flanking regions and a second (i.e., "therapeutic") enzymatic RNA molecule. The oligonucleotides are then allowed to form partial duplexes via hybridization at the flanking regions. The single-stranded sections are then filled in using a DNA polymerase and deoxyribonucleotide triphosphates (dNTPs) to form a dsDNA molecule, which may then be ligated to the restriction endonuclease site to form the desired vector. As noted above, the vector may be chosen from the group comprising plasmids, cosmids, phagemids, virus, viroids, or phage.

Preferably, the plurality of nucleic acid sequences are identical and are arranged in sequential fashion such that each has an identical end nearest to the promoter. If desired, a poly(A) sequence adjacent to the sequence encoding the first or second enzymatic RNA molecule may be provided to increase stability of the RNA produced by the vector and/or to enhance transport to appropriate cellular compartments. Further, a restriction endonuclease site adjacent to the nucleic acid encoding the first enzymatic RNA molecule may be provided to allow insertion of nucleic acid encoding the second enzymatic RNA molecule during construction of the vector.

If delivery of a vector construct to a eucaryotic cell is desired, cellular splicing mechanisms within the target cell(s) may be utilized or integrated to cleave out the therapeutic second enzymatic RNA molecule(s) by encoding recognition sequences for the second enzymatic RNA molecules within the flanking sequences of the expressed transcript. Multiple copies of the releasing first enzymatic RNA molecule may be provided to enhance release of the second (i.e. therapeutic) enzymatic RNA molecule if the turnover rate is slower than the degradation rate of the second enzymatic RNA molecule. If the target cell is a bacterial cell, in vitro modifications and certain cell modifications may be enhanced by providing appropriate nucleotide sequences within the vector and are useful in the enhancement of the turnover rate, enzymatic stability, and cleavage activity of the within-disclosed enzymatic RNA molecules.

A method of forming an enzymatic RNA molecule expression vector includes providing a vector comprising nucleic acid encoding a first enzymatic RNA molecule, as discussed above, and providing a single-stranded DNA molecule encoding a second enzymatic RNA molecule, also as discussed above. The single-stranded DNA is then allowed to anneal to form a partial duplex DNA which can be filled in by treatment with an appropriate enzyme, such as a DNA polymerase in the presence of dNTPs, to form a duplex DNA which can then be ligated to the vector. Large vectors resulting from use of this method can then be selected to insure that a high copy number of the single-stranded DNA encoding the second enzymatic RNA molecule is incorporated into the vector.

A method for producing enzymatic RNA molecules thus involves providing a vector as described above, expressing RNA from that vector, and allowing cleavage by the first enzymatic RNA molecule to release the second (and any subsequent) enzymatic RNA molecule.

Suitable restriction endonuclease sites may also be provided to ease the construction of such a vector in DNA vectors or in requisite DNA vectors of an RNA expression system.

The second (and any additional) enzymatic RNA molecule may be any desired type of enzymatic RNA molecule, such as a ribozyme, including group I and group II introns, hammerhead, hairpin, and other types of ribozymes or enzymatically active portions thereof.

The first enzymatic RNA molecule is selected to cleave the encoded cleavage (e.g., "flanking") sequence, and may also be any desired ribozyme—e.g., a ribozyme derived from Tetrahymena—which may, for example, include an embedded restriction endonuclease site in the center of a self-recognition sequence to aid in vector construction. This endonuclease site is useful for construction of, and subsequent analysis of, a vector as described herein.

A vector according to the present invention is preferably operably linked for expression to an appropriate promoter. For example, a vector according to the present invention may comprise an enzymatic RNA molecule under the control of a viral promoter, such as an Epstein-Barr Virus (EBV) promoter. A variety of viral promoters useful for this purpose are known in the art; see, e.g., those described in published PCT application no. WO 93/23569.

In another variation, a vector according to the present invention includes two or more enzymatic RNA molecules. In one embodiment, a first enzymatic RNA molecule has intramolecular cleaving activity and is able to recognize and cleave nucleotide sequences to release other enzymatic RNA sequences; i.e., it is able to function to "release" other enzymatic RNA molecules from the vector. For example, a vector is preferably constructed so that when the first enzymatic RNA molecule is expressed, that first molecule is able to cleave nucleotide sequences flanking additional nucleotide sequences encoding a second enzymatic RNA molecule, a third enzymatic RNA molecule, and so forth. Presuming said first enzymatic RNA molecule (i.e., the "releasing" molecule) is able to cleave oligonucleotide sequences intramolecularly, the additional (e.g. second, third, and so on) enzymatic RNA molecules (i.e., the "released" molecules) need not possess characteristics identical to the "releasing" molecule.

Alternatively, the first enzymatic RNA molecule may be encoded on a separate vector from the second enzymatic RNA molecule(s) and may have intermolecular cleaving activity. As noted herein, the first enzymatic RNA molecule can be a self-cleaving enzymatic RNA molecule (e.g., a ribozyme), and the second enzymatic RNA molecule may be any desired type of enzymatic RNA molecule (e.g., a ribozyme). When a vector is caused to express RNA from these nucleic acid sequences, that RNA has the ability under appropriate conditions to cleave each of the flanking regions, thereby releasing one or more copies of the second enzymatic RNA molecule. If desired, several different second enzymatic RNA molecules can be placed in the same cell or carrier to produce different ribozymes.

Methods of isolating and purifying enzymatic RNA molecules of the present invention are also contemplated. In addition to the methods described herein, various purification methods (e.g. those using HPLC) and chromatographic isolation techniques are available in the art. See, e.g., the methods described in published international application no. WO 93/23569, the disclosures of which are incorporated herein by reference.

It should also be understood that various combinations of the embodiments described herein are included within the scope of the present invention. Other features and advantages of the present invention will be apparent from the descriptions hereinabove, from the Examples to follow, and from the claims.

EXAMPLES

The following examples illustrate, but do not limit, the present invention.

Example 1

In Vitro Evolution of Enzymatic RNA Molecules

The Tetrahymena ribozyme is a self-splicing group I intron derived from the large ribosomal RNA (rRNA) precursor of *Tetrahymena thermophila*. Its biological function is to catalyze its own excision from precursor rRNA to produce mature rRNA. This function has been expressed in vitro (Kruger, et al., *Cell* 31: 147 (1982)) and has been generalized to include various phosphoester transfer reactions involving RNA substrates (Zaug, et al., *Science* 231: 470 (1986); Kay, et al., *Nature* 327: 343 (1987); Been, et al., *Science* 239: 1412 (1988); Woodson, et al., *Cell* 57: 335 (1989); Doudna, et al., *Nature* 339: 519 (1989)). For example, the ribozyme has been used as a sequence-specific endoribonuclease (Zaug, et al., *Id.* (1986); Murphy, et al., *PNAS USA* 86: 9218 (1989)), a reaction that proceeds with high catalytic efficiency ($k_{cat}/K_m = 10^8 M^{-1}$ $min^{-1}$) (Herschlag, et al., *Biochemistry* 29: 10159 (1990)).

The Tetrahymena ribozyme consists of 413 nucleotides and assumes a well-defined secondary and tertiary structure that is responsible for its catalytic activity (Burke, et al., *Nucleic Acids Res.* 15: 7217 (1987); Kim, et al., *PNAS USA* 84: 8788 (1987); Celander, et al., *Science* 251: 401 (1991); Michel, et al., *J. Mol. Biol.* 216: 585 (1990). Phylogenetic analysis, supported by site-directed mutagenesis and deletion studies, points out a distinction between a conserved catalytic core (comprising about one-third of the molecule) and surrounding stem-loop elements that offer structural support but are not essential for catalytic activity. (See Davies, et al., *Nature* 300: 719 (1982); Michel, et al., *Biochimie* 64: 867 (1982); Michel, et al., *EMBO J.* 2: 33 (1983); Cech, et al., *Gene* 73: 259 (1988); Price, et al., *Nucl. Acids Res.* 13: 1871 (1985); Szostak, et al., *Nature* 322: 83 (1986); Joyce, et al., *Nucl. Acids Res.* 15: 9825 (1987); Barfod, et al., *Genes Dev.* 2: 652 (1988); Joyce, et al., *Nucleic Acids Res.* 17: 7879 (1989); Couture, et al., *J. Mol. Biol.* 215: 345 (1990); Beaudry and Joyce, *Biochemistry* 29: 6534 (1990).)

The ribozyme can also act as a sequence-specific endodeoxyribonuclease (Robertson and Joyce, *Id.* (1990)), although the efficiency of DNA cleavage is low ($k_{cat}/K_m = 200 M^{-1}$ $min^{-1}$, determined at 50° C., 10 mM MgCl$_2$) (Herschlag, et al., *Nature* 344: 405 (1990)). The efficiency of RNA-catalyzed DNA cleavage under physiologic conditions is even lower ($k_{cat}/K_m = 36 M^{-1}$ $min^{-1}$, determined at 37° C., 10 mM MgCl$_2$; see below).

One goal achieved herein was the improvement of the catalytic efficiency of RNA-catalyzed DNA cleavage under physiologic conditions, thereby obtaining ribozymes that could cleave DNA in vivo. It is not obvious how one should change the Tetrahymena ribozyme to convert it from an RNA-cleaving to a DNA-cleaving enzyme. Thus, directed evolution was selected as a means to acquire the desired phenotype.

A method of in vitro evolution has now been developed for enzyme engineering. For example, the Tetrahymena ribozyme, an RNA enzyme that typically catalyzes sequence-specific phosphoester transfer reactions that result in cleavage or ligation of RNA substrates, is useful in the within-described in vitro evolutionary process. The wild-type enzyme can be used to cleave a single-stranded DNA substrate, albeit only under conditions of high temperature (50° C.) or high MgCl$_2$ concentration (50 mM), or both. (See Robertson and Joyce, *Id.* (1990).) A kinetic study showed that, even at 50° C., this reaction is inefficient compared to the "native" reaction with an RNA substrate. As noted above, under physiologic conditions (e.g., 37° C., 10 mM MgCl$_2$), the DNA cleavage reaction using wild-type ribozyme is almost undetectable.

To obtain ribozymes that cleave DNA with improved efficiency under physiologic conditions, directed evolution was used to generate and maintain a population of $10^{13}$ ribozymes over ten successive generations. Complete access to genotypic and phenotypic parameters for the entire population over the course of its evolutionary history was also maintained.

Darwinian evolution requires the repeated operation of three processes: (a) introduction of genetic variation; (b) selection of individuals on the basis of some fitness criterion; and (c) amplification of the selected individuals. Each of these processes can be realized in vitro (Joyce, *Id.* (1989)). A gene can be mutagenized by chemical modification, incorporation of randomized mutagenic oligodeoxynucleotides, or inaccurate copying by a polymerase. (See, e.g., Chu, et al., *Virology* 98: 168 (1979); Shortle, et al., *Meth. Enzymol.* 100: 457 (1983); Myers, et al., *Science* 229: 242 (1985); Matteucci, et al., *Nucleic Acids Res.* 11: 3113 (1983); Wells, et al., *Gene* 34: 315 (1985); McNeil, et al., *Mol. Cell. Biol.* 5: 3545 (1985); Hutchison, et al., *PNAS USA* 83: 710 (1986); Derbyshire, et al., *Gene* 46: 145 (1986); Zakour, et al., *Nature* 295: 708 (1982); Lehtovaara, et al., *Protein Eng.* 2: 63 (1988); Leung, et al., *Technique* 1: 11 (1989); Zhou, et al., *Nucl. Acids Res.* 19: 6052 (1991).)

The gene product can be selected, for example, by its ability to bind a ligand or to carry out a chemical reaction. (See, e.g., Joyce, *Id.* (1989); Robertson and Joyce, *Id.* (1990); Tuerk, et al., *Id.* (1990).) The gene that corresponds to the selected gene product can be amplified by a reciprocal primer method, such as the polymerase chain reaction (PCR). (See, e.g., Saiki, et al., *Science* 230: 1350–54 (1985); Saiki, et al., *Science* 239: 487–491 (1988).)

Alternatively, nucleic acid amplification may be carried out using self-sustained sequence replication (3SR). (See, e.g., Guatelli, et al., *PNAS USA* 87: 1874 (1990), the disclosures of which are incorporated by reference herein.) According to the 3SR method, target nucleic acid sequences may be amplified (replicated) exponentially in vitro under isothermal conditions by using three enzymatic activities essential to retroviral replication: (1) reverse transcriptase, (2) RNase H, and (3) a DNA-dependent RNA polymerase. By mimicking the retroviral strategy of RNA replication by means of cDNA intermediates, this reaction accumulates cDNA and RNA copies of the original target.

In summary, a continuous series of reverse transcription and transcription reactions replicates an RNA target sequence by means of cDNA intermediates. The crucial elements of this design are (a) the oligonucleotide primers both specify the target and contain 5' extensions encoding the T7 RNA polymerase binding site, so that the resultant cDNAs are competent transcription templates; (b) cDNA synthesis can proceed to completion of both strands due to the degradation of RNA in the intermediate RNA-DNA hybrid by RNase H; and (c) the reaction products (cDNA and RNA) can function as templates for subsequent steps, enabling exponential replication.

A major obstacle to realizing Darwinian evolution in vitro is the need to integrate mutation and amplification, both of which are genotype-related, with selection, which is phenotype-related. In the case of RNA enzymes, for which genotype and phenotype are embodied in the same molecule, the task is simplified.

A. Amplification

Using a combination of two polymerase enzymes, it is possible to amplify virtually any RNA. (See Kwoh, et al., *PNAS USA* 86: 1173 (1989); Joyce, in *Molecular Biology of RNA: UCLA Symposia on Molecular and Cellular Biology*, T. R. Cech (ed.), Liss, NY, 1989, pp. 361–371.) RNA is copied to a complementary DNA (cDNA) with reverse transcriptase (RT), and the resulting cDNA is transcribed to RNA with T7 RNA polymerase (T7 Pol) (FIGS. 2A and 2B).

Figure 2A:
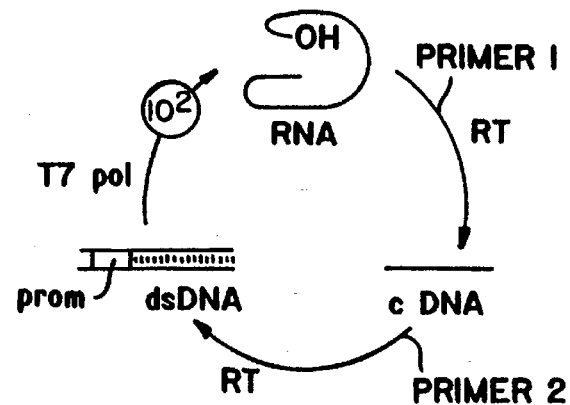
In FIG. 2A, the overall procedure for RNA amplification is shown. "RT"= reverse transcriptase; "T7 pol"=T7 polymerase; "prom"= promoter, and "RNA" represents the enzymatic RNA molecule.
Figure 2B:
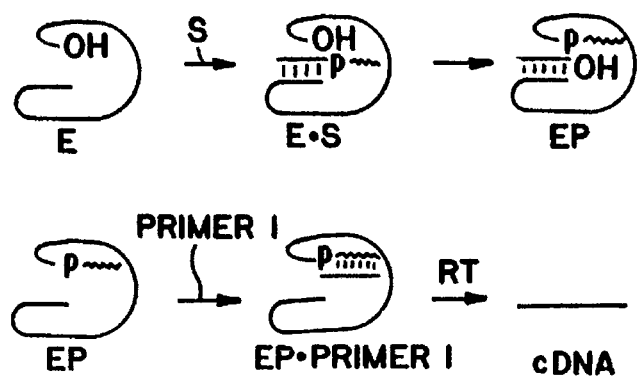
In FIG. 2B, the procedure for selective amplification based on phosphoester transfer activity of a group I ribozyme is shown. "E" represents the enzymatic RNA molecule; "S" represents substrate; "E·S" represents enzyme/substrate complex; and "EP" represents enzyme/product complex.

FIGS. 2A and 2B illustrate the procedure for amplification of catalytic RNA. Amplification occurs during transcription as a consequence of the ability of T7 RNA polymerase to generate 200 to 1200 copies of RNA transcript per copy of cDNA template (Chamberlin, et al., in *The Enzymes, Vol.* 15, P. D. Boyer (ed.), Academic Press, NY, 1982, pp. 87–108).

The amplification reaction is done in a single test tube at a constant temperature of 37° C., resulting in an increase of $10^3$ to $10^6$ times the original input of RNA after one hour (Guatelli, et al., *PNAS USA* 87: 1874 (1990); Joyce, in *Antisense RNA and DNA*, J. A. H. Murray (ed.), Wiley-Liss, NY, 1992, pp. 353–372). The procedure for RNA amplification, which is illustrated in FIG. 2A, is essentially as follows. Reaction conditions: $10^{-5}$ to $10^1$ nM RNA, 1 µM primers, 2 mM each nucleoside triphosphate (NTP), 0.2 mM each deoxynucleoside triphosphate (dNTP), 10 mM $MgCl_2$, 50 mM tris-HCl (pH 7.5), 5 mM dithiothreitol (DTT), AMV reverse transcriptase at 0.5 U/µl, T7 RNA polymerase at 5 U/µl; 37° C., 1 hour.

B. Selection

The amplification was performed selectively in that individual RNAs in the population were required to catalyze a particular chemical reaction in order to become eligible for amplification (Joyce, *Id.* (1989); Robertson and Joyce, *Id.* (1990)). The selection was based on the ability of group I ribozymes to catalyze a sequence-specific phosphoester transfer reaction involving an oligonucleotide (or oligodeoxynucleotide) substrate (see FIG. 2B).

FIG. 2B illustrates the procedure for selective amplification based on phosphoester transfer activity of a group I ribozyme. The procedure for selective amplification based on phosphoester transfer activity of a group I ribozyme is essentially as follows.

The 3' portion of the substrate, $d(A_3(TA_3)_3)$ (SEQ ID NO 5), was transferred to the 3'-terminal guanosine of the ribozyme. Reaction conditions for RNA-catalyzed DNA cleavage were as follows: 1 µM Tetrahymena ribozyme (L-21 form), 10 µM $d(GGCCCTCTA_3(TA_3)_3$ (SEQ ID NO 6), 10 mM $MgCl_2$, 30 mM N-[2-hydroxymethyl]-piperazine-N-[3-propanesulfonic acid] (EPPS) (pH 7.5); 37° C., 1 hour. Selective amplification occurred as described in subsection 1 above with respect to selective amplification of catalytic RNA, with $d((T_3A)_3T_3C)$ (SEQ ID NO 7) as primer 1 and d(ATCGATAATACGACTCACTATAGGAGG-GAAAAGTTATCAGGC) (SEQ ID NO 8) as primer 2. Subsequent selective cDNA synthesis with 0.2 pmol of the selective amplification product under conditions as described in subsection 1 above, but omitting primer 2 and T7 polymerase. Subsequent PCR amplification with 0.01 pmol of the selective cDNA synthesis product in a reaction mixture (100 µl volume) containing 0.2 µM d(CGAG-TACTCCAAAACTAATC) (SEQ ID NO 9), 0.2 µM primer 2 (as above), 0.2 mM dNTPs, 50 mM KCl, 1.5 mM $MgCl_2$, 10 mM tris-HCl (pH 8.3), 0.01% gelatin, and 2.5 U of Taq DNA polymerase (Perkin-Elmer, Norwalk, Conn.), 30 cycles of 92° C. for 1 minute, 45° C. for 1 minute, and 72° C. for 1 minute. PCR products were purified by extraction with chloroform and isoamyl alcohol and by precipitation with ethanol, and used to transcribe RNA as described in subsection 3 below.

The product of the reaction was a molecule that contained the 3' portion of the substrate attached to the 3' end of the ribozyme (EP; see FIGS. 2A and 2B). Selection occurred when an oligodeoxynucleotide primer was hybridized across the ligation junction and used to initiate cDNA synthesis. The primer did not bind to unreacted starting materials ($<10^{-8}$ compared to reaction products) and thus led to selective amplification of the catalytically active RNAs.

C. Introduction of Variation

Mutations were introduced in two ways. First, at the outset, a set of mutagenic oligodeoxynucleotides that contained random substitutions at a fixed frequency of occurrence was used. These partially randomized oligodeoxynucleotides were produced on an automated DNA synthesizer with nucleoside 3'-phosphoramidite solutions that had been doped with a small percentage of each of the three incorrect monomers (McNeil, et al., *Id.* (1985); Hutchison, et al., *Id.* (1986)). Second, after each round of selective amplification, random mutations were introduced by performing the PCR under mutagenic conditions (Leung, et al., *Id.* (1989); Zhou, et al., *Id.* (1991)).

In general, when using PCR procedures, each primer works in combination with a second primer to amplify a target nucleic acid sequence. The choice of PCR primer pairs for use in PCR is governed by various considerations, as discussed herein. That is, the primers have a nucleotide sequence that is complementary to a sequence conserved in the gene of choice. Useful priming sequences have been disclosed herein. The strategy used for cloning the selected genes will depend, as is well known in the art, on the type, complexity, and purity of the nucleic acids making up the various genes. Other factors include whether or not the genes are to be amplified and/or mutagenized.

In general, the exemplary genes are comprised of polynucleotide coding strands, such as mRNA and/or the sense strand of genomic DNA. If the polynucleotide sequence is in the form of double stranded genomic DNA, it is usually first denatured, typically by melting, into single strands. A gene sequence is subjected to a PCR reaction by treating (contacting) the sequence with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length, conserved within the gene sequence.

The PCR reaction is performed by mixing the PCR primer pair, preferably a predetermined amount thereof, with the nucleic acids of the selected gene or DNA nucleotide sequence, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different polypeptide-encoding DNA homologs.

The PCR reaction is performed using any suitable method. PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). *Thermus aquaticus* DNA polymerase I, which is useful in PCR, is described in U.S. Pat. No. 4,889,818.

Restriction sites may also be incorporated into the 5' and 3' primers to enable the amplification products to be subcloned into sequencing or expression vectors. It may also be helpful to place a 4-base spacer sequence proximal to the restriction site to improve the efficiency of cutting amplification products with enzymes.

In the presently-described study, the PCR was performed under standard reaction conditions (see FIGS. 2A and 2B, and subsections 1 and 2 above), resulting in an error rate of approximately 0.1% per position per generation. A mutagenic, modified PCR procedure that provides an error rate of 0.66±0.13% per position (95% confidence level) has also been developed. (See Cadwell and Joyce, *PCR Methods Appl.* 2: 28 (1992), which is incorporated herein by reference.) The RNAs obtained by selective amplification were subjected to reverse transcription, the resulting cDNAs were PCR amplified, and the PCR products were transcribed to produce a progeny distribution of mutant RNAs.

Integration of the PCR with the selective RNA amplification procedure was useful in three other ways. First, it increases the overall amplification by about $10^3$ times. Second, it simplifies the process of subcloning individuals from the evolving population. Normally, only a small portion of the DNA in the RNA amplification mixture is fully double-stranded, but with the PCR, the amount of double-stranded DNA (dsDNA) is greatly increased. Third, it returns the RNA to a form that can participate in the RNA-catalyzed phosphoester transfer reaction. After phosphoester transfer, the ribozyme has the 3' portion of the substrate attached to its 3' end, and after selective RNA amplification, the substrate sequence remains attached (see FIGS. 2A and 2B). However, by subsequent use of PCR, followed by in vitro transcription, the original 3' end of the ribozymes is restored.

D. Ribozymes: Generations

The entire series of events, beginning with a heterogeneous population of RNAs, proceeding with RNA catalysis in the target reaction, selective amplification of catalytically active RNAs, reverse transcription of the selective amplification products, mutagenic PCR, and in vitro transcription to produce a progeny distribution of RNAs, is referred to as one "generation". Typically, a generation is completed in one to two working days, excluding time for analytic work. The initial population of mutant RNAs is referred to as "generation 0", while subsequent populations are referred to as "generation 1", "generation 2", and so forth. In principle, there is no limit to the number of successive generations that can be obtained.

In practice, there is always the danger of developing a "parasite" that circumvents the selection criterion and is amplified more efficiently than the most reactive species. In one of the within-disclosed experiments, for example, a sequence arose that allowed false hybridization of one of the amplification primers at an internal site, generating a species with a 53-nucleotide deletion that was amplified more efficiently than the full-length ribozyme. Thus, it is important to monitor the populations generated and remove such "parasites", if and when they appear.

To generate the initial population of ribozyme variants, random mutations were introduced throughout the catalytic core of the molecule. Four synthetic oligodeoxynucleotides were prepared, each of which randomly mutagenizes 35 nucleotide positions at an error rate of 5% per position (FIG. 3).

Figure 3:
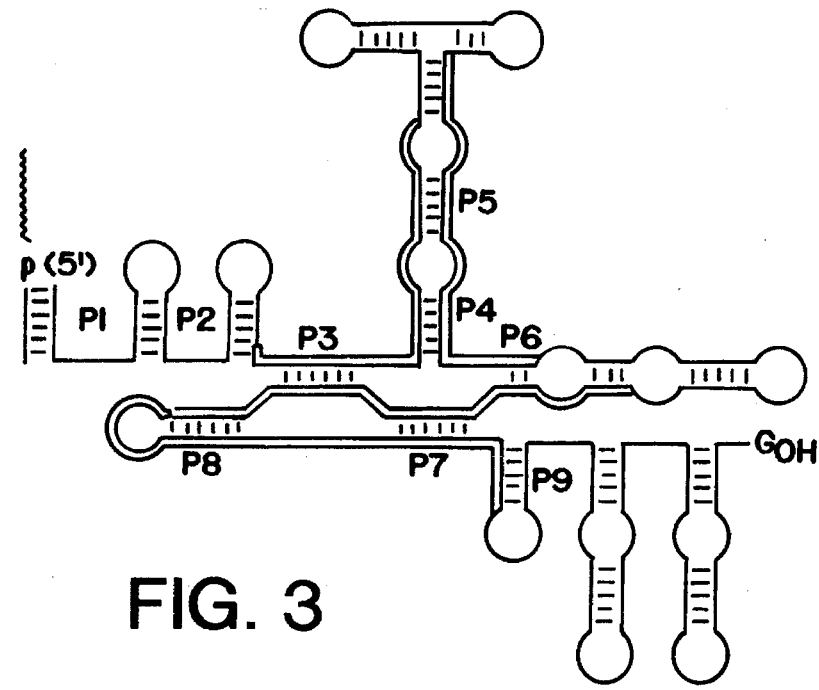
FIG. 3 illustrates the secondary structure of the Tetrahymena ribozyme (L-21 form) showing those regions that were randomly mutagenized (boxed segments).

FIG. 3 illustrates the secondary structure of the Tetrahymena ribozyme (L-21 form) showing those regions that were randomly mutagenized (boxed segments). The transcription conditions were essentially as follows: 2 pmol of DNA template (containing mutagenic oligodeoxynucleotides), 2 mM NTP's, 15 mM $MgCl_2$, 2 mM spermidine, 5 mM DTT, 50 mM tris-HCl (pH 7.5), 1500 U of T7 RNA polymerase were admixed to a volume of 60 µl and held at 37° C. for 2 hours. RNA was purified by electrophoresis in a 5% polyacrylamide-8M urea gel and subsequent column chromatography on Sephadex G-50.

The degenerate oligodeoxynucleotides were incorporated into a DNA template that encodes the ribozyme, and the template was transcribed directly to produce the mutant RNAs (Joyce and Inouye, *Nucl. Acids Res.* 17: 711 (1989)). Twenty pmol ($10^{13}$ molecules) of material was used at the beginning. Thus, the generation 0 population was expected to contain the wild-type ribozyme, all possible 1-, 2-, 3-, and 4-error mutants, and a sampling of the higher-error mutants (see Table 1).

Table 1 illustrates the composition of the initial population (generation 0). The probability P of having K errors in a doped oligonucleotide of length v and degeneracy d is given by: $P(k,v,d)=[v!/(v-k)!k!]d^k(1-d)^{v-k}$. A total of 140 positions were randomly mutagenized (v=140) at a degeneracy of 5% per position (d=0.05). The number of distinct k-error sequences of length v is given by: $N_k=[v!/(v-k)!k!]3^k$. The expected number of copies per sequence is based on a population size of 20 pmol ($1.2 \times 10^{13}$ molecules).

TABLE 1

| Errors | Probability (%) | Sequences | Copies/Sequence |
|---|---|---|---|
| 0 (wt) | 0.1 | 1 | $9 \times 10^9$ |
| 1 | 0.6 | 420 | $2 \times 10^8$ |
| 2 | 2.1 | $9 \times 10^4$ | $3 \times 10^6$ |
| 3 | 5.0 | $1 \times 10^7$ | $5 \times 10^4$ |
| 4 | 9.0 | $1 \times 10^9$ | $9 \times 10^2$ |
| 5 | 12.8 | $1 \times 10^{11}$ | 15 |
| 6 | 15.2 | $7 \times 10^{12}$ | 0.3 |
| 7+ | 55.4 | | |

The evolution experiment spanned ten successive generations; each generation began with 20 pmol of RNA. The amount of RNA was quantified after selective amplification and after transcription (see FIG. 4).

Figure 4:
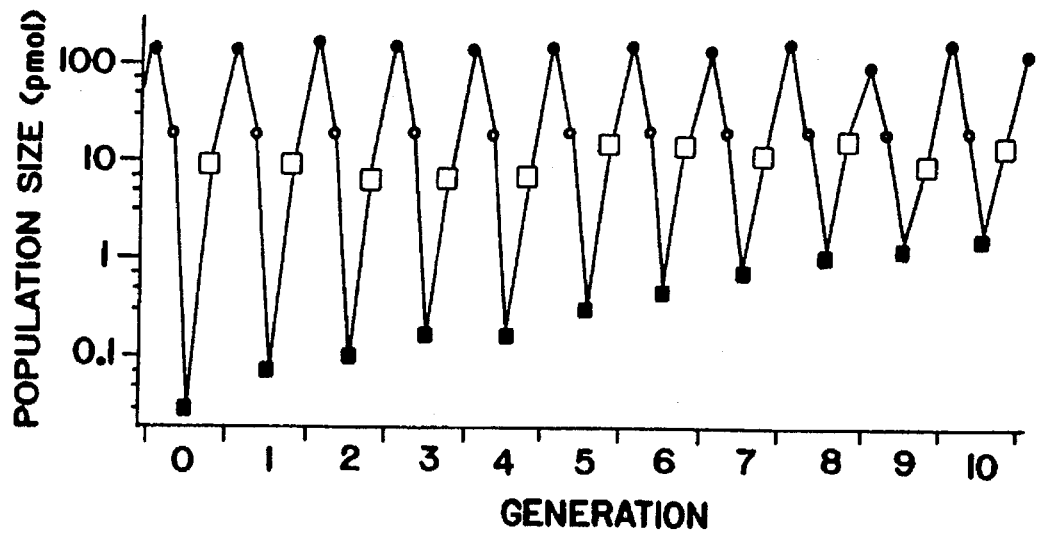
FIG. 4 illustrates the course of evolution over 10 successive generation, highlighting changes in RNA population size over time. Closed circles represent RNA population size after transcription, quantitated by [$^3$H]uracil content; open circles represent RNA population size at the start of each generation, based on 20-pmol portions; closed squares represent RNA population size after reaction with substrate, estimated by the assay described in subsection 4 herein; and open squares represent RNA population size after selective amplification, quantitated by acid precipitation at 4° C. of [$\alpha$-$^{32}$P]GTP-labeled progeny RNA.

FIG. 4 illustrates the course of evolution over 10 successive generation, highlighting changes in RNA population size over time. Closed circles represent RNA population size after transcription, quantitated by [$^3$H]uracil content; open circles represent RNA population size at the start of each generation, based on 20-pmol portions; closed squares represent RNA population size after reaction with substrate, estimated by the assay described in subsection 4 herein; and open squares represent RNA population size after selective amplification, quantitated by acid precipitation at 4° C. of [α-$^{32}$P]GTP-labeled progeny RNA.

DNA cleavage activity for the population as a whole was monitored by a gel electrophoresis assay involving cleavage of [5'-$^{32}$P]-labeled d(GGCCCTCT-A$_3$(TA$_3$)$_3$) (SEQ ID NO 6) to yield d(GGCCCTCT) (SEQ ID NO 10) (data not shown). Cleavage of the substrate ("S") d(GGCCCTCT-A$_3$(TA$_3$)$_3$) (SEQ ID NO 6) in the absence of enzyme, in the presence of the wild-type Tetrahymena ribozyme (L-21 form), and in the presence of the population of RNAs obtained at each generation (G$_n$; n=0–10) was measured (data not shown).

Reaction conditions were as follows: 0.5 μM ribozyme, 0.1 μM substrate (2.6 μCi/pmol), 30 mM EPPS (pH 7.5); either 10 mM MgCl$_2$, 37° C., 1 hour (low) or 50 mM MgCl$_2$, 2 mM spermidine, 50° C., 1 hour (high). Reaction products were separated by electrophoresis in a 20% polyacrylamide-8M urea gel, of which autoradiograms were made; P represented [5'-$^{32}$P]d(GGCCCTCT) (SEQ ID NO 10), and P$_{+1}$ represented [5'-$^{32}$P]d(GGCCCTCTA) (SEQ ID NO 11) (not shown).

It is expected that any given mutation would more likely be detrimental than beneficial, although there may be a substantial number of neutral mutations. Indeed, DNA cleavage activity for the generation 0 population is less efficient than for the wild type. The generation 1 population, having been selected for DNA cleavage activity under physiologic conditions, showed improved catalytic activity compared to generation 0 and is slightly improved over the wild type. Through successive generations, there is continued improvement of phenotype. By generation 7, the population as a whole cleaves DNA more efficiently at 37° C. and 10 mM MgCl$_2$ than does the wild type at the high-temperature, high-MgCl$_2$ condition. Through generation 10, the rate of improvement has yet to level off.

RNAs from each generation were purified by polyacrylamide gel electrophoresis and Sephadex chromatography. To provide a more formal assay of DNA cleavage activity, d(GGCCCTCTA$_3$(TA$_3$)$_3$[5'-$^{32}$P]A) (SEQ ID NO 13) substrate was prepared as follows, and formation of both the ribozyme-d(A$_3$(TA$_3$)$_3$A) (SEQ ID NO 12) covalent intermediate and the RNA-catalyzed site-specific hydrolysis product d (A$_3$(TA$_3$)$_3$A) (SEQ ID NO 12) was measured (see FIG. 5). (See also Inoue, et al., *J. Mol. Biol.* 189: 143 (1986).)

Figure 5:
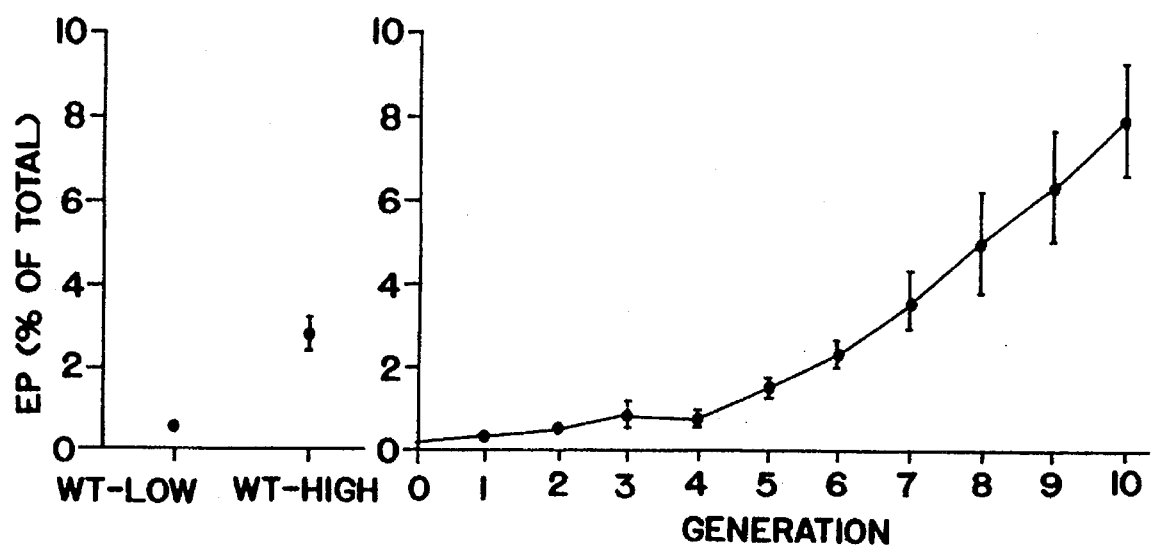
FIG. 5 illustrates the cleavage of [3'-$^{32}$P]dA-labeled d(GGCCCTCT-A$_3$ (TA$_3$)$_3$[5'-$^{32}$P]A) (SEQ ID NO 13). Cleavage of [3'-$^{32}$P]dA-labeled d(GGCCCTCT-A$^3$(TA$_3$)$_3$ [5'- $^{32}$P]A) (SEQ ID NO 13) was conducted under reaction conditions as described hereinabove prior to autoradiogram. Substrate (S), enzyme/product (EP), and product (P) were separated by electrophoresis in a 20% polyacrylamide-8M urea gel. Individual bands were cut from the gel and quantitated by Cerenkov counting. Data points are the average of five replicate experiments performed on three different days with two different preparations of substrate. Error bars correspond to ±1 SD.

FIG. 5 illustrates the cleavage of [3'-$^{32}$P]dA-labeled d(GGCCCTCT-A$_3$(TA$_3$)$_3$[5'-$^{32}$P]A) (SEQ ID NO 13). Cleavage of [3'-$^{32}$P]dA-labeled d (GGCCCTCT-A$_3$ (TA$_3$)$_3$ [5'-$^{32}$P]A) (SEQ ID NO 13) was conducted under reaction conditions as described hereinabove prior to autoradiogram. Substrate (S), enzyme/product (EP), and product (P) (see FIG. 2) were separated by electrophoresis in a 20% polyacrylamide-8M urea gel. Individual bands were cut from the gel and quantitated by Cerenkov counting. Data points are the average of five replicate experiments performed on three different days with two different preparations of substrate. Error bars correspond to ±1 SD.

Substrate was prepared via the following procedure. The [3'-$^{32}$P]-labeled DNA substrate was prepared with terminal deoxynucleotide transferase. Reaction conditions were as follows: 4 μM d(GGCCCTCT-A$_3$(TA$_3$)$_3$) (SEQ ID NO 6), 1 μM [α-$^{32}$P]dATP (3 μCi/pmol), 1 mM CoCl$_2$, 1 mM DTT, 50 mM potassium cacodylate (pH 7.2) and terminal transferase (BRL) at 2.7 U/μl, incubated at 37° C. for 30 minutes. The product corresponding to addition of a single dA residue was purified by electrophoresis in a 20% polyacrylamide-8M urea gel and subsequent affinity chromatography on Nensorb (duPont, Wilmington, Del.).

The hydrolysis product forms either by direct cleavage of the DNA substrate or by cleavage of the ribozyme-d(A$_3$(TA$_3$)$_3$A) (SEQ ID NO 12) covalent intermediate. Together, these reactions account for less than 5% of the cleaved substrate.

After ten generations, DNA cleavage activity for the population as a whole is 30 times higher than that of the wild type. Because selection is based on primer hybridization to the EP covalent intermediate (see FIG. 2B), there is selection pressure against the subsequent site-specific hydrolysis reaction. As a consequence, the efficiency of the hydrolysis reaction relative to the initial phosphoester transfer event drops from 4.9% for the wild type to 1.5% for the generation 10 population. There is selection pressure favoring accurate cleavage of the DNA at the target phosphodiester; inaccurate cleavage would result in partial mismatch of the primer used to initiate selective amplification. The accuracy of cleavage at first declines from 90% for the wild type to 45% for the generation 8 population, and then rises to 60% for the generation 10 population. There are some individuals in the population that sacrifice accuracy for improved cleavage activity in order to enjoy an overall selective advantage (see below). Of course, a preferred result is an individual having both high accuracy and high cleavage activity.

E. Evolutionary History

Although evolution in natural populations is an accomplished fact, evolution in vitro is a work in progress that allows the experimenter to access any time period in evolutionary history. Subclones were obtained from the evolving population at every generation, essentially as follows. DNAs used to transcribe the population of RNAs at each generation (see subsections 1–3 above) were amplified in a second PCR reaction with primers 5'-CCAAGCT-TGATCTCGAGTACTCCAAAACTAATC-3' (SEQ ID NO 14) and 5'-CTGCAGAATTCTAATACGACTCACTAT-AGGAGGGAAAAGTTATCAGGC-3' (SEQ ID NO 15), producing a 435-bp (base pair) fragment with unique restriction sites at its ends. The fragment was digested with Eco RI and Hind III and ligated into a pUC18 vector that had been linearized with Eco RI and Hind III and purified in a 1.5% agarose gel. The resulting plasmid DNAs were used to transform competent DH5α-F' cells (see Hanahan, in *DNA Cloning: A Practical Approach*, D. M. Glover, ed., IRL Press, Oxford, 1985, pp. 109–135), which were then grown on ampicillin-containing plates. Individual colonies were chosen at random and grown overnight in liquid media. DNA was prepared by the boiling lysis method (Holmes, et al., *Anal. Biochem.* 114: 193 (1981)) and screened for the insert by restriction digestion.

As noted, subclones were obtained from the evolving population at every generation. Generations 3, 6, and 9 were chosen for detailed analysis. DNA was prepared from 25 subclones at generations 3 and 6 and from 50 subclones at generation 9. The nucleotide sequence of the entire ribozyme gene was determined for each of these subclones essentially as follows.

Cloned individuals were sequenced by the dideoxy chain-termination method (Sanger, et al., *PNAS USA* 74: 5463 (1977); Zagursky, et al., *Gene Anal. Tech.* 2: 89 (1985)) with reciprocal primers 5'-GTAAAACGACGGCCAGT-3' (SEQ ID NO 16) and 5'-CATGATTACGAATTCTA-3' (SEQ ID NO 17), which are compatible with the pUC plasmid. Sequencing reactions utilized modified T7 DNA polymerase (Sequenase, USB) and [$^{35}$S](α-thiophosphate) dATP and were analyzed by electrophoresis in a 6% polyacrylamide-8M urea gel. Nucleotide sequences of individual subclones were also obtained (not shown).

Analysis of the determined sequences indicated how genotype changes over the course of evolutionary history (not shown). From generation 0 to generation 3, variation is discarded throughout much of the catalytic core of the ribozyme. The mean number of mutations per subclone decreased from 7.0 at generation 0 to 2.7 at generation 3. By generation 3, a small number of mutations outside of the original zone of random mutation have occurred because of ongoing mutation events (not shown). The consensus sequence is still that of the wild type, although only one of 25 subclones has the entire wild-type sequence.

From generation 3 to generation 6, the dramatic accumulation of mutations at five positions within the ribozyme coincides with a three-fold improvement in the phenotype of the population as a whole. From generation 6 to generation 9, these positions are further accentuated and aggregate phenotype improves another three-fold. The mean number of mutations per subclone rises to 4.6 at generation 6 and to 5.9 at generation 9 as a larger proportion of subclones adopt the common mutations and as mutations accumulate outside of the original zone of random mutation.

The most frequent mutation is an A→Y (Y=U or C) change at position 94 (94:A→Y). This mutation is present, as A→U, in only 1 of 25 subclones at generation 3. At generation 6, there are 15 out of 25 occurrences, 12 as A→U and 3 as A→C; at generation 9, there are 35 out of 50 occurrences, 22 as A→U and 13 as A→C. Position 94 is unpaired in the secondary structure of the wild-type ribozyme (Burke, et al., *Nucleic Acids Res.* 15: 7217 (1987)). Considering the effect of site-directed mutations made at neighboring positions (Young, et al., *Cell* 67: 1007 (1991)), the 94:A→Y change may alter the orientation of ribozyme-bound substrate relative to the catalytic core of the molecule.

Another frequent mutation, occurring in 4 of 25 subclones at generation 3, 6 of 25 subclones at generation 6, and 22 of 50 subclones at generation 9, is a G→A change at position 215. This mutation converts a G·U wobble pair to an A·U Watson-Crick pair within the catalytic core of the ribozyme. Among 87 group I intron sequences that have been analyzed, 39 have a G·U and 28 have a G·C, but only 4 have an A·U at this location (Michel, et al., *J. Mol. Biol.* 216: 585 (1990)).

The most remarkable mutations are a G→U change at position 313 and an A→G change at position 314 that always occur together. These mutations are absent at generation 3, but are present in 5 of 25 subclones at generation 6 and 16 of 50 subclones at generation 9. The GA sequence normally at positions 313–314 is thought to form a short duplex structure (the 5' half of the P9.0 pairing) that draws the 3'-terminal guanosine residue of the ribozyme into the catalytic core (Michel, et al., *Nature* 342: 391 (1989); Michel, et al., *Genes Dev.* 4: 777 (1990)). The 3'-terminal guanosine was utilized as the nucleophile in the target phosphoester transfer reaction. The 313–314 mutations are expected to destroy the P9.0 pairing, yet confer selective advantage with respect to DNA cleavage (see below).

There is a frequent G→A change at position 312 that occurs only if the 313–314 mutations are not present. The 312:G→A change is present in 4 of 25 subclones at generation 3 and 8 of 25 subclones at generation 6, but only 5 of 50 subclones at generation 9. In terms of population frequency, the 312:G→A mutation declines as the 313–314:GA→UG mutations become more abundant.

F. Activity of Evolved Individuals

DNA from 14 subclones at generation 9 was transcribed to produce individual RNAs which were purified by polyacrylamide gel electrophoresis and Sephadex chromatography. The catalytic behavior of these RNAs was studied with [5'-$^{32}$P]- and [3'-$^{32}$P]-labeled DNA substrates having the sequence GGCCCTCTC-A$_3$(TA$_3$)$_3$ (SEQ ID NO 25) and with [5'-$^{32}$P]- and [α-$^{32}$p]-ATP-labeled RNA substrates having the sequence GGCCCUCUC-A$_3$(UA$_3$)$_3$ (SEQ ID NO 18). The kinetic parameter most relevant to our selection criterion was the proportion of ribozyme molecules that become joined to the 3' portion of the DNA substrate after 1 hour at 37° C. and 10 mM MgCl$_2$. These data and comparable data concerning reactions with a DNA substrate at 50° C. and 50 mM MgCl$_2$ and with an RNA substrate at 37° C. and 10 mM MgCl$_2$ were collected and plotted (data not shown).

The catalytic activity of 14 individual ribozymes obtained at generation 9 was determined (not shown). Ribozymes were transcribed and assayed according to the procedures described in subsection 4 above. RNA substrate was prepared by in vitro transcription with a synthetic oligodeoxynucleotide template; reaction conditions were as described previously for the data illustrated in FIG. 3, but included [α-$^{32}$P]ATP at 0.003 μCi/pmol to label the 3' portion of the substrate.

There was considerable heterogeneity among the 14 individual RNAs with respect to DNA cleavage activity in the target reaction. All were more active than the wild type, with the best (clones 29 and 23) being about 60 times more active. The five most active individuals were more active under physiologic conditions than under the high-temperature and high-MgCl$_2$ conditions. All 14 individuals showed improved activity with the RNA substrate, even though the population had never been challenged with RNA. Improved RNA cleavage activity was largely due to enhanced activity in the site-specific hydrolysis reaction (r=+0.93), which allowed enhanced turnover (data not shown).

As mentioned previously, there is selection pressure against site-specific hydrolysis of the EP covalent intermediate in the reaction with a DNA substrate. In fact, all but one of the 14 individuals showed decreased hydrolytic cleavage of the attached DNA compared to the wild type. All but one of the individuals show increased hydrolytic cleavage with the RNA substrate. Furthermore, there was a strong negative correlation (r=−0.93) between hydrolytic cleavage of DNA and RNA. The population was clearly divided into two groups: those with low DNA and high RNA hydrolysis activity, and those with high DNA and low RNA hydrolysis activity (not shown). All nine members of the former group carry the 313–314:GA→UG mutations, while all five members of the latter group lacked these changes.

Figure 6A:
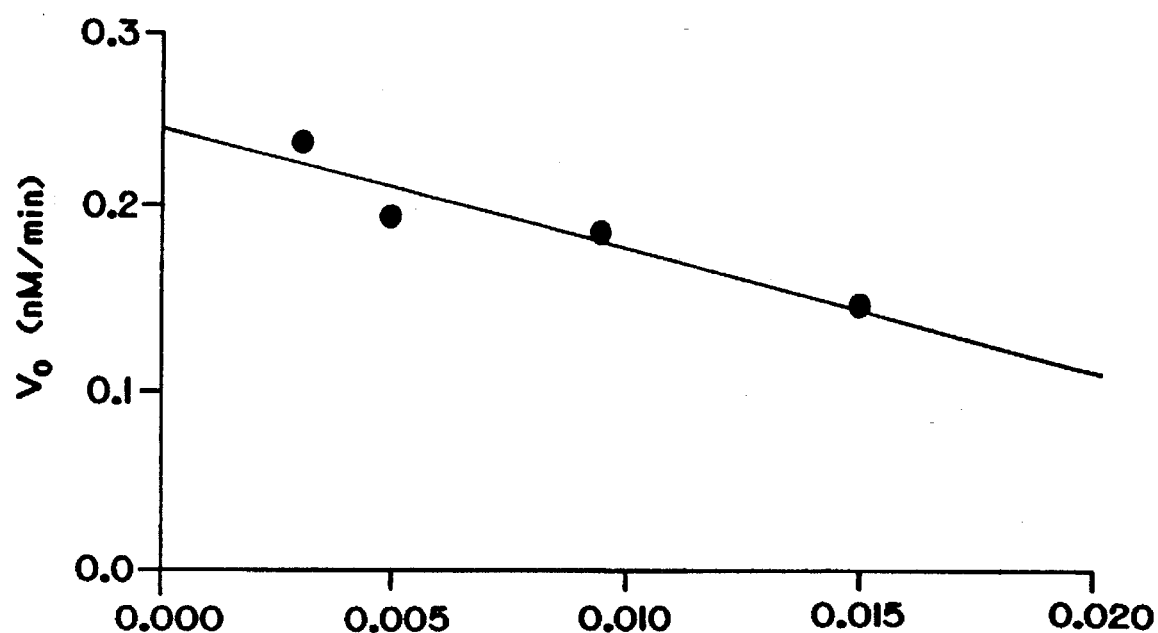
FIG. 6 illustrates Eadie-Hofstee plots used to determine $K_m$ (negative slope) and $V_{max}$ (y-intercept) for cleavage of (5'-$^{32}$P)-labeled d (GGCCCTCT-A$_3$ (TA$_3$)$_3$) (SEQ ID NO 6) by wild type ribozymes and clones 29 and 23 from generation 9. Closed circles represent the wild type; closed squares represent clone 29; and closed triangles represent clone 23. Each data point is the average of three independent determinations of initial velocity. The extent of the reaction was linear over the chosen time interval ($r_{min}$=0.94, $r_{avg}$=0.99).
Figure 6B:
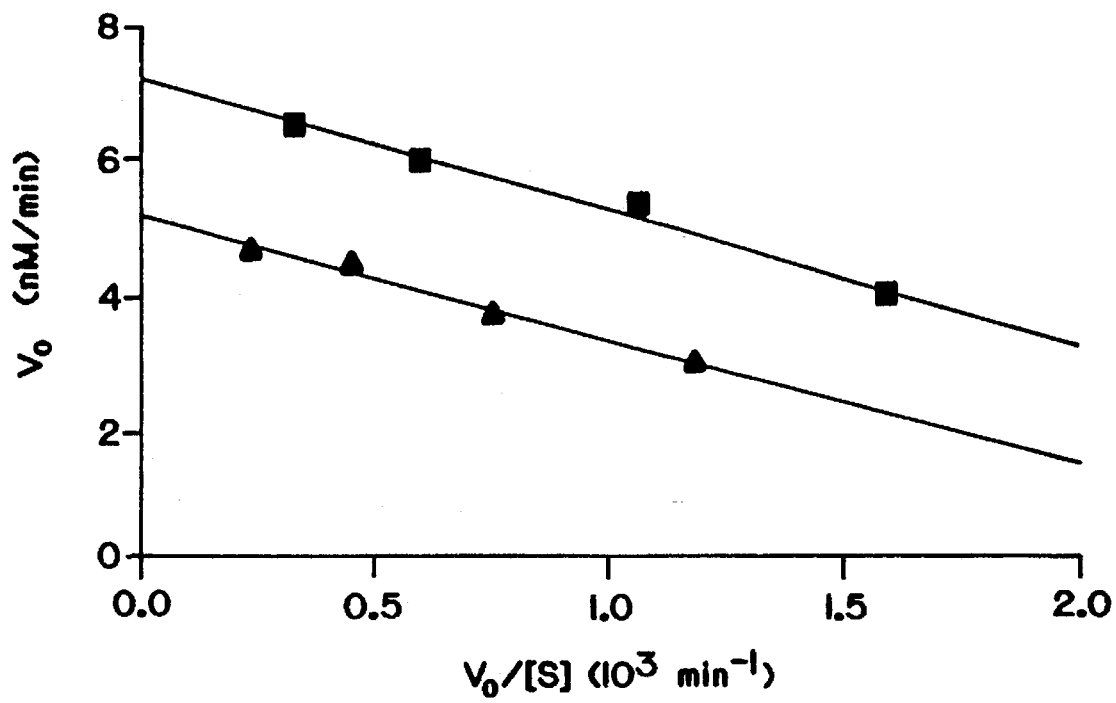

FIG. 6 illustrates Eadie-Hofstee plots used to determine $K_m$ (negative slope) and $V_{max}$ (y-intercept) for cleavage of (5'-$^{32}$P)-labeled d(GGCCCTCT-A$_3$(TA$_3$)$_3$) (SEQ ID NO 6) by wild type ribozymes and clones 29 and 23 from generation 9. Reaction conditions were as follows: 1 μM ribozyme, 10 mM MgCl$_2$, 30 mM EPPS (pH 7.5), 37° C.; for wild type 10, 20, 40 and 80 μM substrate at 0.25, 30, 60, 120, 180 and 240 minutes; for clone 29, 2.5, 5, 10, and 20 μM substrate at 0.25, 5, 10 and 15 minutes; for clone 23, 2.5, 5, 10 and 20 μM substrate at 0.25, 5, 10, 20 and 30 minutes. Ribozyme and substrate were first incubated separately in 10 mM MgCl$_2$, 30 mM EPPS (pH 7.5), 37° C., for 15 minutes, then mixed to start the reaction.

Closed circles represent the wild type; closed squares represent clone 29; and closed triangles represent clone 23.

Each data point is the average of three independent determinations of initial velocity. The extent of the reaction was linear over the chosen time interval ($r_{min}$=0.94, $r_{avg}$=0.99).

bond; reaction conditions were also as described in subsection 4 above.

TABLE 2

| Clone | Errors (N) | 94: A → Y | 98: C → U | 205: U → C | 215: G → A | 313–314: GA → UG | 317: U → R | 333: U → C | DNA cleavage $b_1$ | Hydrolysis $b_2$ | Accuracy $b_3$ |
|---|---|---|---|---|---|---|---|---|---|---|---|
| 29 | 6 | 1 | 0 | 0 | 1 | 1 | 0 | 0 | 65 | 0.1 | 0.7 |
| 23 | 7 | 1 | 0 | 0 | 1 | 1 | 0 | 0 | 57 | 0.1 | 0.6 |
| 30 | 8 | 1 | 0 | 0 | 1 | 1 | 1 | 0 | 48 | 0.1 | 0.8 |
| 43 | 8 | 1 | 0 | 0 | 1 | 1 | 0 | 1 | 32 | 0.0 | 0.4 |
| 5 | 7 | 1 | 0 | 0 | 0 | 1 | 0 | 0 | 22 | 0.1 | 0.4 |
| 37 | 4 | 0 | 0 | 0 | 1 | 1 | 0 | 0 | 21 | 0.1 | 0.6 |
| 28 | 5 | 0 | 1 | 0 | 0 | 1 | 0 | 0 | 15 | 0.0 | 0.7 |
| 2 | 5 | 0 | 0 | 0 | 0 | 1 | 0 | 0 | 11 | 0.0 | 0.8 |
| 42 | 6 | 1 | 0 | 0 | 1 | 0 | 0 | 0 | 7 | 0.7 | 0.8 |
| 8 | 8 | 1 | 0 | 1 | 0 | 1 | 0 | 0 | 3 | 0.2 | 1.1 |
| 40 | 1 | 0 | 0 | 0 | 1 | 0 | 0 | 0 | 3 | 0.9 | 0.6 |
| 12 | 6 | 0 | 1 | 1 | 0 | 0 | 1 | 0 | 3 | 0.7 | 0.8 |
| 27 | 2 | 1 | 0 | 0 | 0 | 0 | 0 | 0 | 3 | 0.8 | 0.6 |
| 11 | 6 | 1 | 1 | 0 | 0 | 0 | 0 | 1 | 3 | 1.2 | 0.8 |
| wt | 0 | 0 | 0 | 0 | 0 | 0 | 0 | 0 | 1 | 1.0 | 1.0 |
| $x_1$: | | 10 | 2 | –18 | 13 | 18 | 13 | –9 | | | |
| $x_2$: | | 0.4 | 0.7 | 0.2 | 0.4 | –0.4 | –0.2 | –0.1 | | | |
| $x_3$: | | 0.3 | 0.6 | 0.4 | 0.3 | 0.2 | –0.1 | –0.3 | | | |
| avg.[1] | 5.6 | 0.6 | 0.2 | 0.1 | 0.5 | 0.6 | 0.1 | 0.1 | 21 | 0.3 | 0.7 |
| G9[2] | 5.9 | 0.7 | 0.1 | 0.2 | 0.4 | 0.3 | 0.1 | 0.2 | 21 | 0.3 | 0.6 |

[1] Avg. = the average of the 14 individuals
[2] G9 genotype is the average of the 50 subclones obtained from the 9th generation; G9 phenotype is the behavior of the G9 population as a whole Clones 29 and 23 were chosen for more detailed kinetic analysis, for comparison with the wild-type ribozyme. Initial rates were determined for the reaction with [5'-$^{32}$P]-labeled d (GGCCCTCT-A$_3$(TA$_3$)$_3$) (SEQ ID NO 6) substrate at 37° C. and 10 mM MgCl$_2$, with 1 μM ribozyme and excess substrate. An Eadie-Hofstee plot of $v_0$ as a function of $v_0$/[S] was used to obtain $V_{max}$ and $K_m$ (FIG. 6). From this data, $k_{cat}$ and $k_{cat}/K_m$ were calculated. For the wild-type ribozyme, $K_m$=6.6 μM and $k_{cat}$=0.0002 min$^{-1}$ ($k_{cat}/K_m$= 36M$^{-1}$ min$^{-1}$). This compares to $K_m$=30 μM and $k_{cat}$=0.006 min$^{-1}$, previously reported for the wild-type ribozyme in a related reaction at 50° C. and 10 mM MgCl$_2$ (Herschlag, et al., Id. (1990)). For clone 29, $K_m$=2.0 μM and $k_{cat}$=0.007 min$^{-1}$ ($k_{cat}/K_m$=3600M$^{-1}$min$^{-1}$); for clone 23, $K_m$=1.9 μM and $k_{cat}$=0.005 min$^{-1}$ ($k_{cat}/K_m$=2700M$^{-1}$ min$^{-1}$) (data obtained at 37° C. and 10 mM MgCl$_2$). Thus, the catalytic efficiency of the two evolved RNAs was increased and was about 100 times greater than that of the wild type, because of improvement in both $K_m$ and $k_{cat}$.

G. Correlating Genotype and Phenotype

The relation between genotype and phenotype in the context of an RNA-based evolving system can now be formalized. Genotype can be represented as a matrix A, the rows corresponding to individuals in the population and the columns corresponding to functionally significant positions within the nucleotide sequence (Table 2).

Table 2 shows the genotype and phenotype of 14 individuals from generation 9. Genotype is represented as a binary matrix (shown in brackets). Phenotype is represented as a column vector $b_1$, with values normalized to wild type=1.0. DNA cleavage and hydrolysis activity were determined with [3'-$^{32}$P]-labeled DNA substrate under physiologic conditions, as described in subsection 4 above. Accuracy was determined with [5'-$^{32}$P]-labeled DNA substrate under physiologic conditions, measuring the fraction of substrate cleavage that occurs at the target phosphodiester bond; reaction conditions were also as described in subsection 4 above.

As shown in Table 2, phenotype can be represented as a column vector b, whose entries are some measure of fitness (catalytic behavior) of the various individuals. One then seeks a row vector x that provides a best fit to the equation: Ax=b, that is, provides a best fit linear estimation of the relation between genotype and phenotype. The solution that minimizes the least-squares error is: x=(A*A)$^{-1}$ A*b, where A* is the transpose of A. In this way, one obtains a weighing vector x that provides an estimate of phenotype for any given genotype (Table 2).

The data obtained from 14 individuals is not sufficient to provide a meaningful solution to the relation of genotype to phenotype, even for those nucleotide positions that are known to be most significant based on their high frequency of accepted mutation. The weighing vector x is used as a guide to help decide which mutations are sufficiently important to warrant individual study.

The following individual mutations were prepared by site-directed mutagenesis: 94:A→U, 94:A→C, 215:G→A, 313:G→U, 314:A→G, and 313–314:GA→UG. Catalytic activity was studied with d(GGCCCTCT-A$_3$(TA$_3$)$_3$[5'-$^{32}$P] A) (SEQ ID NO 13) substrate.

Site-directed mutagenesis was carried out essentially as described in Morinaga, et al., Biotechnology 2: 636 (1984), which may be described as follows. Plasmid pT7L-21 (Zaug, et al., Biochemistry 27: 8924 (1988)) was digested with either (i) Eco RI and Hind III to remove the ribozyme coding region, or (ii) Bsa I and Xmn I to remove the ampicillin-resistance gene. The resulting fragments were purified in a 1% agarose gel and cross-hybridized in the presence of a 5'-phosphorylated synthetic oligodeoxynucleotide that introduces the desired mutation. The annealing mixture contained 0.06 pmol of pT7L-21(ΔEco-Hind), 0.06 pmol pT7L-21(ΔBsa-Xmn), 15 pmol of mutagenic oligodeoxynucleotide, 40 mM Tris-HCl (pH 7.2), and 8 mM MgSO$_4$ in 12-μl volume, which was heated to 100° C. for three minutes, then incubated at 30° C. for 30 minutes, and 0° C. for 10 minutes.

The annealing product was made fully double-stranded with the Klenow fragment of E. coli DNA polymerase I (Boehringer-Mannheim, Indianapolis, Ind.) and T4 DNA ligase (U.S. Biochemical, Cleveland, Ohio) and then used to transform competent DH5α-F' cells, which were grown on ampicillin-containing plates. Colonies were screened by the colony hybridization method with [5'-$^{32}$P]-labeled mutagenic oligodeoxynucleotide as a probe (Grunstein, et al., *PNAS USA* 72: 3961 (1975)). DNA was prepared from positive colonies and sequenced throughout the ribozyme gene, as described above.

RNA was prepared by in vitro transcription, essentially as follows. Transcription conditions: 2 pmol of DNA template (containing mutagenic oligodeoxynucleotides), 2 mM nucleotide triphosphates (NTPs), 15 mM MgCl$_2$, 2 mM spermidine, 5 mM dithiothreitol (DTT), 50 mM tris-HCl (ph 7.5), 1500 U of T7 RNA polymerase; 60 µl volume; 37° C., 2 hours. RNA was purified by electrophoresis in a 5% polyacrylamide-8M urea gel and subsequent column chromatography on Sephadex G-50.

The individual mutations result in improved activity compared to the wild type, but they do not result in activity exceeding that of the generation 9 population as a whole. Data were obtained regarding the DNA cleavage activity of individuals obtained by site-directed mutagenesis (not shown). Reaction conditions were as described in subsection 4 hereinabove, relating to FIG. 5. The symbol (−) indicates absence of enzyme, while G9 represents generation 9 population as a whole. Reaction products were separated in a 20% polyacrylamide-8M urea gel, an autoradiogram of which is shown.

Activity in the 94:A→U mutant is seven times greater and in the 94:A→C mutant it is two times greater than in the wild type. The 313–314:GA→UG double mutant is more active than either the 313:G→U or 314:A→G single mutant, explaining why the 313–314 mutations occur together among the evolved individuals examined herein. As predicted from the analysis of 14 individuals at generation 9, the 313–314:GA→UG mutations result in diminished site-specific hydrolysis of the DNA substrate compared to the wild type. These mutations confer both enhanced phosphoester transfer activity and diminished site-specific hydrolysis activity, and thus are well suited to meet the imposed selection constraint which depends on availability of the EP covalent intermediate.

H. Extension of Directed Evolution to Develop Other Evolved Species

As an in vitro model of Darwinian evolution, a population of macromolecular catalysts was directed toward the expression of novel catalytic function. In the present Example, the development of ribozymes that cleave DNA with improved efficiency under physiologic conditions has been demonstrated. These evolved RNAs were also used to cleave a target DNA in vivo; ribozymes obtained from generation 9 were expressed in *E. coli* and shown to prevent infection by M13 single-stranded DNA bacteriophage (not shown).

The present successful phylogeny has been continued beyond the tenth generation, after decreasing the concentration of DNA substrate in the target reaction, as further described in Example 2 hereinbelow. Through the first ten generations the substrate concentration was 10 µM, roughly matching the K$_m$ for the wild type. Now that the evolved individuals have attained a K$_m$ of about 2 µM, the substrate concentration has been reduced to subsaturating levels to promote further improvement in substrate binding. In addition, catalytic turnover in the DNA cleavage reaction is being improved by selecting for both phosphoester transfer activity, which generates the EP covalent intermediate, and subsequent RNA-catalyzed site-specific hydrolysis activity, which frees the ribozyme to act on another substrate molecule.

The selection scheme used herein may be applied to various substrates of the form: d(CCCTCNA$_3$(TA$_3$)$_3$) (SEQ ID NO 19), where N refers to a nucleotide analog and the ribozyme is selected for its ability to cleave the phosphodiester bond following the sequence CCCTCN (SEQ ID NO 20). Examples of nucleotide analogs useful according to the present invention include those listed in the following Table, most of which are found in the approved listing of modified bases at 37 CFR §1.822 (which is incorporated herein by reference).

TABLE 3

| Abbreviation | Nucleotide Analogs Description |
|---|---|
| ac4c | 4-acetylcytidine |
| chm5u | 5-(carboxyhydroxylmethyl)uridine |
| cm | 2'-O-methylcytidine |
| cmnm5s2u | 5-carboxymethylaminomethyl-2-thioridine |
| d | dihydrouridine |
| fm | 2'-O-methylpseudouridine |
| galq | β,D-galactosylqueosine |
| gm | 2'-O-methylguanosine |
| i | inosine |
| i6a | N6-isopentenyladenosine |
| m1a | 1-methyladenosine |
| m1f | 1-methylpseudouridine |
| m1g | 1-methylguanosine |
| m1l | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| manq | β,D-mannosylmethyluridine |
| mcm5s2u | 5-methoxycarbonylmethyluridine |
| mo5u | 5-methoxyuridine |
| ms2i6a | 2-methylthio-N6-isopentenyladenosine |
| ms2t6a | N-((9-β-D-ribofuranosyl-2-methylthiopurine-6-yl)carbamoyl)threonine |
| mt6a | N-((9-β-D-ribofuranosylpurine-6-yl)N-methyl-carbamoyl)threonine |
| mv | uridine-5-oxyacetic acid methylester |
| o5u | uridine-5-oxyacetic acid (v) |
| osyw | wybutoxosine |
| p | pseudouridine |
| q | queosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-β-D-ribofuranosylpurine-6-yl)carbamoyl)threonine |
| tm | 2'-O-methyl-5-methyluridine |
| um | 2'-O-methyluridine |
| ym | wybutosine |
| x | 3-(3-amino-3-carboxypropyl)uridine, (acp3)u |
| araU | β,D-arabinosyl |
| araT | β,D-arabinosyl |

Nucleotide analogs that are particularly useful in the enzymatic RNA molecules, nucleotide substrates, and methods disclosed herein include those having the abbreviations cm, d, gm, i, p, s2c, s2u, s4u, t, um, araU, and araT. (The more complete names of these analogs are shown in the foregoing Table 3.)

The substrate need not be a nucleotide or nucleotide analog. The only requirement is that RNAs that react with the substrate become tagged in some way so that they can be distinguished from nonreactive molecules with respect to the amplification process. For example, reactive RNAs could become joined to a portion of the substrate that is attached to a solid support, while nonreactive RNAs would be washed away, leaving the bound RNAs to be selectively amplified. These and other methodologies are further described below.

Example 2

Optimization of a DNA-Cleaving Enzymatic RNA Molecule

A. Optimization and Selection Criteria

In a previous analysis (see Example 1), an in vitro evolution procedure was used to obtain variants of the Tetrahymena ribozyme with 100-fold improved ability to cleave a target single-stranded DNA under physiologic conditions. Reported herein is the continuation of the in vitro evolution process to achieve $10^5$-fold overall improvement in DNA-cleavage activity. In addition, it is demonstrated herein that, by appropriate manipulation of the selection constraints, one can optimize specific catalytic properties of the evolved ribozymes.

The concentration of the DNA substrate was first reduced 50-fold, to favor ribozymes with improved substrate binding affinity. Next, the reaction time was reduced 12-fold to favor ribozymes with improved catalytic rate. In both cases, the evolving population responded as expected, first improving substrate binding 25-fold, and then improving catalytic rate about 50-fold. The population of ribozymes has undergone 27 successive generations of in vitro evolution, resulting in, on average, 17 mutations relative to the wild-type that are responsible for the improved DNA-cleavage activity.

In vitro selection and in vitro evolution techniques allow new catalysts to be isolated without a priori knowledge of their composition or structure. Such methods have been used to obtain RNA enzymes with novel catalytic properties. Ribozymes that undergo autolytic cleavage with lead cation have been derived from a randomized pool of tRNA$^{Phe}$ molecules (Pan & Uhlenbeck, *Biochemistry* 31: 3887–3895 (1992)). Group I ribozyme variants have been isolated that can cleave DNA (Beaudry & Joyce, *Science* 257: 635–641 (1992)) or that have altered metal dependence (Lehman & Joyce, *Nature* 361: 182–185 (1993)). Starting with a pool of random RNA sequences, molecules have been obtained that catalyze a polymerase-like reaction (Bartel & Szostak, *Science* 261: 1411–1418 (1993)). In the present example, refinement of specific catalytic properties of an evolved enzyme via alteration of the selection constraints during an in vitro evolution procedure is described.

The within-described examples utilize derivatives of the self-splicing group I intron of *Tetrahymena thermophila*, a ribozyme that is able to catalyze sequence-specific cleavage of single-stranded RNA via a phosphoester transfer mechanism (Zaug & Cech, *Science* 231: 470–475 (1986); Zaug et al., *Nature* 324: 429–433 (1986)), although it is expressly to be understood that the invention is not limited to these embodiments. The ribozyme contains a template region, referred to as the "internal guide sequence" (IGS), which lies at the 5' end of the molecule and forms Watson-Crick base pairs with the target RNA substrate. The 3'-OH of guanosine, including a guanosine residue that lies at the 3' end of the ribozyme, is directed to attack a particular phosphoester bond within the ribozyme-bound substrate. A phosphoester transfer reaction ensues, resulting in cleavage of the substrate at a position immediately downstream from the region of base pairing, and concomitant ligation of the 3' portion of the substrate to the 3' oxygen of the attacking guanosine. The wild-type Tetrahymena ribozyme can cleave a single-stranded DNA substrate with low efficiency under conditions of high magnesium concentration (50 mM MgCl$_2$) and/or high temperature (50° C.) (Herschlag & Cech, *Nature* 344: 405–409 (1990a); Robertson & Joyce, *Nature* 344: 467–468 (1990)). Under more physiologic conditions (e.g. 37° C., 10 mM MgCl$_2$, pH 7.5), however, the DNA-cleavage reaction is almost undetectable.

Figure 7:
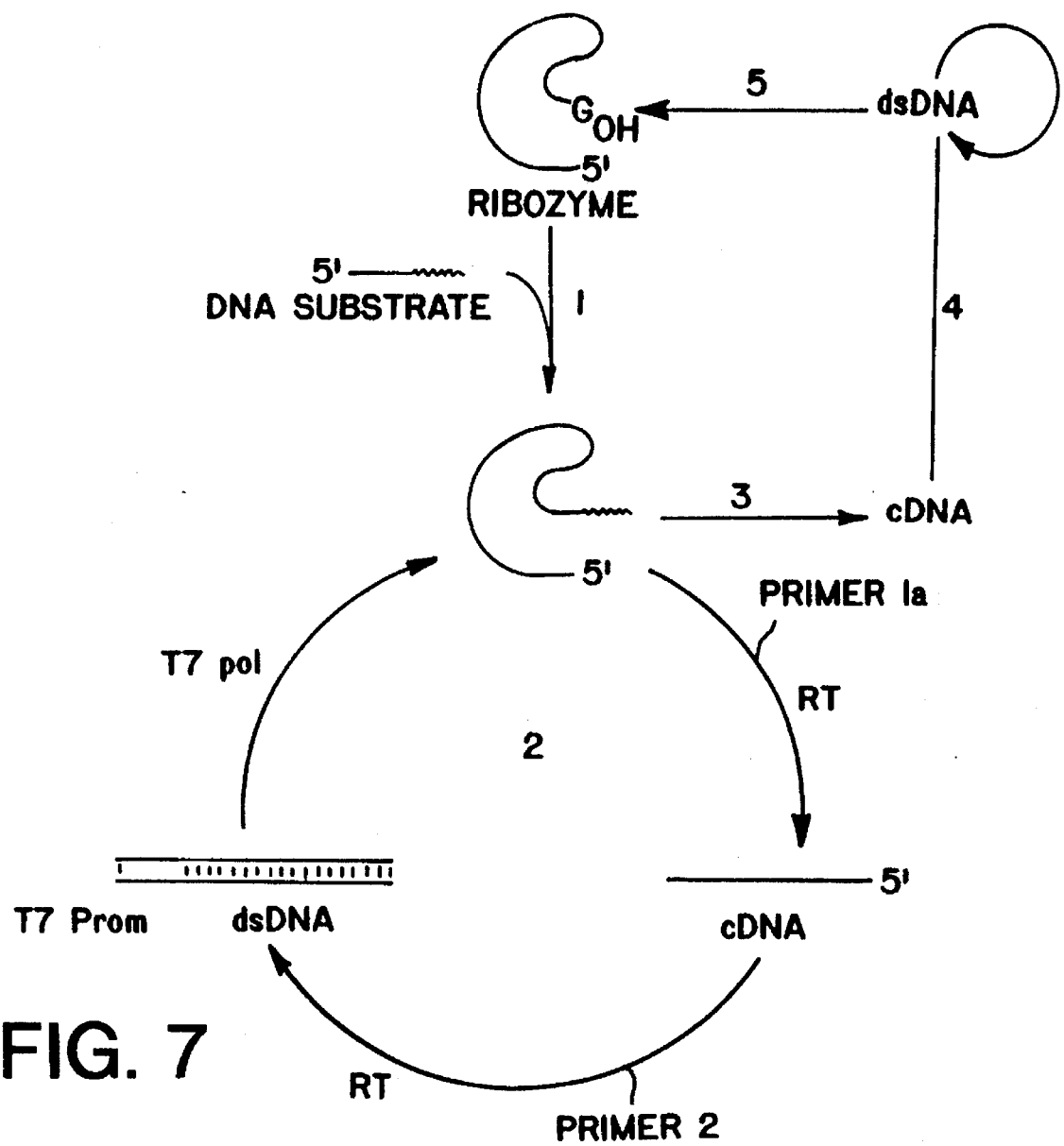
FIG. 7 illustrates the overall in vitro evolution procedure disclosed herein. 1—Cleavage of the DNA substrate via phosphoester transfer results in ligation of the 3' portion of the substrate to the 3' end of the ribozyme. 2—Selective isothermal amplification of DNA-cleaving ribozymes: first, selective Primer 1a hybridizes to the extended 3' terminus of active molecules and initiates cDNA synthesis in the presence of reverse transcriptase (RT); next, Primer 2, which contains a T7 promoter sequence, hybridizes to the cDNA and initiates second-strand DNA synthesis; finally, T7 RNA polymerase (T7 pol) produces multiple copies of the selected RNA, each of which can enter a new round of amplification. 3—Selective cDNA synthesis employing Primer 1a and reverse transcriptase. 4—PCR amplification employing nonselective Primer 1b and Primer 2, restores the original terminus of the ribozyme-encoding gene and introduces occasional mutations. 5—In vitro transcription to produce the progeny population of ribozymes.

An in vitro evolution procedure that may be used to obtain variants of the Tetrahymena ribozyme that can cleave DNA under physiologic conditions with improved efficiency compared to the wild-type (FIG. 7). (See also Beaudry and Joyce (*Science* 257: 635–641 (1992).) At the beginning of this procedure, a population of ribozyme variants was generated by partially randomizing the phylogenetically conserved portions of the molecule that are known to be essential for catalytic activity. Superior DNA-cleaving ribozymes were distinguished from less active molecules based on the likelihood of attachment of the 3' portion of the substrate to the 3' end of the ribozyme. A DNA primer was hybridized across the ligation junction of successful reaction products, and used to initiate a selective isothermal amplification reaction (see FIG. 7, bottom). The selectively amplified molecules then served as templates for cDNA synthesis; the resulting cDNA was amplified by the polymerase chain reaction (PCR) (Saiki et al, *Science* 230: 1350–1354 (1985); Saiki et al, *Science* 239: 487–491 (1988)); and the PCR products were transcribed to generate a new pool of RNAs. The entire process, beginning with the cleavage reaction and followed by selective isothermal amplification, cDNA synthesis, PCR amplification, and in vitro transcription, constitutes one "generation" of the in vitro evolution procedure.

This in vitro procedure has successfully been used to generate 10 successive generations, starting with a pool of $10^{13}$ variants of the Tetrahymena ribozyme (see Example 1 above, and FIG. 7). After the 9th generation (G9), individual ribozymes were isolated from the population and shown to catalyze the cleavage of a DNA substrate 100-fold more efficiently compared to the wild-type enzyme. This modest improvement in catalytic efficiency resulted from both an increased catalytic rate ($k_{cat}$) and a decreased value for the Michaelis constant ($K_M$). The outcome, however, was somewhat dissatisfying because the ribozymes were still inefficient catalysts in an absolute sense, with $k_{cat}/K_M$ on the order of $10^3 M^{-1} min^{-1}$.

For each generation, the evolving population was provided with 10 μM DNA substrate and allowed 1 hr to carry out the DNA-cleavage reaction. By G9, $K_M$ had improved from 6 μM for the wild-type to about 2 μM for the evolved individuals (see Example 1; see also Beaudry & Joyce, *Id.*, (1992)). Accordingly, it appeared that the population was no longer under stringent selection pressure to drive further improvement of $K_M$. Individual cleavage rates, on the other hand, were on the order of 0.007 min$^{-1}$ by G9, still slow enough to be constrained by the 1 hr incubation period. However, if the reaction rate continued to improve, then the selection constraints would eventually become insufficient to favor further improvement of the catalytic rate. Apparently, additional generations of in vitro evolution, under different selection constraints, would be necessary to obtain substantially greater DNA-cleavage activity.

In the present example, in vitro evolution techniques were applied with a higher level of sophistication and control. Because the outcome of an in vitro evolution experiment depends on the nature of the selection constraints, specific catalytic properties of a ribozyme, such as substrate binding affinity, catalytic rate, substrate specificity, and turnover, might be improved by appropriate manipulation of the reaction conditions. With this in mind, optimization of two catalytic properties of the DNA-cleaving ribozymes, namely, substrate binding affinity and catalytic rate was a primary goal. It was hypothesized herein that ribozymes with the greatest affinity for the substrate would enjoy a selective advantage when the substrate is presented at low concentrations. Under saturating conditions, ribozymes with the fastest first-order rate of reaction would be favored when the reaction time is very short.

The previously-characterized G9 population of DNA-cleaving ribozymes (see Example 1) was "resurrected" and 27 additional generations of in vitro evolution were carried out under somewhat different reaction conditions. From generations 10 through 18, the substrate concentration was reduced 50-fold, from 10 μM to 0.2 μM. From generations 19 through 27, the lower substrate concentration was maintained and the reaction time was reduced 12-fold, from 1 hr to 5 min. On the basis of binding and kinetic studies, the population of ribozymes responded to each alteration of the selection constraints as predicted, becoming enriched with tighter substrate binders during generations 10–18, and then with faster catalysts during generations 19–27. Generations 28–36 are discussed in subsection 6 hereinbelow.

B. Materials and Methods

1. Materials

Unlabeled nucleoside triphosphates (NTPs) and deoxynucleoside triphosphates (dNTPs) were purchased from Pharmacia, and dideoxynucleoside triphosphates (ddNTPs) were from U.S. Biochemical (USB, Cleveland, Ohio). [a-$^{32}$P]GTP, [g-$^{32}$P]ATP, and [$^3$H]UTP were from ICN Radiochemicals. Synthetic oligodeoxynucleotides were obtained from Operon Technologies and purified by polyacrylamide gel electrophoresis and subsequent chromatography on Sephadex G-25. Restriction enzymes and T4 polynucleotide kinase were from New England Biolabs (Beverly, Mass.), calf intestine phosphatase from Boehringer (Indianapolis, Ind.), AMV reverse transcriptase from Life Sciences (St. Petersburg, Fla.), MoMLV reverse transcriptase and Sequenase 2.0 (modified T7 DNA polymerase) from U.S. Biochemical, and Taq DNA polymerase from Cetus (Emeryville, Calif.). T7 RNA polymerase was prepared as previously described (Davanloo et al., *PNAS USA* 81: 2035–2039 (1984)) and purified according to a procedure originally developed for SP6 RNA polymerase (Butler & Chamberlain, *J. Biol. Chem.* 257: 5772–5778 (1982)).

2. Preparation of Wild-Type Ribozyme

The L-21 form of the Tetrahymena ribozyme was prepared by in vitro transcription of Hind III-digested pT7L-21 plasmid DNA (Zaug et al., *Biochemistry* 27: 8924–8931 (1988)). The transcription reaction mixture contained 0.1 μg/μl of plasmid, 15 mM MgCl$_2$, 2 mM spermidine, 50 mM Tris (pH 7.5), 5 mM DTT, 2 mM each NTP, 0.005 U/μl inorganic pyrophosphatase, and 25 U/μl T7 RNA polymerase, incubated at 37° C. for 2 hr. The 23-nucleotide 3' exon sequence was removed by RNA-catalyzed site-specific hydrolysis (Inoue et al., *J. Mol. Biol.* 189: 143–165 (1986)): RNA was incubated in the presence of 50 mM CHES (pH 9.0) and 10 mM MgCl$_2$ at 42° C. for 1 hr. The resulting RNA was isolated by electrophoresis in a 5% polyacrylamide/8M urea gel, visualized by UV shadowing, eluted from the gel overnight at room temperature in a buffer containing 200 mM NaCl, 10 mM Tris (pH 7.5), and 0.5 mM EDTA, and purified by affinity chromatography on DuPont Nensorb (Wilmington, Del.). The concentration of ribozyme was determined spectrophotometrically, based on $e_{260}$=3.2×10$^6$ M$^{-1}$ cm$^{-1}$ (Zaug et al., *Biochemistry* 27: 8924–8931 (1988)).

3. In Vitro Evolution Procedure

In vitro evolution was carried out as described previously (see Example 1 above) and as depicted in FIG. 7. While polymerase chain reaction (PCR) or self-sustained sequence replication (3SR) methods are both useful, the within-described methodology most closely resembles the 3SR method (see, e.g., Guatelli et al., *PNAS USA* 87: 1874–1878 (1990)). The 3SR system is particularly useful in the detection and nucleotide sequence analysis of rare RNAs and DNAs.

The population of DNA-cleaving ribozymes obtained after 9 generations of in vitro evolution in Example 1 above was used as starting material. Ribozymes (0.1 μM) and DNA substrate (0.2 μM) were incubated at 37° C. for 1 hr in a 100 μl volume containing 10 mM MgCl$_2$ and 30 mM EPPS (pH 7.5). After ethanol precipitation, a portion of the reaction products (10–50%) was added to a 20 μl isothermal amplification reaction mixture, containing 10 mM MgCl$_2$, 80 mM KOAc, 50 mM Tris (pH 7.5), 5 mM DTT, 2 mM each NTP, 0.2 mM each dNTP, 4 μCi [a-$^{32}$P]GTP, 12.5 U/μl MoMLV reverse transcriptase, 50 U/μl T7 RNA polymerase, and 20 pmol each of 5'-TTTATTTATTTATTT-3' (Primer 1a, SEQ ID NO 21) and 5'-CTGCAGAATTCTAATACGACTCAC-TATAGGAGGGAAAAGTTATCAGGC-3' (Primer 2, SEQ ID NO 15), which was incubated at 37° C. for 2 hr. Primer 1 hybridizes to the 3' portion of the substrate that becomes attached to the 3' end of the ribozyme. (Primers 1a and 1b, when used, perform similarly.) Primer 2 hybridizes to the 3' end of the resulting cDNA and introduces the T7 promoter sequence.

Twenty-five percent of the isothermal amplification products were used to generate cDNA in a 20 μl reaction mixture containing 10 mM MgCl$_2$, 50 mM Tris (pH 7.5), 5 mM DTT, 2 mM each NTP, 0.2 mM each dNTP, 0.2 U/μl AMV reverse transcriptase and 20 pmol Primer 1a, incubated at 37° C. for 1 hr. Approximately 5–10% of the resulting cDNA was amplified by the PCR in a 100 μl reaction mixture containing 1.5 mM MgCl$_2$, 50 mM KCl, 10 mM Tris (pH 8.3), 0.1% gelatin, 0.2 mM each dNTP, 20 pmol 5'-CGAGTACTC-CAAAACTAATC-3' (Primer 1b, SEQ ID NO 9), 20 pmol Primer 2, and 2.5 U Taq DNA polymerase, carried out for 30 cycles of 92° C. for 1 min, 45° C. for 1 min, and 72° C. for 1 min, and 1 cycle of 72° C. for 10 min. Primer 1b is complementary to the 3' end of the ribozyme, allowing regeneration of its original, active form. PCR DNA (~250–500 ng, 5–10% of the total) then served as template in an in vitro transcription reaction, carried out in a 25–50 μl volume.

The transcribed RNA was isolated by polyacrylamide gel electrophoresis, visualized by UV shadowing, cut and eluted from gel, purified on dupont Nensorb (duPont de Nemours, Wilmington, Del.), and quantified spectrophotometrically, as described above. The entire process was repeated 18 times, the first 9 as described above and the second 9 with the incubation time for the cleavage reaction reduced from 1 hr to 5 min. Occasionally, the cDNA was purified to improve the quality of the PCR amplification. To do so, cDNA was synthesized as above except in the presence of 25–50 μCi [a-$^{32}$P]dATP. Labeled cDNA was isolated by electrophoresis in a 5% polyacrylamide/8M urea gel, visualized by autoradiography, cut and eluted from gel, and purified on DuPont Nensorb.

4. Shotgun Cloning, Sequencing, and Preparation of Individual Enzymatic RNA Molecules The G18 subclones were obtained as previously described (see Example 1 above). The G27 subclones were obtained using the Invitrogen TA Cloning Kit (Invitrogen, San Diego, Calif.). The PCR DNA at G27 was ligated into a linearized plasmid, and the resulting DNA was used to transform competent INVaF' cells, which were grown on ampicillin/

X-gal plates. Individual colonies containing the insert were identified by their white color, chosen at random, and grown overnight in liquid media. Plasmid DNA was prepared by the boiling, lysis method (Holmes & Quigley, *Anal. Biochem.* 114: 193–197 (1981)) and screened for the presence of insert by restriction digestion. Cloned individuals were sequenced by the dideoxy chain-termination method, as previously described (Sanger et al., *PNAS USA* 74: 5463–5467 (1977); Beaudry a Joyce, *Id.* (1992)). Complete sequences of individual subclones are available upon request. Individual ribozymes were prepared as follows: the gene encoding the ribozyme was amplified by the PCR using Primer 1b and Primer 2; the resulting DNA was used as a template for in vitro transcription; the RNA products were isolated by polyacrylamide gel electrophoresis, and were purified and quantified as described above.

5. Preparation of Substrate and Product Oligonucleotides

The DNA substrate 5'-GGCCCTCTATTTATTTA-3' (SEQ ID NO 22) and DNA product 5'-GGCCCTCT-3' (SEQ ID NO 23) were (5'-$^{32}$P)-labeled in a 20 μl reaction mixture containing 20 pmol oligonucleotide, 10 pmol (4.5 μCi/pmol) [g-$^{32}$P]ATP, 5 mM MgCl$_2$, 25 mM CHES (pH 9.0), 3 mM DTT, and 1.25 U/μl T4 polynucleotide kinase, incubated at 37° C. for 1 hr. Labeled oligonucleotide was isolated by electrophoresis in a 20% polyacrylamide/8M urea gel, visualized by autoradiography, eluted from the gel, and purified on DuPont Nensorb.

The RNA substrate 5'-GGCCCUCUAUUUAUUUA-3' (SEQ ID NO 24) was prepared by in vitro transcription using a partially single-stranded synthetic DNA template (Milligan et al., *Nucleic Acids Res.* 15: 8783–8798 (1987)), as described previously (Example 1). The RNA transcript was dephosphorylated with calf intestine phosphatase, extracted with phenol and chloroform, and then (5'-$^{32}$P)-labeled and purified as described above.

6. Kinetics Analysis

All cleavage reactions were carried out at 37° C. in 10 mM MgCl$_2$, 30 mM EPPS (pH 7.5), and 40 μg/μl BSA, using (5'-$^{32}$P)-labeled substrate. BSA was added to prevent oligonucleotides from adhering to the walls of the 500 μl Eppendorf tubes, and did not affect the course of the reaction. Ribozyme and substrate were preincubated separately for 15 min at 37° C., and then mixed to initiate the reaction. Typically, 5 aliquots of 3–10 μl each were removed from the reaction mixture at specified times and quenched by addition to 1–2 volumes of an ice-cold mixture containing 8M urea, 50–100 mM EDTA, 0.05% xylene cyanol, 0.05% bromophenol blue, 10% SDS, 9 mM Tris-borate (pH 8.3), and 20% sucrose. Substrate and product were separated by electrophoresis in a 20% polyacrylamide/8M urea gel, visualized by auto-radiography, excised from gel, and quantified by Cerenkov counting.

$K_M$ and $k_{cat}$ values were determined in experiments with substrate (S) in excess over ribozyme (E). Initial rates of reaction ($v_o$), over a range of substrate concentrations, were estimated from the initial linear phase, generally the first 5% or less of the reaction. Typically 8 data points were fit by a least squares method to a theoretical line given by the equation: $v = ^-K_M (v_o/[S]) + V_{max}$.

Single-turnover experiments were performed with ribozyme in excess of substrate (Herschlag & Cech, *Biochemistry* 29: 10159–10171 (1990b)). Initial rates ($k_{obs}$) were obtained using no more than the first 5% of the reaction. Given that $k_{cat}/K_M = k_{obs}/[E]$, each $k_{obs}$ value, obtained at different ribozyme concentrations, provided an estimate of $k_{cat}/K_M$. Generally 8 or more measurements of $k_{cat}/K_M$ were obtained.

7. Determination of Binding Constants

The equilibrium dissociation constant, $K_D$, of the complex between ribozyme and DNA product (P) was determined by gel-shift analysis in a native polyacrylamide gel (Pyle et al., *PNAS USA* 87: 8187–8191 (1990)). Ribozyme at twice final concentration was preincubated at 37° C. for 15 min in 10 mM MgCl$_2$ and 30 mM EPPS (pH 7.5) before mixing with an equal volume of 0.05–1 nM (5'-$^{32}$P)-labeled DNA product in 10 mM MgCl$_2$, 30 mM EPPS (pH 7.5), 0.05% xylene cyanol, 3% glycerol, and 80 μg/μl BSA. The mixture was allowed to equilibrate at 37° C. for 15–60 min before loading on a 10% polyacrylamide gel containing 10 mM MgCl$_2$ and 30 mM EPPS (pH 7.5). The electrophoresis buffer also contained 10 mM MgCl$_2$ and 30 mM EPPS (pH 7.5). The gel was run at 6 milliamps in a 37° C. room until the sample had entered the gel (~10 min), and then moved into a 4° C. cold room where the current was increased to 30 milliamps. This was done to prevent the temperature of the gel from rising above 37° C. The ribozyme-product complex and free product were visualized by autoradiography, cut from the gel, and quantified by Cerenkov counting.

A binding curve was generated by plotting the percentage of product bound to ribozyme (% bound) over a range of ribozyme concentrations. $K_D$ was determined by fitting the data to a theoretical binding curve using a least squares method. Because ribozyme was in vast excess over product, the theoretical binding curve could be represented by the equation: $\% \text{ bound} = [E]/([E]+K_D)$, where $K_D = [E]$ when half of the total product is bound to the ribozyme.

C. Results

1. Evolution In Vitro

Beginning with the 9th generation (G9) population of ribozymes obtained in a previous study (Beaudry & Joyce, *Id.* (1992)), 18 additional generations of in vitro evolution were carried out. Variation in the population was maintained by PCR amplification, which introduces mutations at a rate of ~0.1% per nucleotide position per generation. Because mutation is ongoing, evolution based on Darwinian principles can occur. Progeny ribozymes have the opportunity to acquire new mutations that confer favorable attributes not possessed by the parent molecules. This phenomenon is reflected by the steadily increasing frequency of accepted mutations over the 27 generations.

Figure 8C:
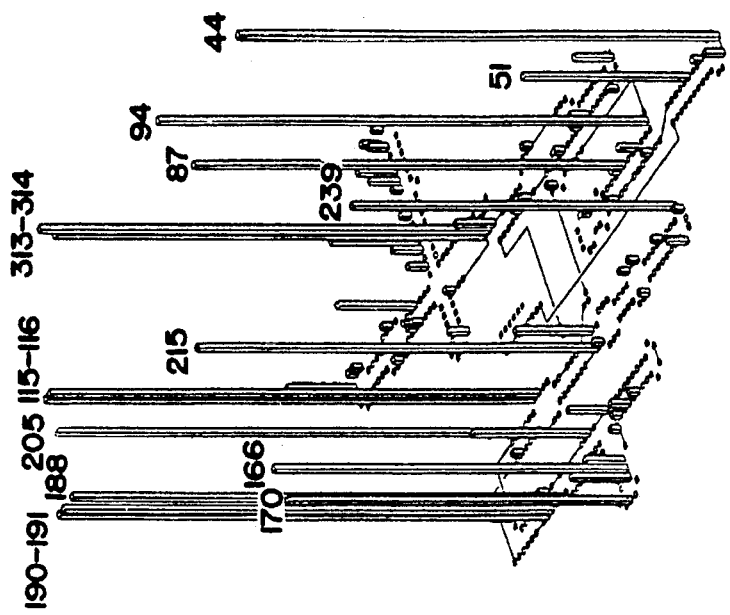
FIG. 8C). Non-mutable primer binding sites are shaded; substrate is shown in black. Commonly-occurring mutations (>30% frequency) are labeled.
Figure 8B:
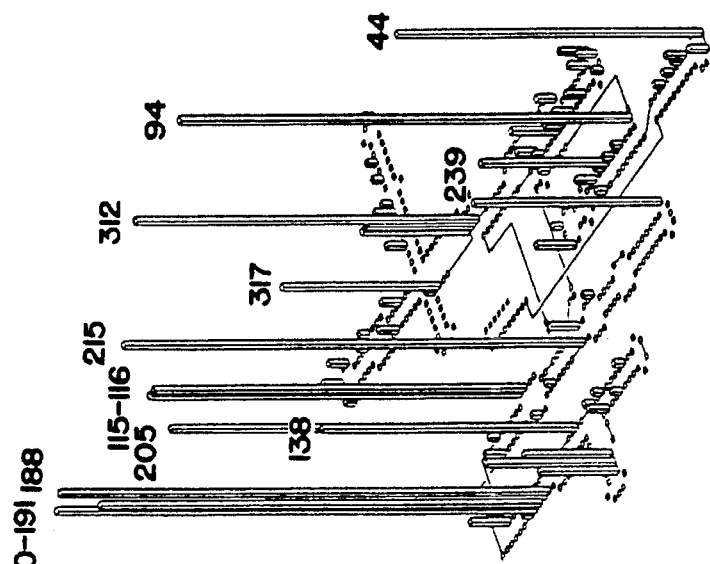
FIG. 8B), and 27 (G27.
Figure 8A:
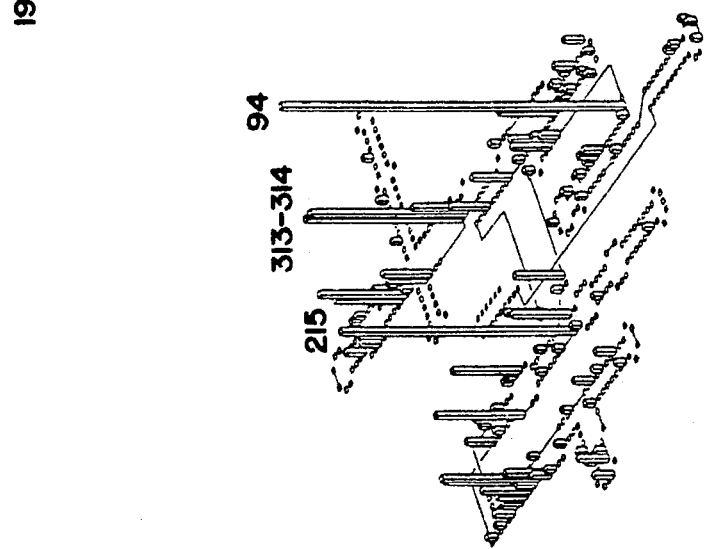
FIG. 8A), 18 (G18.

Sequence data was obtained from 50 randomly-chosen subclones, isolated from the evolving population at G9, G18, and G27 (see FIGS. 8A–8C). FIGS. 8A–8C illustrate sites at which mutations occurred over the course of evolution, superimposed on the secondary structure of the Tetrahymena ribozyme. Box height corresponds to the frequency of mutations (%) at each nucleotide position, based on 50 subclones sequenced at G9 (FIG. 8A), G18 (FIG. 8B), and G27 (FIG. 8C). Nonmutable primer binding sites are shaded; substrate is shown in black. Commonly-occurring mutations (>30% frequency) are labeled.

The mean number of mutations per subclone rose from 5.9 at G9, to 12.7 at G18, and to 16.5 at G27. Most of the mutations occurred within the phylogenetically conserved portions of the ribozyme that were randomized in the initial population (see FIG. 7). However, 26% of the total mutations at G18, and 38% at G27, occurred in peripheral regions as a result of ongoing mutagenesis. Most of the commonly-occurring mutations (>30% frequency) that occur in the G18 subclones (see FIG. 8B) were not observed at G9 (FIG. 8A), suggesting that these mutations arose in response to the increased selection pressure designed to enhance substrate binding affinity. Between G18 and G27, nearly all of the most commonly-occurring mutations continued to increase in frequency (FIG. 8C). However, two significant mutations, the NGAA insertion between positions 51 and 52 and the C→U change at position 170, first appeared during this interval, suggesting that these mutations arose in response to the increased selection pressure designed to enhance the catalytic rate.

2. Concerted and Mutually-Exclusive Mutations

The changes at nucleotide positions 188, 190, and 191 in the P5a region (FIG. 1) co-occur in 90% of subclones, while mutations in the J4/5 and J5/4 internal loop at positions 115, 116, and 205 co-occur in 68% of the subclones at G18. Interestingly, the J4/5 and J5/4 mutations co-occur only if the set of P5a mutations is also present ($c^2=110$, $p<0.001$), suggesting an interaction between these two regions.

The 313:G→Y and 314:A→G mutations nearly always occur together. These mutations co-occur in 16 of 50 subclones at G9, 11 of 50 subclones at G18, and 44 of 50 subclones at G27. Only two G27 subclones contain the mutation at position 313 but lack the mutation at position 314. At G9 and G18, the 313 mutation always occurs as a G→U change. At G27, however, the 313 mutation occurs primarily as a G→C change, with the G→U change occurring only once. The GA sequence normally present at positions 313–314 is thought to form a short duplex structure (P9.0) that brings the 3'-terminal guanosine residue of the ribozyme into the catalytic core (Michel et al., *Nature* 342: 391–395 (1989); Michel et al., *Genes Dev.* 4: 777–788 (1990); Michel, et al., *J. Mol. Biol.* 216: 585–610 (1990)). The 3'-OH of this guanosine serves as the nucleophile in the RNA-catalyzed phosphoester reaction. Although the 313–314 mutation would prevent the P9.0 duplex from forming, the 313–314:GA→UG change confers selective advantage with respect to the DNA-cleavage reaction, as demonstrated by site-directed mutagenesis studies (Beaudry & Joyce, *Id.* (1992)). The appearance of the 313–314:GA→CG change, between G18 and G27, suggests that this altered form of the 313–314 mutation may contribute to the improved catalytic rate of the DNA-cleavage reaction.

The 312:C→A mutation occurs only if the 313–314:GA→YG mutations are not present. The 312:C→A change is present in 4 of 25 subclones at G3, 8 of 25 subclones at G6, and 5 of 50 subclones at G9 (Beaudry & Joyce, *Id.* (1992)). There is a dramatic rise in the frequency of the 312:G→A mutation between G9 and G18, followed by an equally dramatic drop between G18 and G27 (see FIGS. 8A–C). As the frequency of the 312:G→A mutation declines, the 313–314:GA→YG mutations become more abundant.

The 215:G→A mutation, present at high frequency in all of the studied populations, putatively allows a Watson-Crick base pair to form with the U at position 258 (FIG. 1). This change is present in nearly all of the subclones at G18 and G27. Of the 12 individuals that lack this mutation, 11 carry a U→C change at position 258, which would allow a Watson-Crick pair to form with the wild-type G at position 215. Thus, in 99 of 100 subclones from G18 and G27, a Watson-Crick base pair is expected to form between positions 215 and 258.

3. Improvement of DNA Binding Affinity

Beginning with G10, the concentration of DNA substrate employed during the RNA-catalyzed reaction was lowered from 10 μM to 0.2 μM to impose increased selection pressure favoring individuals with enhanced substrate binding affinity. In order to assess the impact of this change, $K_D$ values for the complex between ribozyme and DNA product (GGCCTCT) were determined for the population of ribozymes at every third generation over the 27 generations (see FIG. 9).

Figure 9A:
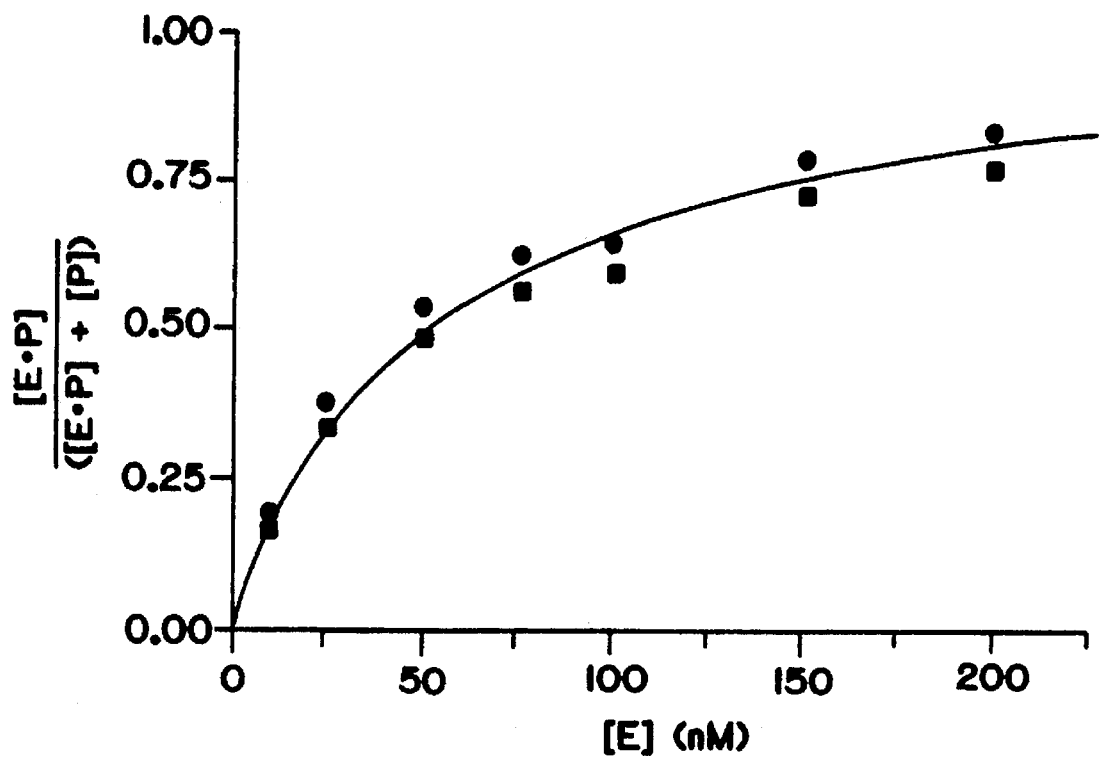
FIGS. 9A and 9B illustrate the improvement in substrate binding affinity over 27 successive generations of in vitro evolution.
Figure 9B:
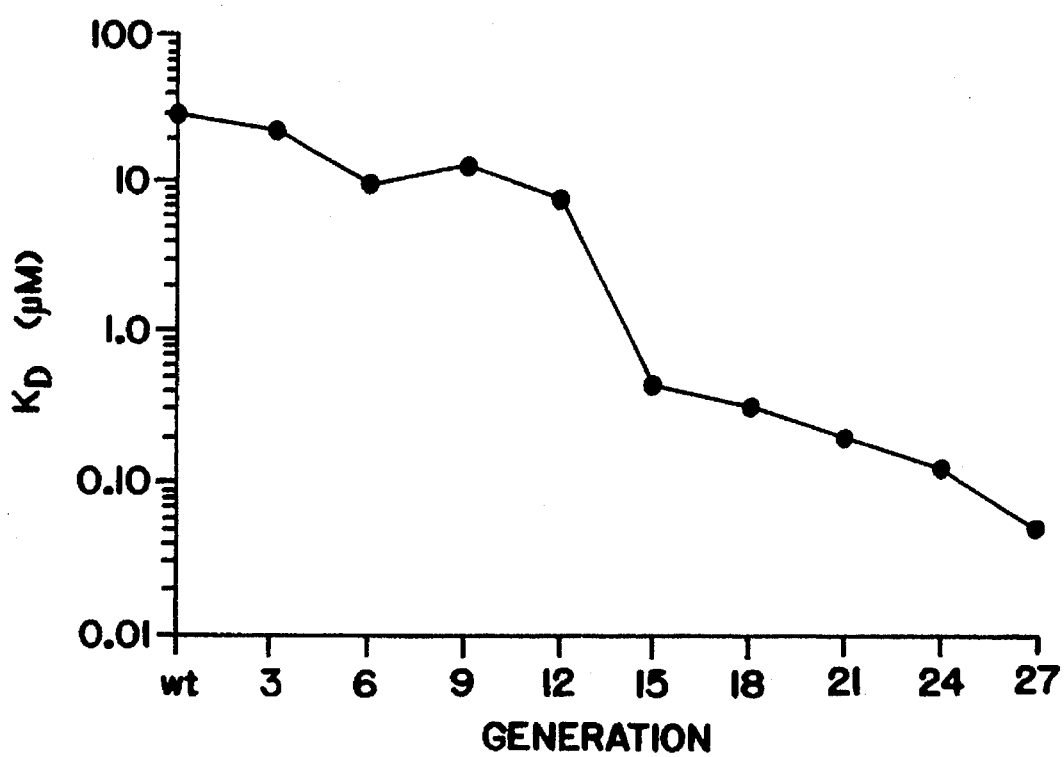

FIGS. 9A and 9B illustrate the improvement in substrate binding affinity over 27 successive generations of in vitro evolution. FIG. 9A represents a typical binding curve showing data obtained for the G27 population of ribozymes. J and B indicate data from two different gel-shift experiments. Data was fit by a least squares method to a theoretical binding curve (indicated by solid line), given by the equation: $y=[E]/([E]+K_D)$, where y is the fraction of product (P) bound to ribozyme (E). In this case, $K_D$=51 (±2) nM. FIG. 9B shows the $K_D$ for the population of ribozymes at every third generation. Standard errors averaged 11%.

The DNA product rather than substrate was employed to avoid a cleavage reaction during the gel-shift analysis. The binding affinity for the product is assumed to be similar to that of the substrate, based on previous studies showing that the wild-type ribozyme binds the RNA substrate with the same affinity as it binds the product (Pyle et al., *PNAS USA* 87: 8187–8191 (1990); Herschlag & Cech, *Biochemistry* 29: 10159–10171 (1990b)).

Binding data for each studied population was fit to a theoretical binding curve, an example of which is shown in FIG. 9A for the G27 population. As expected, the greatest improvement in binding affinity occurred between G9 and G18 (FIG. 9B), subsequent to tightening of the selection constraints. After G18, the population became saturated with ribozymes having a $K_D$ of less than 0.2 μM, accounting for the slow but continued improvement between G18 and G27.

4. Kinetic Analysis

Beginning with generation 19, the reaction time was reduced from 1 hr to 5 min to favor selection of ribozymes with increased $k_{cat}$ values. To study the effect of this change, two individuals isolated from the population at G9, G18 and G27 were chosen for formal kinetic analysis (Table 4). These ribozymes are representative of the population from which they were isolated because they contain most of the prominent mutations that occur in their respective populations. In addition, the total number of mutations in each of the studied individuals coincides with the mean number of mutations per subclone in the corresponding population. It is emphasized that the $k_{cat}$ and $K_M$ values of the studied individuals are not equivalent to the average $k_{cat}$ and $K_M$ values for the entire population. It is likely that the catalytic efficiencies of the studied ribozymes are somewhat higher than the average because these ribozymes possess a greater fraction of the dominant mutations than a typical individual in the population. Nevertheless, the relative differences in $k_{cat}$ and $K_M$ values between representative pairs of individuals should be comparable. As expected, the improvement in $k_{cat}$ is greatest between the G18 and G27 ribozymes (Table 4), while the improvement in $K_M$ is greatest between the G9 and G18 ribozymes.

Table 4, illustrating the catalytic parameters of DNA-cleaving enzymatic RNA molecules, is reproduced hereinbelow.

TABLE 4

Catalytic Parameters of DNA-Cleaving Ribozymes

| Ribozyme | Mutations | $k_{cat}$[b] (min$^{-1}$) | $K_M$[b] (μM) | $k_{cat}/K_M$ (M$^{-1}$ min$^{-1}$) |
|---|---|---|---|---|
| wt[a] | 0 | 2.4 (± 0.2) × 10$^{-4}$ | 6.0 ± 1.7 | 4.0 × 10$^1$ |
| G9 #23[a] | 7 | 5.1 (± 0.2) × 10$^{-3}$ | 1.8 ± 0.3 | 2.8 × 10$^3$ |
| G9 #29[a] | 6 | 7.1 (± 0.3) × 10$^{-3}$ | 1.9 ± 0.3 | 3.8 × 10$^3$ |
| G18 #13[c] | 12[f] | 1.7 (± 0.1) × 10$^{-2}$ | 0.24 ± 0.04 | 7.1 × 10$^4$ |
| G18 #66[c] | 13[g] | 1.1 (± 0.1) × 10$^{-2}$ | 0.32 ± 0.08 | 3.5 × 10$^4$ |
| G27 #48[d] | 17[h] | 7.0 (± 0.6) × 10$^{-1}$ | 0.31 ± 0.05 | 2.3 × 10$^6$ |
| G27 #61[e] | 15[i] | 3.3 (± 0.7) × 10$^{-1}$ | 0.11 ± 0.06 | 2.9 × 10$^6$ |

TABLE 4-continued

Catalytic Parameters of DNA-Cleaving Ribozymes

| Ribozyme | Mutations | $k_{cat}^{b}$ (min$^{-1}$) | $K_{M}^{b}$ (μM) | $k_{cat}/K_{M}$ (M$^{-1}$ min$^{-1}$) |
|---|---|---|---|---|

[a] Data obtained previously (see Example 1 above), modified slightly as a result of subsequent statistical analysis.
[b] Measurements were carried out as described in Materials and Methods with:
[c] 0.025 μM ribozyme and 0.125, 0.25, 0.5, and 1.0 μM DNA substrate;
[d] 0.02 μM ribozyme and 0.1, 0.2, 0.4, and 0.8 μM DNA substrate; or
[e] 0.02 μM ribozyme and 0.05, 0.1, 0.2, and 0.4 μM DNA substrate.
[f] 44: G → A, 94: A → U, 115: A → U, 116: G → A; 138: C → A, 188: G → A, 190: U → A, 191: G → U, 205: U → C, 215: C → A, 312: G → A, and 317: U → G. [g] 44: G → A, 94: A → U, 115: A → U, 116: G → A, 138: C → A, 167: U → G, 188: G → A, 190: U → A, 191: G → U, 205: U → C, 215: G → A, 239: U → A, and 312: G → A. [h] 44: G → A, 51/52: insert AGAA, 87: A → del, 94: A → U, 115: A → U, 116: G → A, 166: C → A, 170: C → U, 188: G → A, 190: U → A, 191: G → U, 205: U → C, 215: G → A, 239: U → A, 312: G → A, 350: C → U, and 364: C → U. [i] 44: C → A, 51/52: insert AGAA, 87: A → del, 94: A → U, 115: A → U, 116: G → A, 166: C → A, 170: C → U, 188: G → A, 190: U → A, 191: G → U, 205: U → C, 215: G → A, 313: G → C, and 314: A → G.

5. RNA-Cleavage Activity of G27 Enzymatic RNA Molecules

In order to assess the effect of the evolution procedure on RNA-cleavage activity, the efficiency of RNA-cleavage by both the G27 #48 and G27 #61 ribozymes was compared to that of the wild-type. Single-turnover kinetic experiments revealed that the G27 ribozymes have slightly enhanced RNA-cleavage activity: $k_{cat}/K_M$ values are 2.7 (±0.2)×10$^7$ and 2.3 (±0.2)×10$^7$ M$^{-1}$min$^{-1}$ for clones G27 #48 and G27 #61, respectively, compared to 9.4 (±3.0)×10$^6$ M$^{-1}$min$^{-1}$ for the wild-type. Thus, the 27 generations of in vitro evolution resulted in a 10$^5$-fold improvement of DNA-cleavage activity and a 2 to 3-fold enhancement of RNA-cleavage activity. Similarly, gel-shift experiments revealed a significantly greater improvement in DNA binding affinity compared to RNA binding affinity. Ribozymes G27 #48 and G27 #61 bind the DNA product with a $K_D$ of 4 nM and 1 nM, respectively, compared to 30 μM for the wild-type, and bind the RNA product with a $K_D$ of 0.5 nM and 0.4 nM, respectively, compared to 1.5 nM for the wild-type. Thus, the G27 ribozymes exhibit a 10$^4$-fold improvement in DNA binding affinity and a 3 to 4-fold improvement in RNA binding affinity.

6. Generations 28–36

The aforementioned evolutionary procedures continue to be applied to produce subsequent generations of enzymatic RNA molecules. Data for generations G28–G36 has been gathered and analysis is ongoing. Critical mutation sites identified as described above continue to be of importance, as shown in FIG. 10.

Figure 10:
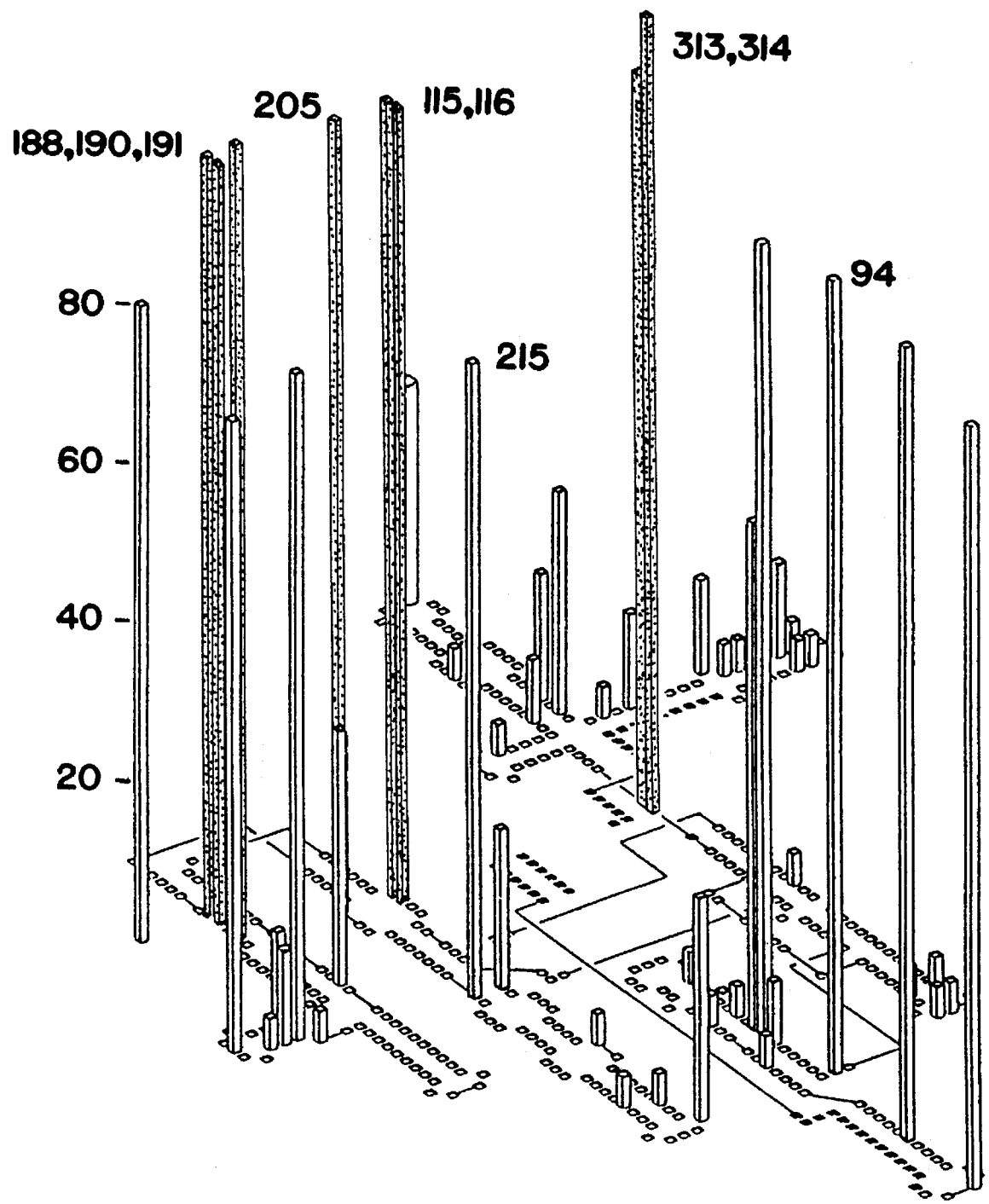
FIG. 10 illustrates sites at which mutations occurred over the course of evolution, superimposed on the secondary structure of the Tetrahymena ribozyme. Box height corresponds to the frequency of mutations (%) at each nucleotide position, based on 50 subclones sequenced at generation 36. Non-mutable primer binding sites are shaded; substrate is shown in black. Commonly-occurring mutations (>30% frequency) are labeled (dark bars).

FIG. 10 illustrates sites at which mutations occurred over the course of evolution, superimposed on the secondary structure of the Tetrahymena ribozyme. Box height corresponds to the frequency of mutations (%) at each nucleotide position, based on 50 subclones sequenced at generation 36. Non-mutable primer binding sites are shaded; substrate is shown in black. Commonly-occurring mutations (>30% frequency) are labeled (dark bars).

Example 3

Discussion of Examples 1–2

It has now been shown that specific catalytic properties of a DNA-cleaving ribozyme can be optimized by appropriate manipulation of the selection constraints during an in vitro evolution procedure. Beginning with a heterogeneous population of ribozymes, enriched for modest DNA-cleavage activity, 18 additional generations were carried out to obtain DNA-cleaving ribozymes that have a catalytic rate of 0.7 min$^{-1}$ and a substrate binding affinity of 10$^{-9}$M. These catalytic parameters are improved 10$^3$-fold and 10$^4$-fold, respectively, compared to the wild-type. The greatest improvement in $K_D$ and $K_M$, (FIG. 9B; Table 4) occurred between G9 and G18 in response to alteration of the selection constraints to favor ribozymes with enhanced affinity for the DNA substrate. Likewise, based on $k_{cat}$ values for representative individuals (Table 4), the greatest improvement in $k_{cat}$ occurred between G18 and G27, following alteration of the selection constraints to favor a faster rate of catalysis.

The DNA-binding affinity of the G27 #48 and G27 #61 ribozymes is comparable to the RNA-binding affinity of the wild-type ribozyme. Previous studies have suggested that the wild-type ribozyme binds RNA more strongly than DNA as a result of interactions between the 2'-OH groups of the RNA substrate and specific nucleotides within the catalytic core of the ribozyme (Pyle & Cech, Nature 350: 628–631 (1991); Pyle et al., Nature 358: 123–128 (1992); Herschlag et al., Biochemistry 32: 8299–8311 (1993)). In binding the DNA substrate with nM affinity, the evolved ribozymes must compensate for the lack of substrate 2'-OH groups by forming alternative interactions that provide an additional 5 kcal mol$^{-1}$ of binding energy (at 37° C.).

The Tetrahymena ribozyme binds its substrate through a two-step process involving first, Watson-Crick base pairing between the internal guide sequence (IGS) and the substrate, and second, docking of the IGS/substrate duplex (P1 helix) into the catalytic core of the ribozyme via tertiary interactions (Herschlag, Biochemistry 31: 1386–1399 (1992); Bevilacqua et al., Science 258: 1355–1358 (1992)). Because the sequence of both the IGS and substrate is unchanged throughout the in vitro evolution procedure, it is unlikely that we have evolved compensatory mutations that operate at the first step of binding. Instead, the 5 kcal mol$^{-1}$ of additional binding energy is likely to result from additional tertiary interactions that affect the second step of binding.

Much more can be learned about such interactions by examining the specific mutations that arose in response to the increased selection pressure aimed to improve substrate binding. For example, mutations at positions 115, 116, and 205 in the J4/5 and J5/4 internal loop of the ribozyme (FIG. 1) became prominent in the population between G9 and G18. Both a tertiary structural model of the wild-type ribozyme (Michel & Westhof, J. Mol. Biol. 216: 585–610 (1990)) and experimental evidence suggest that residues in the J4/5 region may interact with the IGS. On the basis of crosslinking data, Wang et al. (Science 260: 504–508 (1993)) concluded that A114 and A115 lie in close proximity to G22 of the IGS (the 5'-terminal residue of the L-21 form of the ribozyme) when P1 is docked into the ribozyme core. The mutations at positions 115 and 116 may enhance P1 docking by allowing new contacts to be made with the IGS, compensating for the lack of 2'-OH groups in the substrate. Such interactions would strengthen binding of both DNA and RNA substrates and might account for the slight improvement in RNA-cleavage activity. This may also explain the observation that the G27 #61 ribozyme efficiently cleaves a modified RNA substrate that has an arabinose sugar at the cleavage site (data not shown). As noted previously, enzymatic RNA molecules according to the present invention are capable of cleaving substrates including nucleotide analogs, irrespective of whether it is the base or the sugar that has been modified, or both.

Co-occurring mutations at positions 188, 190, and 191 in the P5a region also became prominent in the population between G9 and G18. The correlation between these mutations and the co-occurring mutations in the J4/5 and J5/4 internal loop (see Results) suggests a possible interaction between these two regions. It has been proposed that the adenosine-rich bulge in P5a (FIG. 1; positions 183–186) interacts with P4 (Flor, et al., *EMBO J.* 8: 3391–3399 (1989)) by bending at the J5/5a internal loop (Murphy & Cech, *Biochem.* 32: 5291–5300 (1993)), which would place residues G188, U190, and G191 in close proximity to the J4/5 and J5/4 internal loop. Thus, the mutations in P5a may facilitate the contact between residues in the J4/5 region and the IGS.

The evolved ribozymes might compensate for the absent substrate 2'-OH groups by forming new tertiary interactions with the bases, phosphates, and/or sugars of the DNA. Studies suggest that residues in J7/8 of the wild-type ribozyme interact with the 2'-OH groups at positions −3(u) and −2(c) of the RNA substrate (Pyle & Cech, *Nature* 350: 628–631 (1991); Pyle et al., *Nature* 358: 123–128 (1992)). Frequent mutations, however, did not occur in the J7/8 region of the evolved ribozymes, suggesting that new contacts are not made in the vicinity of the DNA substrate at positions −3(t) and −2(c). In addition, specific base contacts seem unlikely, based on the observation that a DNA substrate with a different sequence can be cleaved efficiently by the ribozyme, provided the IGS has been changed in a complementary manner to maintain Watson-Crick base pairing (Raillard & Joyce, unpublished results).

The $10^3$-fold improvement in $k_{cat}$ over the 27 generations is more difficult to rationalize. $k_{cat}$ reflects all first-order rate constants along the reaction pathway, including those related to P1 docking and substrate cleavage. At least part of the enhancement in $k_{cat}$ thus may be attributed to additional tertiary interactions between P1 and the catalytic core, which would favorably affect the docking rate. The cleavage step of the reaction depends on the appropriate positioning of the 3'-terminal guanosine of the ribozyme for attack on the target phosphoester bond of the substrate. This is accomplished by the formation of a base triple involving the attacking guanosine and the G264:C311 base pair within the P7 region of the ribozyme (Michel et al., *Nature* 342: 391–395 (1989)). Mutations at positions 312, 313, and 314 all lie in close proximity to the binding site for the attacking guanosine and may play some role in facilitating the chemical step of the reaction. However, new mutations that became frequent in the population between G18 and G27 in response to the shorter reaction time occurred in peripheral regions, at positions 51/52 and 170. Such mutations may increase first-order reaction rates indirectly through long-range effects or by facilitating folding of the ribozyme into its active conformation.

It is important to note that some mutations may confer no selective advantage with respect to catalysis, but instead enhance the ability of the polymerase enzymes (i.e., reverse transcriptase, T7 RNA polymerase, and Taq polymerase) to operate efficiently during the amplification procedure. Future studies, relying on site-directed mutagenesis analysis, will enable us to assess the contribution made by various mutations, in either the conserved core or the peripheral regions, to substrate binding, first-order reaction rates, and ribozyme folding.

Now that it has been demonstrated that substrate binding and first-order rate constants can be specifically enhanced by in vitro evolution, optimization of other catalytic properties of the DNA-cleaving ribozymes, including turnover and substrate specificity, is being attempted. Turnover might be improved by evolving ribozymes that can carry out a site-specific hydrolysis reaction, subsequent to DNA-cleavage, which removes the attached 3' portion of the DNA substrate from the 3' end of the ribozyme, returning the molecule to its original form. Specificity of the ribozymes for DNA versus RNA substrates might be increased by selecting for DNA-cleavage in the presence of RNA that acts as a competitive inhibitor. One aim is the development of DNA-cleaving ribozymes that have high catalytic efficiency, undergo rapid turnover, and operate in a highly specific manner. Such molecules will contribute to our understanding of the catalytic potential of RNA. In addition, they may have utility as sequence-specific DNA endonucleases and as therapeutic agents directed against viral pathogens.

Example 4

Alternative Methods of Preparing Enzymatic RNA Molecules

One alternative method of preparing wild-type and mutant ribozymes may be described as follows. Wild-type and mutant ribozymes were produced by first isolating the 443 base-pair Eco RI to Hind III restriction endonuclease fragment from the plasmid PT7-21 described by Zaug et al., *Biochemistry* 27: 8924 (1988) using the standard methods described in *Current Protocols in Molecular Biology*, Ausubel et al., eds. John Wiley and Sons, New York (1987).

This 443 base-pair fragment contains the T7 promoter described by Dunn et al., *J. Mol. Biol.* 166: 477–535 (1983) and residues 22–414 of the Tetrahymena IVS and residues 1–25 of the 3' Tetrahymena exon described by Been et al., *Cell* 47: 207–216 (1986). This Eco RI and Hind III fragment was inserted into the M13 vector M13mp18 (which is similar to the vector described by Yanisch-Perron et al., *Gene* 33: 103–119 (1985)), which vector had been previously cleaved with Eco RI Hind III, according to standard subcloning procedures such as those described in *Current Protocols in Molecular Biology*, Ausubel et al, eds. John Wiley and Sons, New York (1987). The resulting M13T7L-21 DNA construct was used to transform *E. coli* host cells according to the transformation procedure described in *Molecular Cloning: A Laboratory Manual* (Maniatis et al., eds., Cold Spring Harbor Laboratories, Cold Spring Harbor, N.Y. (1989)).

Single-stranded DNA was then prepared from the M13T7L-21-transformed cells according to the procedures described in *Current Protocols in Molecular Biology* (*Id.,* 1987). The accuracy of the above construction was confirmed by DNA sequencing using the klenow fragment of *E. coli* DNA polymerase I (Boehringer Mannheim Biochemicals, Indianapolis, Ind.) and the dideoxynucleotide sequencing method (see Sanger et al., *PNAS USA* 74: 5463–5467 (1977)).

The wild-type and mutant ribozymes were prepared directly from the single-stranded M13T7L-21 DNA using a modification of the technique previously described by Joyce and Inoue, *Nucleic Acid Research* 17: 711–722 (1989). The technique involves construction of a template strand that optionally includes one or more mutagenic oligodeoxynucleotides. The resulting partially-mismatched double-stranded DNA is transcribed directly using T7 RNA polymerase.

Briefly, the procedure is as follows. A five-fold molar excess of a terminator polynucleotide and a mutator oligonucleotide were admixed with 5 µg of single-stranded M13T7L-21 DNA and a solution containing 20 mM tris [hydroxy-methyl]aminomethane adjusted to pH 7.5 with HCl(Tris-HCl), 50 mM NaCl and 2 mM $MgCl_2$. This solution was maintained at 70 degrees centigrade (70° C.) for 5 minutes and then steadily cooled to 30° C. over 40 minutes. Fifteen units(U) of T4 DNA ligase (U.S. Biochemicals, Cleveland, Ohio) and 7.5 U of T4 DNA polymerase (U.S. Biochemicals) were admixed into the solution, together with sufficient amounts of reagents to make a solution containing a final concentration of 20 mM Tris-HCl at pH 7.5, 50 mM NaCl, 5 mM $MgCl_2$, 2 mM dithiothreitol (DTT), 1 mM adenosine triphosphate (ATP), and 0.5 mM each of dGTP, dTTP, dATP and dCTP (dNTPs). The resulting solution was maintained at 37° C. for 60 minutes to complete the synthesis of the mutant strand. The resulting DNA was purified by ethanol precipitation and then used to direct the transcription of mutant RNA.

Transcription took place either in a 10 µl volume containing 1 µg of mutant DNA, 2 µCi [$\alpha^{32}p$] GTP and 50 U of T7 RNA polymerase that was prepared as previously described by Davanloo et al., *PNAS USA* 81: 2035–2039 (1984), and the resulting product was purified according to a procedure originally developed by Butler & Chamberlain, *J. Bio. Chem.* 257: 5772–5779 (1982), or in a 400 µl volume containing 10 µg of mutant DNA, 40 µCi [$^3H$]UTP and 2,400 U of T7 RNA polymerase. In either case, the transcription mixture also contained 40 mM Tris-HCl at pH 7.5, 15 mM $MgCl_2$, 10 mM dithiothreitol, 2 mM spermidine, and 1 mM (each) NTPs, and was incubated at 37° C. for 90 minutes. The T7 RNA polymerase was extracted with phenol and the transcription products were purified by ethanol precipitation. The mutant RNA was isolated by electrophoresis in a 5% polyacrylamide/8 M urea gel, eluted from the gel, and purified by ethanol precipitation and chromatography on Sephadex G-50.

The 3' exon sequence was removed by RNA-catalyzed site-specific hydrolysis as has been previously, Inoue et al., *J. Mol. Biol.* 189: 143–165 (1986). Briefly, the RNA was incubated in the presence of 50 mM CHES at pH 9.0 and 10 mM $MgCl_2$ at 42° C. for 1 hour. Wild-type and mutant RNAs were isolated by electrophoresis in a 5% polyacrylamide/8M urea gel, eluted from the gel, and purified by affinity chromatography on du Pont Nensorb (du Pont, Wilmington, Del.). RNAs were sequenced by primer extension analysis using AMV reverse transcriptase (Life Technologies, Inc., Gaithersburg, Md.) in the presence of dideoxynucleotides, using a modification of the methods described by Sanger et al. (*PNAS USA* 74: 5463–5467 (1977)), except for those containing the Delta P9 deletion (not shown), which were sequenced from the 3' end by partial RNase digestion, Donis-Keller et al., *Nucleic Acids Res.* 15: 8783–8798 (1987).

Other methods of preparing enzymatic RNA molecules of the present invention are based on chemical synthesis. Methods useful in the chemical synthesis of RNA are similar to those used to synthesize DNA. The additional 2'-OH group in RNA, however, requires a different protecting group strategy to deal with selective 3'-5' internucleotide bond formation, and with RNA susceptibility to degradation in the presence of bases.

The recently-developed method of RNA synthesis utilizing the t-butyldimethylsilyl group for the protection of the 2' hydroxyl seems to be the most reliable method for chemical synthesis of ribozymes. The method reproducibly yields RNA with the correct 3'-5' internucleotide linkages, with average coupling yields in excess of 99%, and requires only a two-step de-protection of the polymer.

Other useful methods are available. For example, published PCT application no. WO 93/23569 describes other useful methods of chemically synthesizing ribozymes.

The foregoing specification, including the specific embodiments and examples, is intended to be illustrative of the present invention and is not to be taken as limiting. Numerous other variations and modifications can be effected without departing from the true spirit and scope of the present invention.

I claim:

1. An enzymatic RNA molecule consisting of the sequence of SEQ ID NO 26, wherein said sequence includes one or more mutations selected from the group consisting of:
    the substitution of A for G at position 44;
    the insertion of AGAA between positions 51 and 52;
    the deletion of A at position 87;
    the substitution of U for A at position 115;
    the substitution of A for G at position 116;
    the substitution of A for C at position 138;
    the substitution of A for C at position 166;
    the substitution of G for U at position 167;
    the substitution of U for C at position 170;
    the substitution of A for G at position 188;
    the substitution of A for U at position 190;
    the substitution of U for G at position 191;
    the substitution of A for U at position 239;
    the substitution of C for U at position 258;
    the substitution of A for G at position 312;
    the substitution of U for C at position 350; and
    the substitution of U for C at position 364.

2. An enzymatic RNA molecule consisting of the sequence of SEQ ID NO 26, wherein C is substituted for U at position 258.

3. An enzymatic RNA molecule consisting of the sequence of SEQ ID NO 26, wherein said sequence includes one or more mutations selected from the group consisting of;
    the substitution of U for A at position 94,
    the substitution of C for A at position 94, the substitution of C for U at position 205,
the substitution of A for G at position 215,
the substitution of U for G at position 313,
the substitution of C for G at position 313,
the substitution of G for A at position 314,
the substitution of G for U at position 317,
the substitution of C for U at position 317,
the substitution of A for U at position 317, and
the substitution of C for U at position 333;
and one or more mutations selected from the group consisting of:
the substitution of A for G at position 44,
the insertion of AGAA between positions 51 and 52,
the deletion of A at position 87,
the substitution of U for A at position 115,
the substitution of A for G at position 116,
the substitution of A for C at position 138,
the substitution of A for C at position 166,
the substitution of G for U at position 167,
the substitution of U for C at position 170,
the substitution of A for G at position 188,
the substitution of A for U at position 190,
the substitution of U for G at position 191,
the substitution of A for U at position 239,
the substitution of C for U at position 258,
the substitution of A for G at position 312,
the substitution of U for C at position 350, and
the substitution of U for C at position 364.

4. An enzymatic RNA molecule consisting of the sequence of SEQ ID NO 26, wherein U or C is substituted for A at position 94; U is substituted for A at position 115; A is substituted for G at position 116; A is substituted for G at position 188; A is substituted for U at position 190; U is substituted for G at position 191; C is substituted for U at position 205; A is substituted for G at position 215; and UG is substituted for GA at positions 313–314.

5. An enzymatic RNA molecule consisting of the sequence of SEQ ID NO 26, wherein A is substituted for G at position 44; U or C is substituted for A at position 94; U is substituted for A at position 115; A is substituted for G at position 116; A is substituted for C at position 138; A is substituted for G at position 188; A is substituted for U at position 190; U is substituted for G at position 191; C is substituted for U at position 205; A is substituted for G at position 215; A is substituted for G at position 312; and G is substituted for U at position 317.

6. An enzymatic RNA molecule consisting of the sequence of SEQ ID NO 26, wherein A is substituted for G at position 44; U or C is substituted for A at position 94; U is substituted for A at position 115; A is substituted for G at position 116; A is substituted for C at position 138; G is substituted for U at position 167; A is substituted for G at position 188; A is substituted for U at position 190; U is substituted for G at position 191; C is substituted for U at position 205; A is substituted for G at position 215; A is substituted for U at position 239; and A is substituted for G at position 312.

7. An enzymatic RNA molecule consisting of the sequence of SEQ ID NO 26, wherein A is substituted for G at position 44; AGAA is inserted between positions 51 and 52; A is deleted at position 87; U or C is substituted for A at position 94; U is substituted for A at position 115; A is substituted for G at position 116; A is substituted for C at position 166; U is substituted for C at position 170; A is substituted for G at position 188; A is substituted for U at position 190; U is substituted for G at position 191; C is substituted for U at position 205; A is substituted for G at position 215; A is substituted for U at position 239; A is substituted for G at position 312; U is substituted for C at position 350; and U is substituted for C at position 364.

8. An enzymatic RNA molecule consisting of the sequence of SEQ ID NO 26, wherein A is substituted for G at position 44; AGAA is inserted between positions 51 and 52; A is deleted at position 87; U or C is substituted for A at position 94; U is substituted for A at position 115; A is substituted for G at position 116; A is substituted for C at position 166; U is substituted for C at position 170; A is substituted for G at position 188; A is substituted for U at position 190; U is substituted for G at position 191; C is substituted for U at position 205; A is substituted for G at position 215; C is substituted for G at position 313; and G is substituted for A at position 314.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

N N N N A        5

( 2 ) INFORMATION FOR SEQ ID NO:2:

( i ) SEQUENCE CHARACTERISTICS:
        ( A ) LENGTH: 5 base pairs
        ( B ) TYPE: nucleic acid
        ( C ) STRANDEDNESS: single ( D ) TOPOLOGY: linear ( i i ) MOLECULE TYPE: RNA (genomic)

( x i ) SEQUENCE DESCRIPTION: SEQ ID NO:2:

AACAA                                                                                                           5

( 2 ) INFORMATION FOR SEQ ID NO:3:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:3:

AGUUACCAGG CAUGCACCUG GUAGUCA                                                                                   2 7

( 2 ) INFORMATION FOR SEQ ID NO:4:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:4:

GUCUUUAAAC CAAUAGAUUG GAUCGGUUUA AAAGGC                                                                         3 6

( 2 ) INFORMATION FOR SEQ ID NO:5:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:5:

AAATAAATAA ATAAA                                                                                                1 5

( 2 ) INFORMATION FOR SEQ ID NO:6:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:6:

GGCCCTCTAA ATAAATAAAT AAA                                                                                       2 3

( 2 ) INFORMATION FOR SEQ ID NO:7:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:7:

TTTATTTATT TATTTC                                                              16

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATCGATAATA CGACTCACTA TAGGAGGGAA AAGTTATCAG GC                                  42

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CGAGTACTCC AAAACTAATC                                                          20

( 2 ) INFORMATION FOR SEQ ID NO:10:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GGCCCTCT                                                                        8

( 2 ) INFORMATION FOR SEQ ID NO:11:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GGCCCTCTA                                                                       9

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AAATAAATAA ATAAAA                                                              16

( 2 ) INFORMATION FOR SEQ ID NO:13:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GGCCCTCTAA ATAAATAAAT AAAA 24

( 2 ) INFORMATION FOR SEQ ID NO:14:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCAAGCTTGA TCTCGAGTAC TCCAAAACTA ATC 33

( 2 ) INFORMATION FOR SEQ ID NO:15:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CTGCAGAATT CTAATACGAC TCACTATAGG AGGGAAAAGT TATCAGGC 48

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GTAAAACGAC GGCCAGT 17

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CATGATTACG AATTCTA 17

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single (D) TOPOLOGY: linear (ii) MOLECULE TYPE: RNA (genomic)

(xi) SEQUENCE DESCRIPTION: SEQ ID NO:18:

GGCCCUCUCA AAUAAAUAAA UAAA 24

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CCCTCNAAAT AATAAATAA A 21

(2) INFORMATION FOR SEQ ID NO:20:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

CCCTCN 6

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TTTATTTATT TATTT 15

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GGCCCTCTAT TTATTTA 17

(2) INFORMATION FOR SEQ ID NO:23:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GGCCCTCT                                                                                                                 8

( 2 ) INFORMATION FOR SEQ ID NO:24:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:24:

GGCCCUCUAU   UUAUUUA                                                                                                    1 7

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GGCCCTCTCA   AATAAATAAA   TAAA                                                                                          2 4

( 2 ) INFORMATION FOR SEQ ID NO:26:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: rRNA ( x i ) SEQUENCE DESCRIPTION: SEQ ID NO:26:

| GGAGGGAAAA | GUUAUCAGGC | AUGCACCUGG | UAGCUAGUCU | UUAAACCAAU | AGAUUGCAUC | 6 0 |
| --- | --- | --- | --- | --- | --- | --- |
| GGUUUAAAAG | GCAAGACCGU | CAAAUUGCGG | GAAAGGGGUC | AACAGCCGUU | CAGUACCAAG | 1 2 0 |
| UCUCAGGGGA | AACUUUGAGA | UGGCCUUGCA | AAGGGUAUGG | UAAUAAGCUG | ACGGACAUGG | 1 8 0 |
| UCCUAACCAC | GCAGCCAAGU | CCUAAGUCAA | CAGAUCUUCU | GUUGAUAUGG | AUGCAGUUCA | 2 4 0 |
| CAGACUAAAU | GUCGGUCGGG | GAAGAUGUAU | UCUUCUCAUA | AGAUAUAGUC | GGACCUCUCC | 3 0 0 |
| UUAAUGGGAG | CUAGCGGAUG | AAGUGAUGCA | ACACUGGAGC | CGCUGGGAAC | UAAUUUGUAU | 3 6 0 |
| GCGAAAGUAU | AUUGAUUAGU | UUUGGAGUAC | UCG |  |  | 3 9 3 |